(12) United States Patent
Wu et al.

(10) Patent No.: US 10,583,241 B2
(45) Date of Patent: Mar. 10, 2020

(54) DRUG DELIVERY DEVICE

(71) Applicant: Becton, Dickinson and Company, Franklin Lakes, NJ (US)

(72) Inventors: Haiming Wu, Weston, MA (US); Danial P. Ferreira, Milford, CT (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 79 days.

(21) Appl. No.: 14/888,691

(22) PCT Filed: May 2, 2014

(86) PCT No.: PCT/US2014/036701
§ 371 (c)(1),
(2) Date: Nov. 2, 2015

(87) PCT Pub. No.: WO2014/179774
PCT Pub. Date: Nov. 6, 2014

(65) Prior Publication Data
US 2016/0058941 A1    Mar. 3, 2016

Related U.S. Application Data

(60) Provisional application No. 61/819,443, filed on May 3, 2013.

(51) Int. Cl.
*A61M 5/14*     (2006.01)
*A61M 5/145*    (2006.01)
(Continued)

(52) U.S. Cl.
CPC .......... *A61M 5/1413* (2013.01); *A61M 5/145* (2013.01); *A61M 5/1454* (2013.01);
(Continued)

(58) Field of Classification Search
CPC .. A61M 5/1413; A61M 5/145; A61M 5/1454; A61M 5/1626; A61M 5/16813;
(Continued)

(56) References Cited

U.S. PATENT DOCUMENTS 5,743,879 A    4/1998   Kriesel
6,186,982 B1 *  2/2001  Gross ............... A61M 5/14248
                                                       604/132
(Continued)

FOREIGN PATENT DOCUMENTS

WO    WO-2009/092807 A1    7/2009
WO    WO-2009126720 A1    10/2009
(Continued)

*Primary Examiner* — Kevin C Sirmons
*Assistant Examiner* — Tezita Z Watts
(74) *Attorney, Agent, or Firm* — Dickinson Wright PLLC

(57) ABSTRACT

A drug delivery device for injecting medicament, the device including a main body having a surface for contacting a patient, an actuation button (110, 420, 436) movably disposed relative to the main body, and a reservoir disposed within the main body for containing a medicament. The device also includes a needle having a distal end for insertion into a patient, and a lumen extending proximally from the distal end, wherein the lumen is fluidly connectable with the reservoir. The device further includes a removable needle cover (114, 400) for selectively covering the distal end of the needle and selectively preventing movement of the actuation button relative to the main body that initiates activation of the device.

16 Claims, 55 Drawing Sheets

(51) Int. Cl.
*A61M 5/31* (2006.01)
*A61M 5/142* (2006.01)
*A61M 5/162* (2006.01)
*A61M 5/168* (2006.01)
*B65B 55/04* (2006.01)
*A61M 39/20* (2006.01)
*A61M 5/24* (2006.01)
*A61M 39/22* (2006.01)
*A61M 5/20* (2006.01)

(52) U.S. Cl.
CPC ...... *A61M 5/14248* (2013.01); *A61M 5/1626* (2013.01); *A61M 5/16813* (2013.01); *A61M 5/3134* (2013.01); *B65B 55/04* (2013.01); *A61M 5/162* (2013.01); *A61M 39/20* (2013.01); *A61M 39/22* (2013.01); *A61M 2005/14252* (2013.01); *A61M 2005/14256* (2013.01); *A61M 2005/2073* (2013.01); *A61M 2005/2474* (2013.01); *A61M 2205/195* (2013.01); *A61M 2205/70* (2013.01); *A61M 2207/00* (2013.01)

(58) Field of Classification Search
CPC .................. A61M 5/3134; A61M 5/20; A61M 2005/2073; A61M 2005/2006; A61M 2005/14252; A61M 2005/1585; A61M 5/14248
See application file for complete search history.

(56) References Cited

U.S. PATENT DOCUMENTS

| | | | |
|---|---|---|---|
| 6,500,150 B1* | 12/2002 | Gross | A61M 5/14248 |
| | | | 604/110 |
| 8,034,035 B2 | 10/2011 | Weaver et al. | |
| 2004/0138612 A1 | 7/2004 | Shermer et al. | |
| 2005/0065472 A1 | 3/2005 | Cindrich et al. | |
| 2006/0106346 A1 | 5/2006 | Sullivan et al. | |
| 2008/0051727 A1 | 2/2008 | Moberg et al. | |
| 2010/0036318 A1 | 2/2010 | Raday et al. | |
| 2012/0010594 A1 | 1/2012 | Holt et al. | |
| 2012/0191047 A1 | 7/2012 | Raday et al. | |
| 2012/0316506 A1 | 12/2012 | Sonderegger et al. | |
| 2013/0060233 A1 | 3/2013 | O'Connor et al. | |
| 2013/0066274 A1 | 3/2013 | O'Connor et al. | |
| 2013/0110049 A1* | 5/2013 | Cronenberg | A61M 5/14248 |
| | | | 604/180 |
| 2014/0094757 A1* | 4/2014 | Mercer | A61M 5/2448 |
| | | | 604/191 |

FOREIGN PATENT DOCUMENTS

| | | |
|---|---|---|
| WO | WO-2011/075101 A1 | 6/2011 |
| WO | WO-2012019641 A1 | 2/2012 |
| WO | WO-2012145752 A2 | 10/2012 |
| WO | WO-2013055873 A1 | 4/2013 |
| WO | WO-2013/075101 A1 | 5/2013 |

* cited by examiner

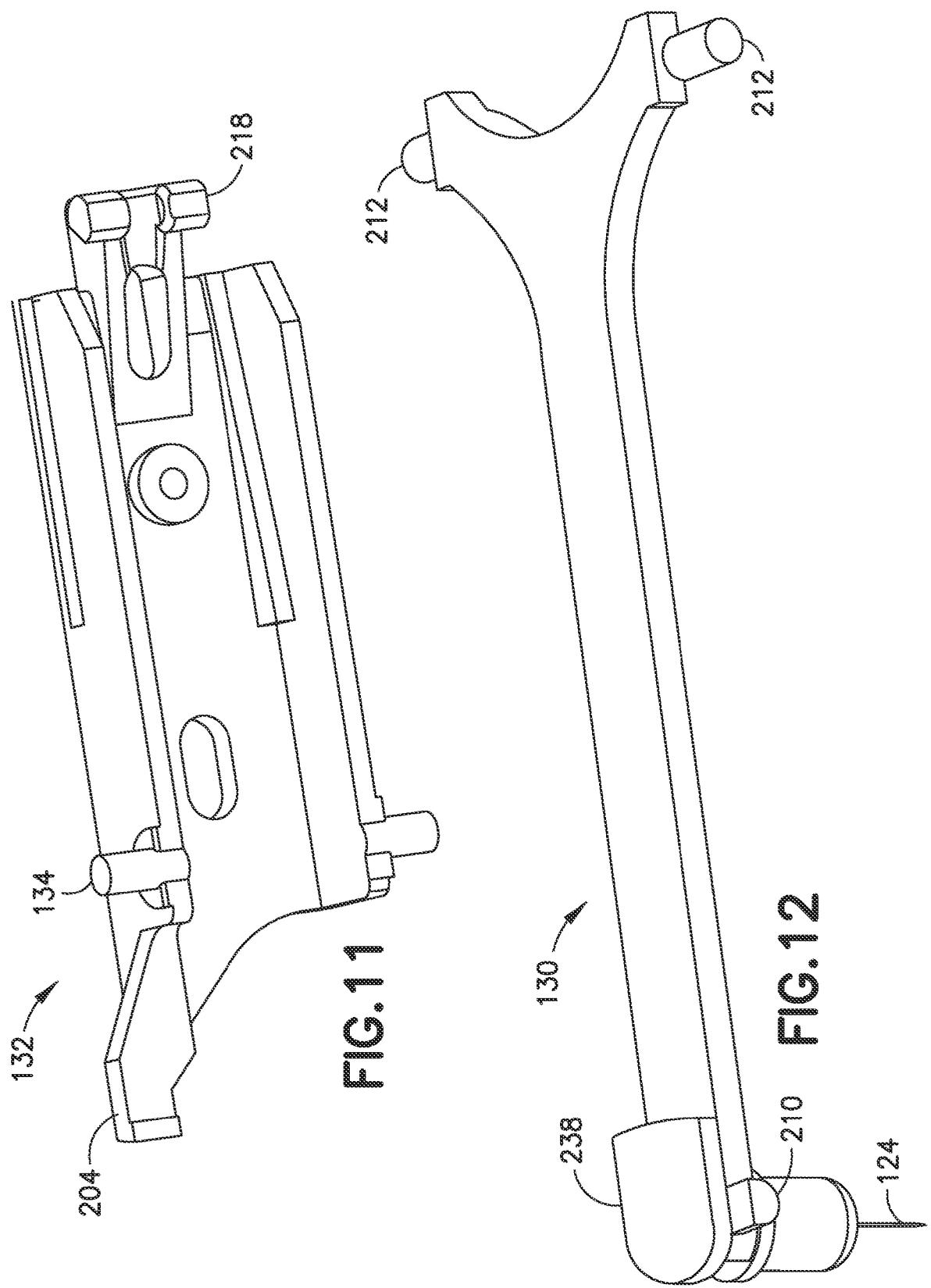

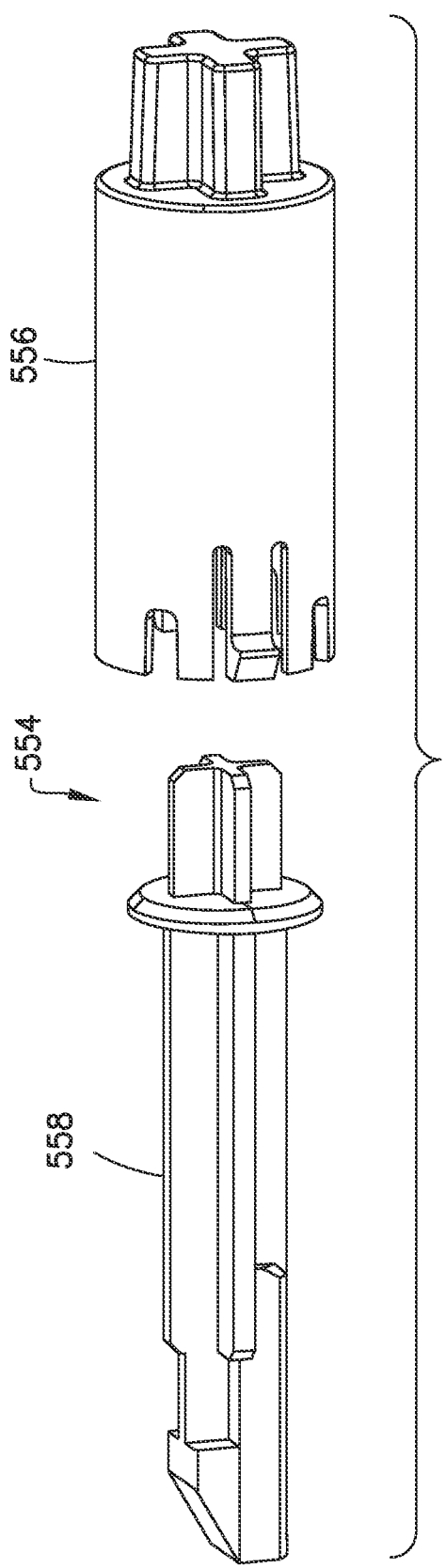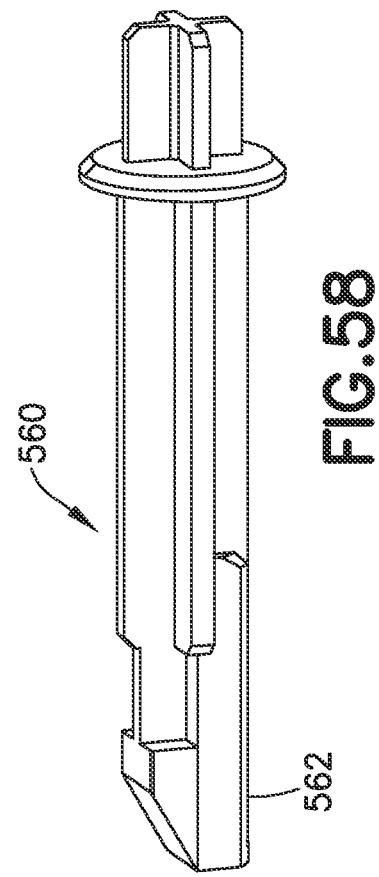

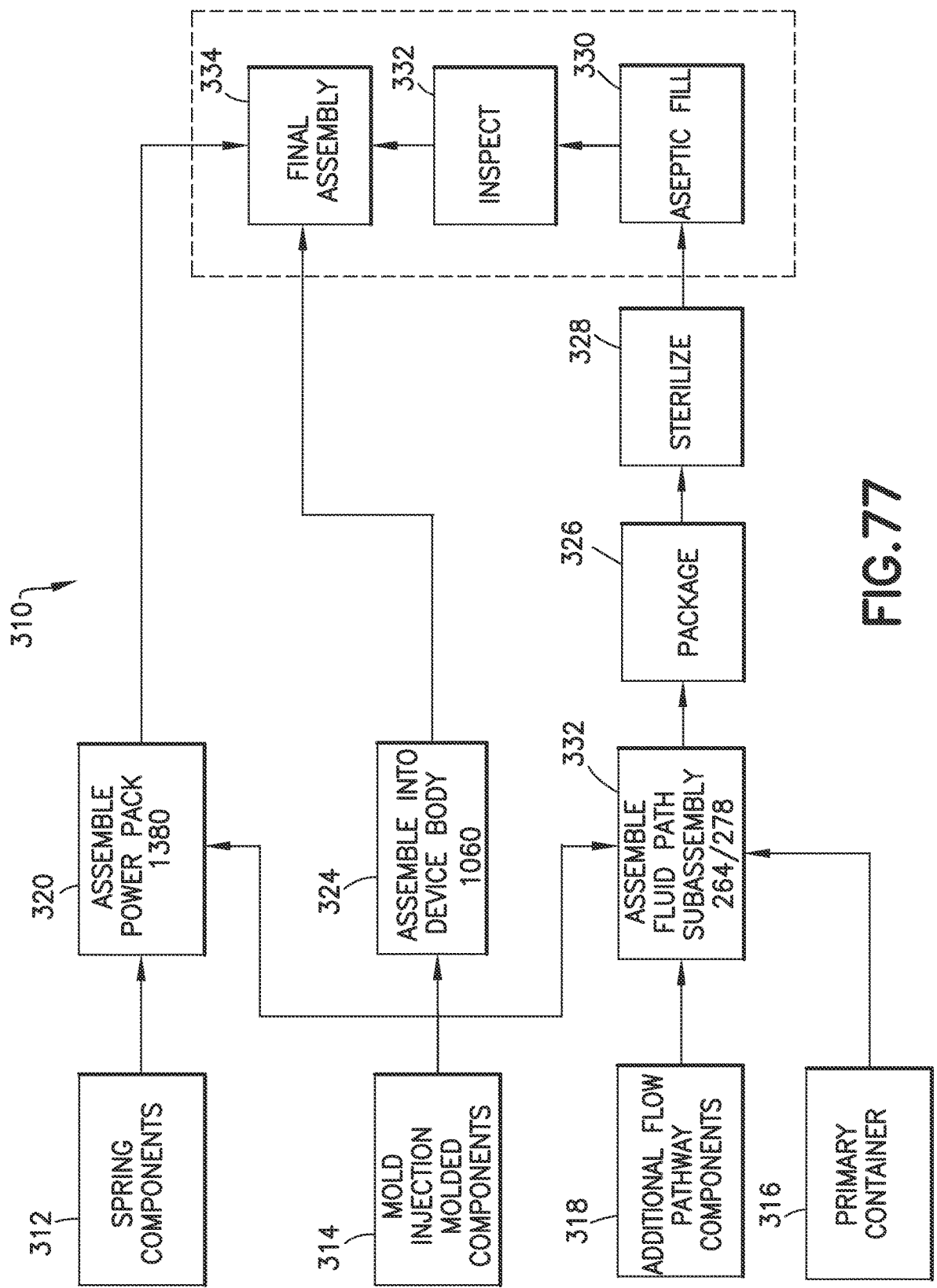

form U.S. Provisional Patent Application Ser. No. 61/819,
DRUG DELIVERY DEVICE

CROSS-REFERENCE TO RELATED APPLICATION

This application claims priority under 35 USC § 119(e) from U.S. Provisional Patent Application Ser. No. 61/819, 443 filed on May 3, 2013, the disclosure of which is incorporated herein by reference in its entirety.

FIELD OF THE INVENTION

The present invention relates to a drug delivery device for parenteral administration of a medicament.

BACKGROUND OF THE INVENTION

Drug delivery devices in the form of infusers are known in the prior art for administering medicament to a patient. Infusers are intended for mounting onto a patient's skin for self-administration of a medicament. Activation of the infuser not only provides for injection of a needle into a patient's skin, but also to cause auto-drive of a plunger to drive medicament into the patient via the injected needle. Typical infuser constructions have the needle fixed to the reservoir. For example, with reference to U.S. Pat. No. 5,858,001 to Tsals et al., an infuser is disclosed that is activated through swivel displacement of a reservoir-containing body. A needle that is also caused to penetrate the skin of a patient with the swivel displacement of the body is attached to the Tsals et al. device. The needle is fixed to the body to move therewith. Other types of infusers are known, including those which use standard needle-mounted syringe barrels. With many infusers, the ability to control the insertion of the needle independent of the administration of medicament is limited.

PCT Publication WO 2011/146166, which is hereby incorporated by reference in its entirety, discloses an infuser in which activation of an actuator causes a spring to move a stopper in a reservoir from a first position toward a second position, and also causes a needle driver to displace a patient needle from a first state toward a second state. The needle moves relative to the reservoir, and separately from the stopper.

SUMMARY OF EMBODIMENTS OF THE INVENTION

Accordingly, it is an aspect of the present invention to provide a medical device with improved user operation and safety.

The foregoing and/or other aspects of the present invention are achieved by providing a drug delivery device for injecting medicament, the device including a main body having a surface for contacting a patient, an actuation button movably disposed relative to the main body, and a reservoir disposed within the main body for containing a medicament. The device also includes a needle having a distal end for insertion into a patient, and a lumen extending proximally from the distal end, wherein said lumen is fluidly connectable with the reservoir. The device further includes a removable needle cover for selectively covering the distal end of the needle and selectively preventing movement of the actuation button relative to the main body that initiates activation of the device.

Additional and/or other aspects and advantages of the present invention will be set forth in the description that follows, or will be apparent from the description, or may be learned by practice of the invention

BRIEF DESCRIPTION OF THE DRAWINGS

The above and/or other aspects and advantages of embodiments of the invention will be more readily appreciated from the following detailed description, taken in conjunction with the accompanying drawings, in which:

FIG. 11 is a bottom perspective view of a lever of the device of FIG. 1;

FIG. 12 is a perspective view of a needle arm of the device of FIG. 1;

FIG. 57 is a top perspective, exploded view of a two-part barrel plunger in accordance with the embodiment of the present invention;

FIG. 58 is a top perspective view of a plunger link in accordance with another embodiment of the present invention;

FIG. 77 is a flow chart illustrating a process of assembly of the device of FIG. 1.

Figure 1:
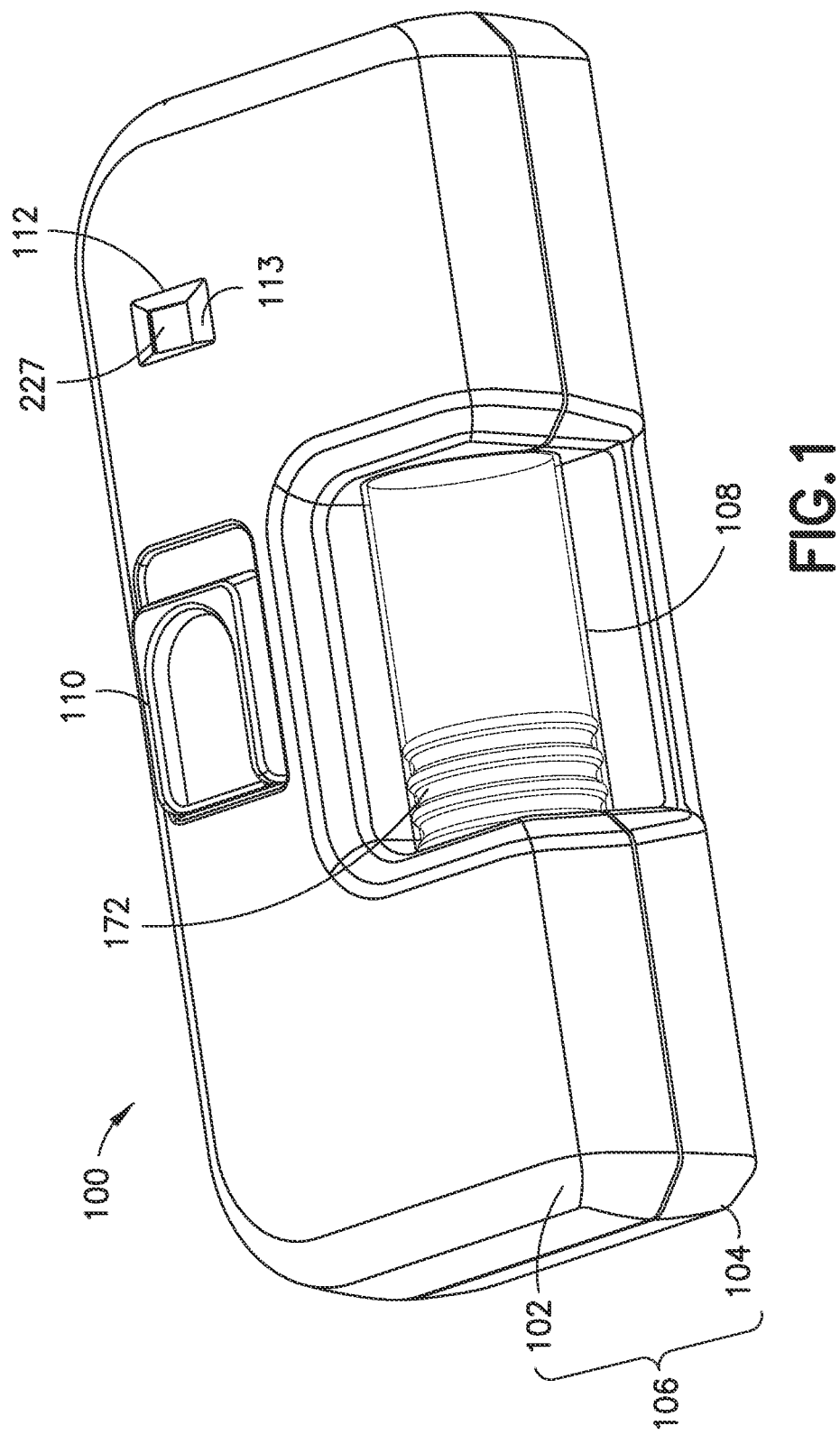
FIG. 1 is a top perspective view of infusion medical device in accordance with an embodiment of the present invention.

DETAILED DESCRIPTION OF EMBODIMENTS
OF THE PRESENT INVENTION

Reference will now be made in detail to embodiments of the present invention, which are illustrated in the accompanying drawings, wherein like reference numerals refer to like elements throughout. The embodiments described herein exemplify, but do not limit, the present invention by referring to the drawings. As will be understood by one skilled in the art, terms such as up, down, bottom, and top are relative, and are employed to aid illustration, but are not limiting.

FIG. 1 is a top perspective view of an infusion device or infuser 100 for infusing a medicament into a patient. Although a user other than a medicament recipient (for example, a health care professional) can use the device 100, for brevity, the term "user" will be employed hereinafter to refer to a patient or other user. The device 100 has a top cover 102 and a bottom cover 104 that, together, form a main body 106. The device 100 also includes a reservoir or syringe barrel 108, a button 110, and a status viewport 112. Through the status view port 112, as will be subsequently described in greater detail, a user can view the progress of the infusion of the medicament. For example, the device 100 can function in three stages: a pre-activated stage (ready for activation), a first activation stage, and an end-of-dose or second activation stage. According to one embodiment, an indicator is visible through the viewport 112 to indicate each of these three stages. As an example, three colors can be used to represent the three stages. As other examples, three numbers, three symbols, three letters, or three words or phrases can be visible through the viewport 112 to represent the three stages. According to one embodiment, as shown in FIG. 1, a portion 113 of the viewport 112 is slanted. This reflects light into the viewport 112 and aids the user in viewing the status of the device 100.

Figure 2:
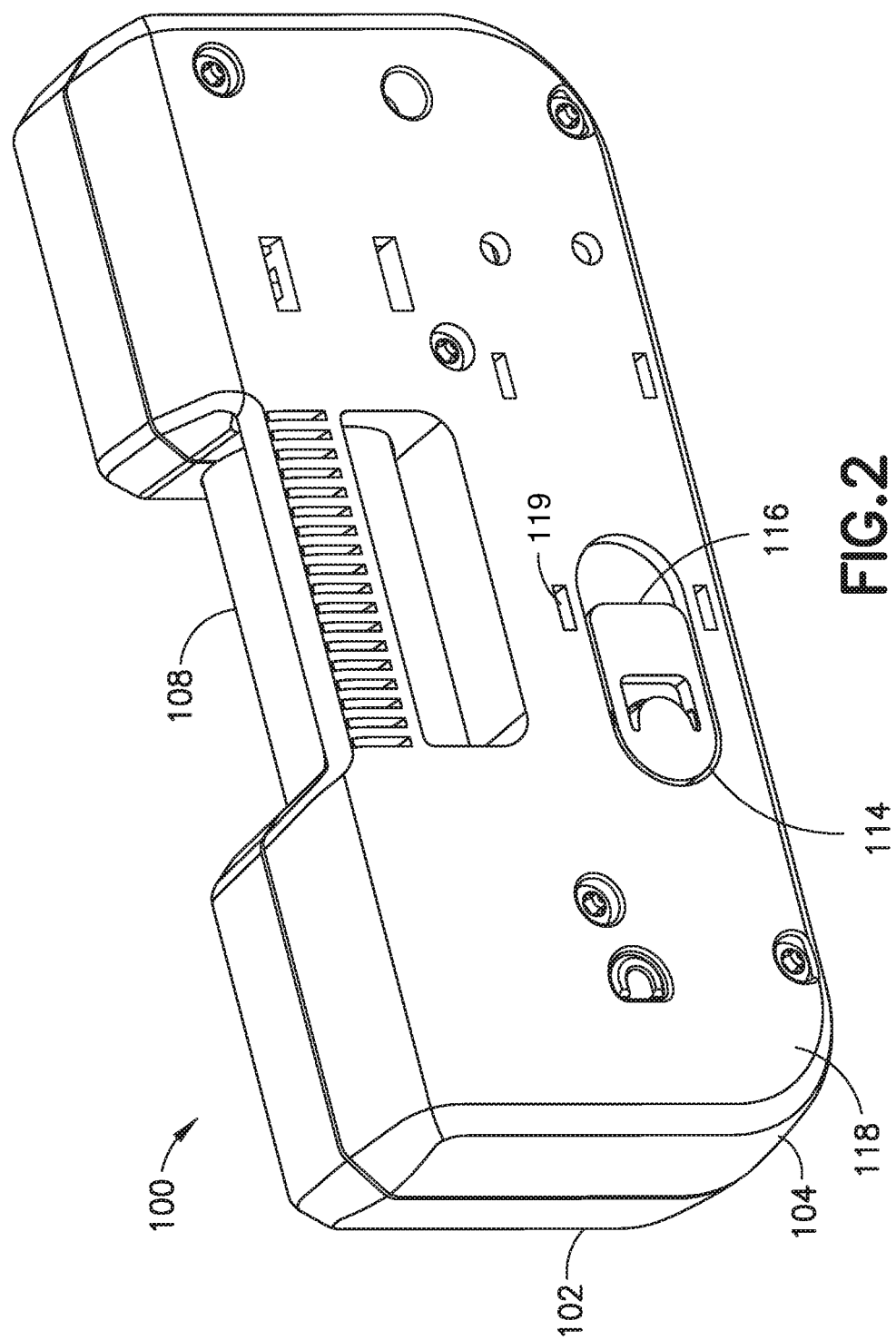
FIG. 2 is a bottom perspective view of the device of FIG. 1.

FIG. 2 is a bottom perspective view of the device 100, which includes a removable needle cover 114. Preferably, the needle cover 114 is manufactured in a two-shot molding process. As shown in FIG. 2, the tab 116 of the needle cover 114 preferably folds substantially parallel to and against the bottom of the device 200, on which there is an adhesive 118 for attaching the device to a patient's skin. According to one embodiment, the adhesive 118 is an adhesive pad secured on one side to the bottom cover 104, and having a patient adhesive on the opposing side. A removable adhesive liner preferably protects the patient adhesive, and is removed prior to securing the device to the patient's skin.

According to one embodiment, as shown in FIG. 2, the bottom cover 104 also includes one or more access slots 119, through which an assembler can, for example, access the button 110 and/or the needle cover 114 during assembly of the device 100.

Figure 3:
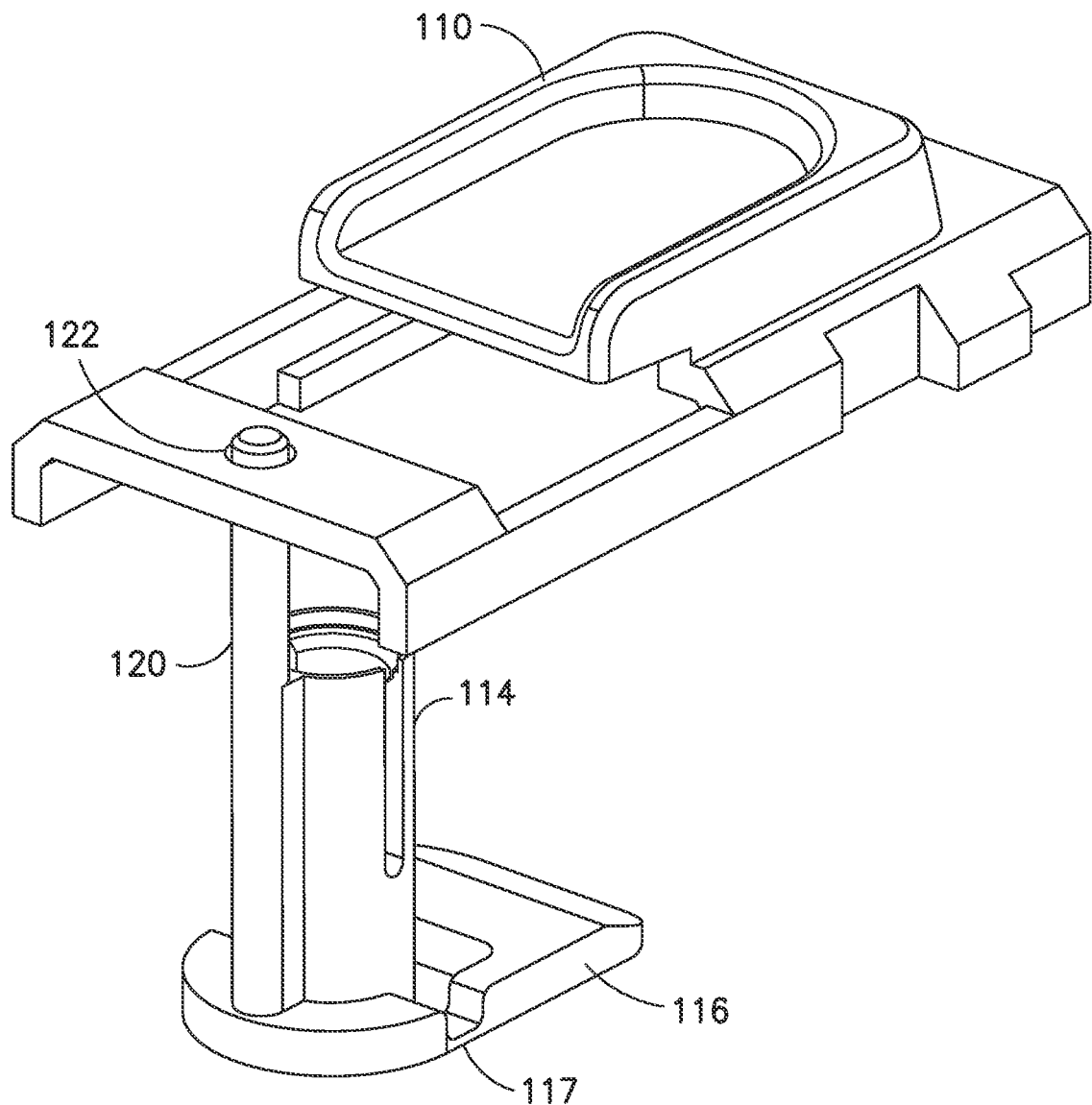
FIG. 3 is a perspective view illustrating the relationship between a button and a needle cover in a pre-activated stage, in accordance with an embodiment of the present invention.

FIG. 3 is a perspective view illustrating the relationship between the button 110 and the needle cover 114 in the pre-activated stage. As shown in FIG. 3, the needle cover 114 includes a safety extension 120 that extends through the bottom cover 104 and engages an engagement hole 122 of the button 110. This engagement prevents the button 110 from moving and activating the device 100 prior to removal of the needle cover 114.

According to one embodiment, the safety extension 120 and the needle cover 114 are integrally formed as a unitary construction. According to another embodiment, the safety extension 120 is originally formed as a separate element, and subsequently joined to the needle cover 114, for example, by snapping the safety extension into a recess in the needle cover 114, or using an adhesive.

To remove the needle cover 114, the user unfolds the tab 116 about a hinge 117 (for example, a living hinge 117) to extend substantially perpendicular to the bottom cover 104, and then pulls the needle cover 114 out of the device 100, thereby uncovering a hollow patient needle 124 and permitting movement of the button 110. Preferably, the user removes the release liner and then removes the needle shield 114, thereby freeing the button 110 for movement, as subsequently described in greater detail. Optionally, the user removes the release liner from the adhesive 118 subsequent to removing the needle cover 114, or they are removed in a combined fashion.

According to one embodiment, the release liner and the needle cover 114 are connected, and the release liner is retained on the needle cover 114 after removal from the infusion device. Such an embodiment allows the user to easily recycle or dispose of the connected release liner and needle cover 114. Examples of ways to connect a release liner and a needle cover can be found in the commonly-owned international application published as WO 2011/075101, the disclosure of which is incorporated herein in its entirety.

Figure 4:
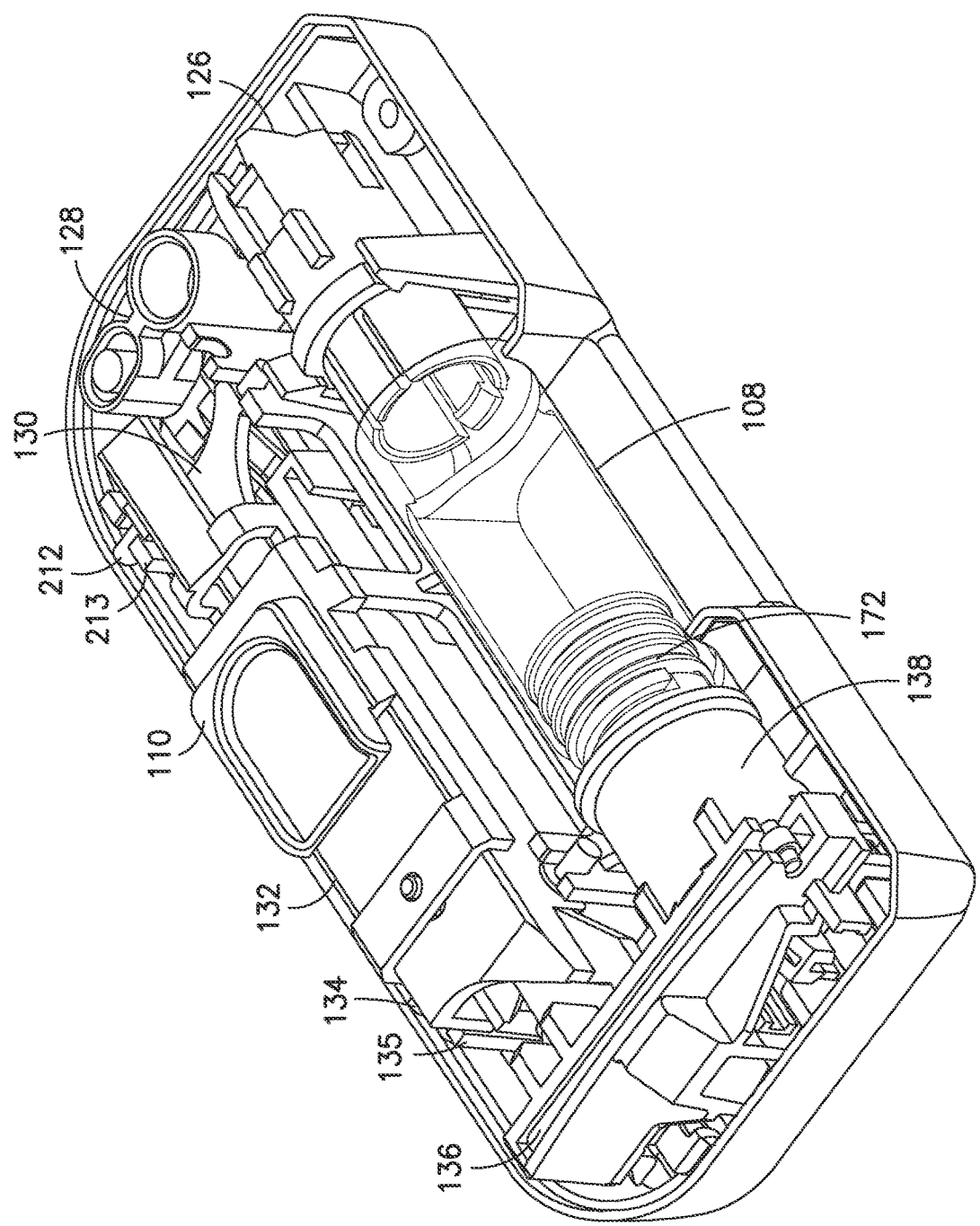
FIG. 4 is a top perspective view of the device of FIG. 1 in a pre-activation stage with a top cover removed.

FIG. 4 is a top perspective view of the device 100 in the pre-activated stage with the top cover 102 removed. The device 100 includes a valve cover 126, a rocker 128, a needle arm 130, a lever 132 that rotates about a pivot 134, a shutter 136, and a frame 138 that houses the shutter 136 and guides its movement. For reference purposes, the shutter 136 is disposed at a first end of the main body 106 and the rocker 128 is disposed at a second end of the main body 106.

Figure 5:
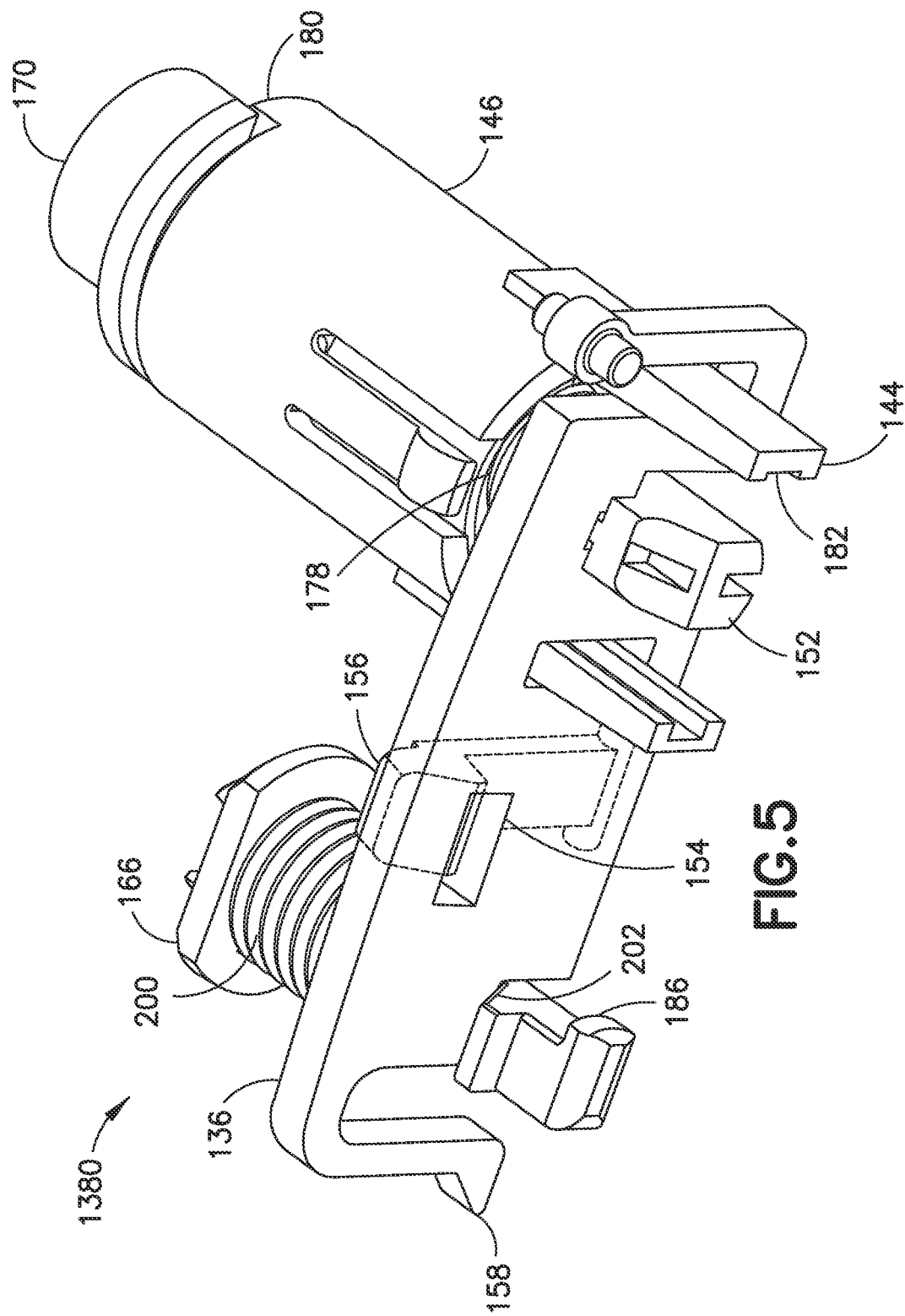
FIG. 5 is a partial perspective view illustrating the interaction of components of a power pack of the device of FIG. 1 in the pre-activated stage.
Figure 6:
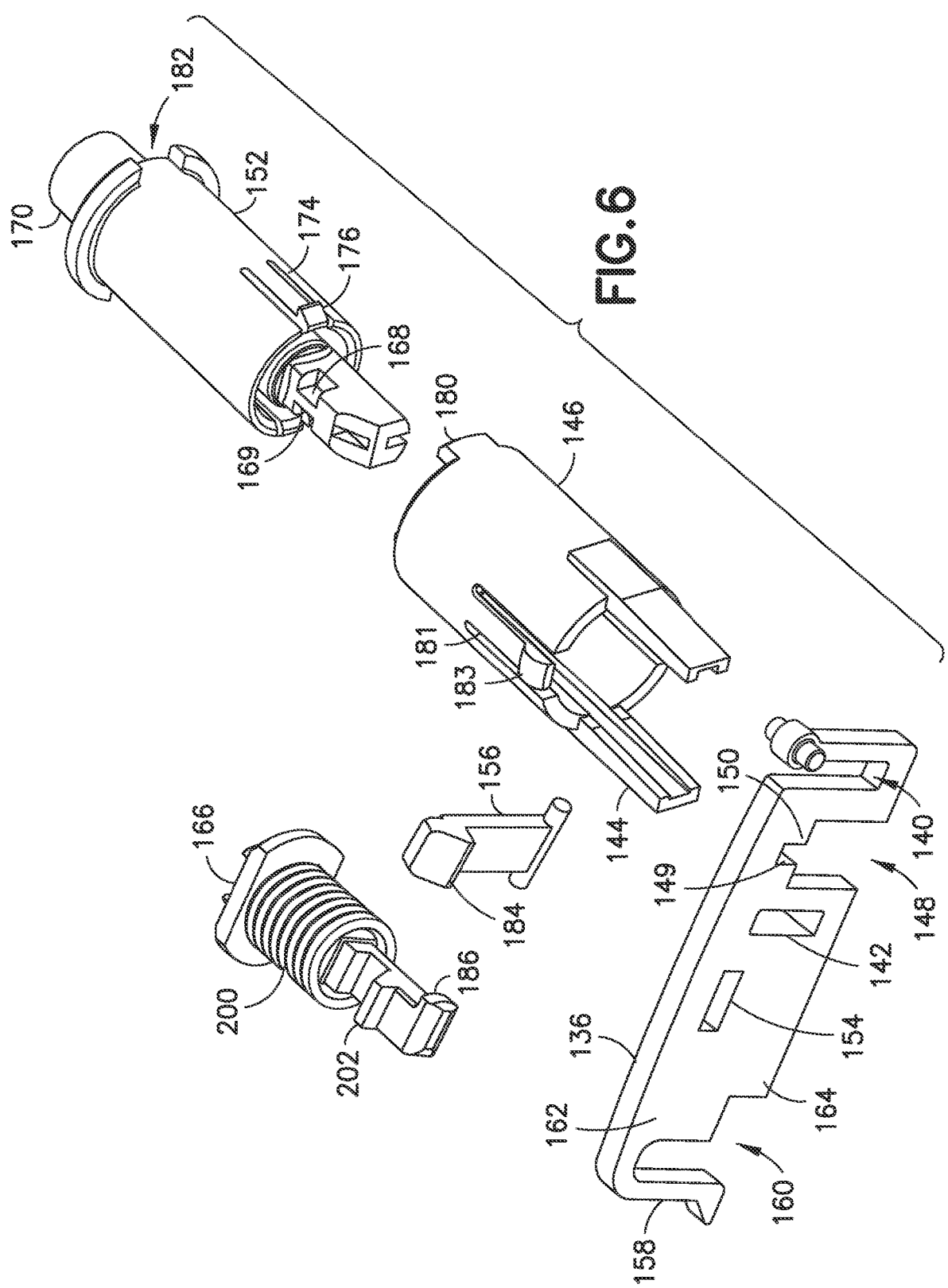
FIG. 6 is an exploded perspective view of the components illustrated in FIG. 5.
Figure 7:
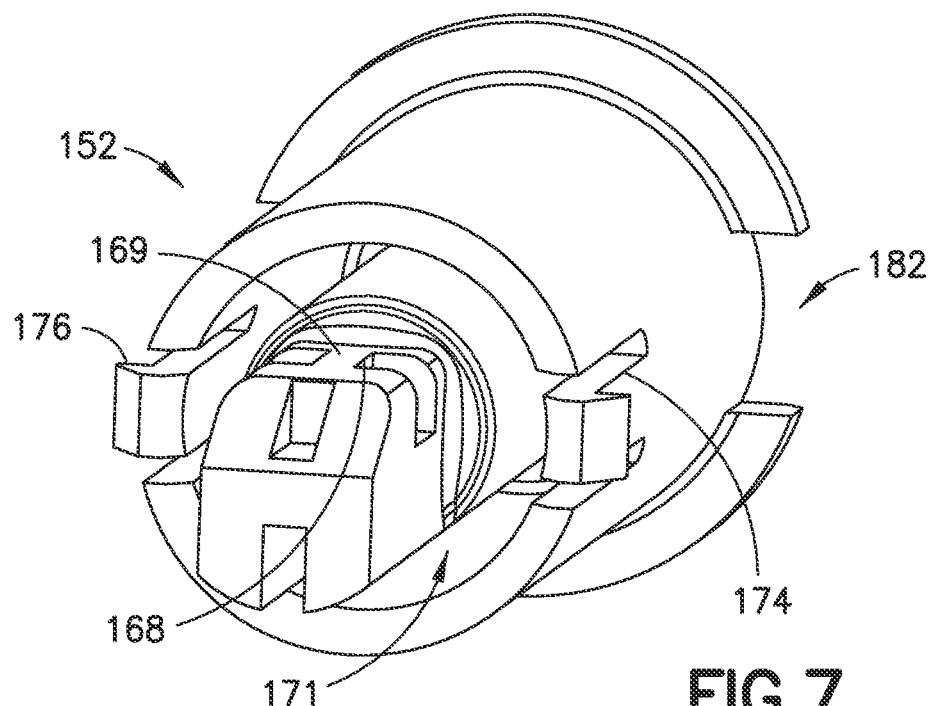
FIG. 7 is a perspective view of a barrel plunger of the device of FIG. 1.
Figure 8:
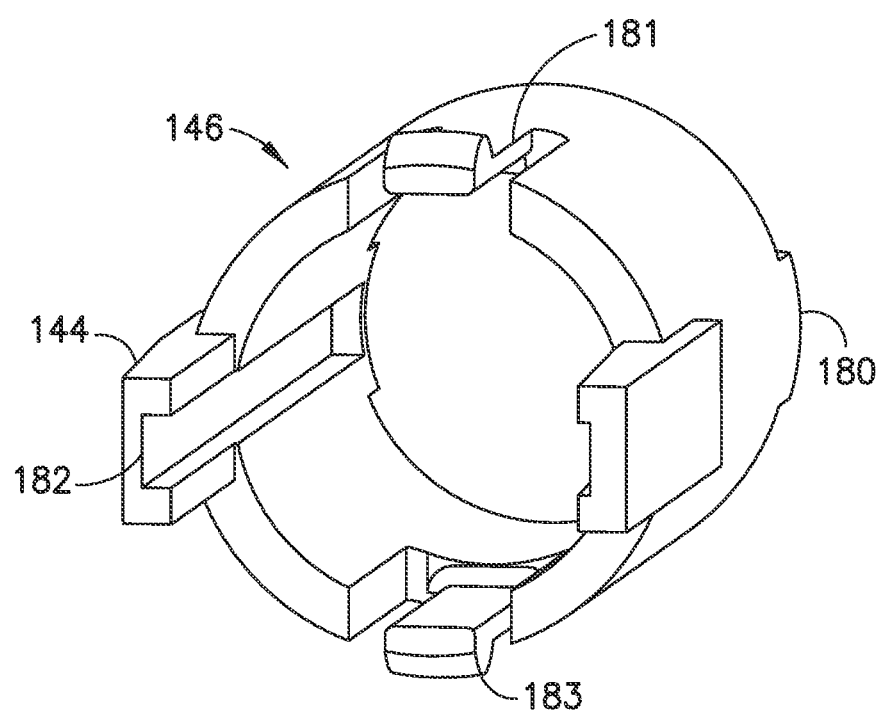
FIG. 8 is a perspective view of an outer telescoping member of the device of FIG. 1.
Figure 9:
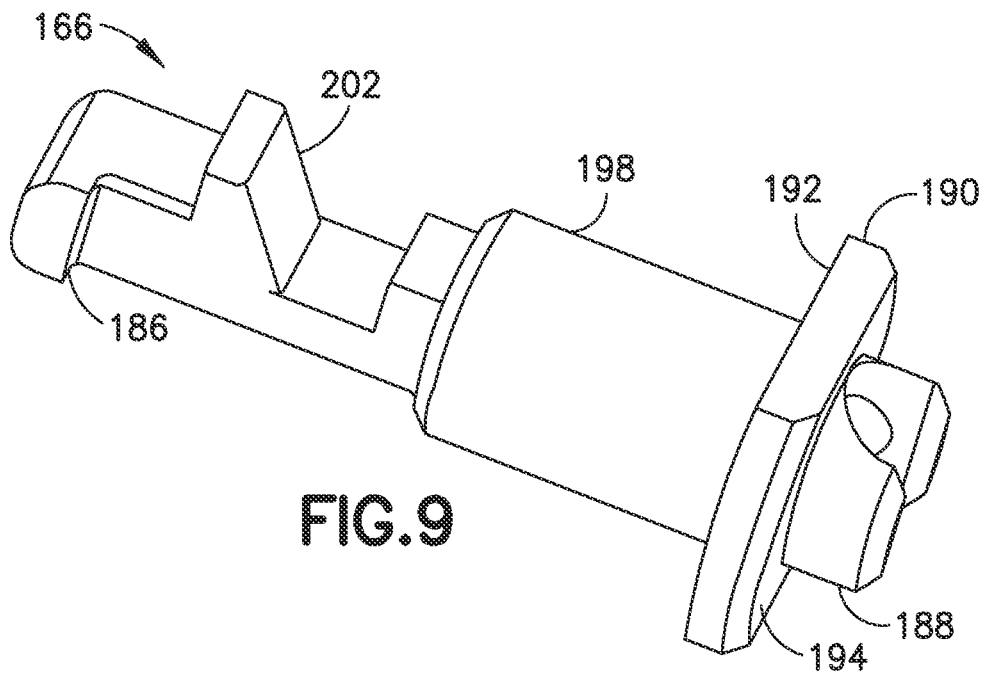
FIG. 9 is a perspective view of a needle actuation plunger of the device of FIG. 1.

FIGS. 5-9 illustrate several components of a power pack 1380 of the device 100 in the pre-activated stage. In particular, FIG. 5 is a partial perspective view illustrating the interaction of several components with the shutter 136 in the pre-activated stage. For clarity, the shutter 136 is illustrated as being transparent in FIG. 5, although one skilled in the art will appreciate that the shutter's opacity can vary without departing from the present invention's scope. FIG. 6 is an exploded perspective view of the components illustrated in FIG. 5. FIG. 7 illustrates a barrel plunger 152, FIG. 8 illustrates an outer-telescoping member 146, and FIG. 9 illustrates a needle actuation plunger 166. Optionally, the power pack 1380 also includes the frame 138.

As shown most clearly in FIG. 6, the shutter 136 includes a substantially U-shaped arm cutout 140 and a through arm slot 142 to slidingly accommodate sliding arms 144 of the outer telescoping member 146. The shutter 136 also has a barrel plunger cutout 148 with a notch 149 at a top thereof, and a barrel plunger engaging surface 150 to engage the barrel plunger 152, as subsequently described in greater detail. The shutter 136 additionally has a horizontally oriented latch slot 154 for selectively engaging the shutter latch 156. Further, the shutter 136 includes a biasing arm 158 and a needle actuation cutout 160 defining first and second engaging surfaces 162 and 164 for engagement with the needle actuation plunger 166, as will also be subsequently described in greater detail. The biasing arm 158 biases the shutter 136 toward the barrel side of the device 100.

As shown in FIG. 5, in the pre-activated stage, the barrel plunger 152 is disposed within the outer telescoping member 146 and engages the barrel plunger engaging surface 150 of the shutter 136 at a barrel shutter-engaging structure 168 (best shown in FIG. 6). According to one embodiment, the barrel shutter-engaging structure 168 is defined by a pair of cutouts with a bridge structure 169 disposed therebetween that engages the notch 149 of the shutter 136 in the pre-activated stage. The barrel plunger 152 also includes a stopper seat 170 on which a stopper 172 is disposed (see, for example, FIG. 21), and a pair of cantilevered plunger arms 174. A pair of plunger hooks 176 is respectively disposed at the free ends of the cantilevered plunger arms 174, as shown in FIG. 7.

At a first end thereof, a barrel spring 178 engages the frame 138. The barrel spring 178 is disposed in an annular cavity 177 of the barrel plunger 152 (see FIG. 7), and at its second end, the barrel spring 178 engages the interior of the barrel plunger 152. Accordingly, the barrel spring 178 biases the barrel plunger 152 toward the second end of the main body 106.

As shown in FIGS. 5, 6 and 8, the outer telescoping member 146 has a pair of sliding arms 144 extending from the first end thereof, and also has a pair of teeth 180 extending from the second end that engage with corresponding engagement slots 182 in the barrel plunger 152. In addition, a cantilevered arm 181 and a foot 183 form a stabilizing feature that is slightly depressed or deflected radially inward during assembly to prevent the outer telescope member 146 and elements connected thereto from rocking. In the pre-activated stage, the sliding arms 144 slidably engage the arm slot 142 and arm cutout 140 of the shutter 136. As subsequently described in greater detail, and as best shown in FIG. 8, the outer telescoping member 146 additionally has a stopped groove 182 in which the barrel plunger's plunger hooks 176 are slidably disposed. In other words, the groove 182 does not run the entire axial length of the interior of the outer telescoping member 146.

As shown in FIGS. 5, 6, and 9, the needle actuation plunger 166 has a second engaging structure 186 at a first end thereof, for engaging the second engaging surface 164 of the shutter 136 during the first activation stage. According to one embodiment, the second engaging structure 186 is a foot extending from the needle actuation plunger 166. At the opposing, second end of the needle actuation plunger 166, there is a protrusion 188 and a flange 190 that has a spring-engaging surface 192 and a slider-engaging surface 194. As subsequently described in greater detail (and illustrated in FIG. 20), the protrusion 188 and the slider-engaging surface 194 engage and position a needle actuation slider 196.

The needle actuation plunger 166 also has a cylindrical portion 198 for supporting a needle actuation spring 200, and a first engaging structure 202 for engaging the first engaging surface 162 of the shutter 136 during the pre-activation stage. As shown in FIGS. 5, 6, and 9, the first engaging structure 202 in one embodiment is a transverse groove in the needle actuation plunger 166. According to one embodiment, at least one side of the transverse groove is inclined or sloped. The needle actuation spring 200 engages the frame 138 at a first end of the spring, and engages the spring-engaging surface 192 of the flange 190 at a second end of the spring.

Figure 10:
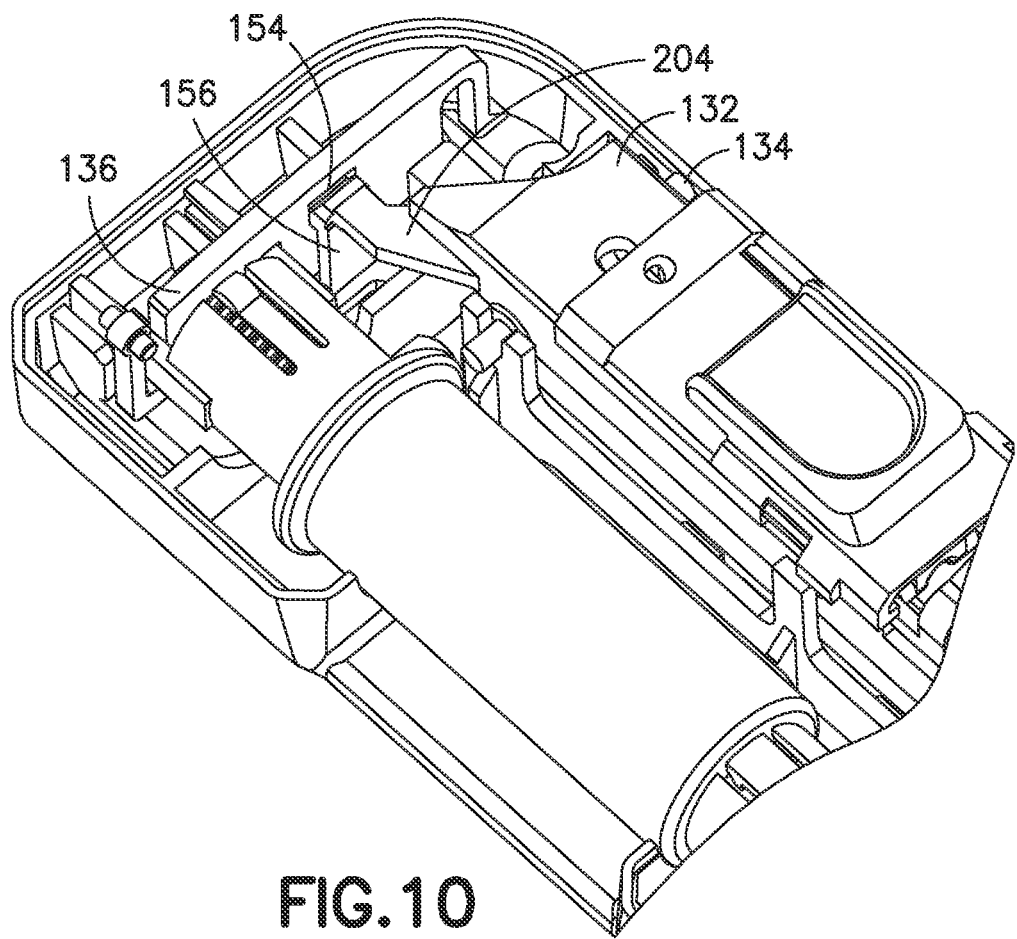
FIG. 10 is a partial perspective view of the device of FIG. 1.

According to one embodiment, the shutter latch 156 is rotatably disposed on the bottom cover 104, and has a hook 184 for selectively engaging the latch slot 154 in the shutter 136. As noted previously, during the pre-activated stage, the hook 184 of the shutter latch 156 is engaged with the latch slot 154. In addition, as shown in FIG. 10, a blocking arm 204 of the lever 132 engages the shutter latch 156 and prevents it from rotating, thereby maintaining the hook 184 in engagement with the latch slot 154, and thus preventing the shutter 136 from moving. According to one embodiment, the shutter latch is biased away from the shutter 136, for example, by a spring (not shown).

FIG. 11 is a bottom perspective view of the lever 132, which includes the previously described laterally-extending pivots 134 and blocking arm 204, and also includes a loading element 218 that biases the needle arm 130 during operation of the device 100. The lever pivots 134 movably engage a corresponding pair of lever pivot mounts 135 (see FIG. 4) in the bottom cover 102.

As shown in FIG. 12, the needle arm 130 includes a pair of detents or wings 210 extending laterally from a first end, and a pair of pivots 212 extending laterally from a second end. The pivots 212 movably engage a corresponding pair of arm pivot mounts 213 (see FIG. 4) in the bottom cover 102. A port 238 is mounted to the first end of the needle arm 130, and the patient needle 124 extends from the needle hub or port 238. According to one embodiment, the patient needle 124 is hollow with a sharpened distal end, is made of surgical stainless steel, has a gauge of 29, and has an overall length of 11.5 mm for a subcutaneous penetration of about 4-6 mm. One skilled in the art will appreciate that the material, gauge, end-treatment, and length of the patient needle 124 can vary without departing from the scope of the present invention. For example, the length and gauge of the patient needle can be optimized for subcutaneous infusion, or for intradermal infusion. A connecting tube 228 (see, for example, FIG. 27) connects a valve plate 232 and the port 238 to form part of the medicament flow path.

Figure 13:
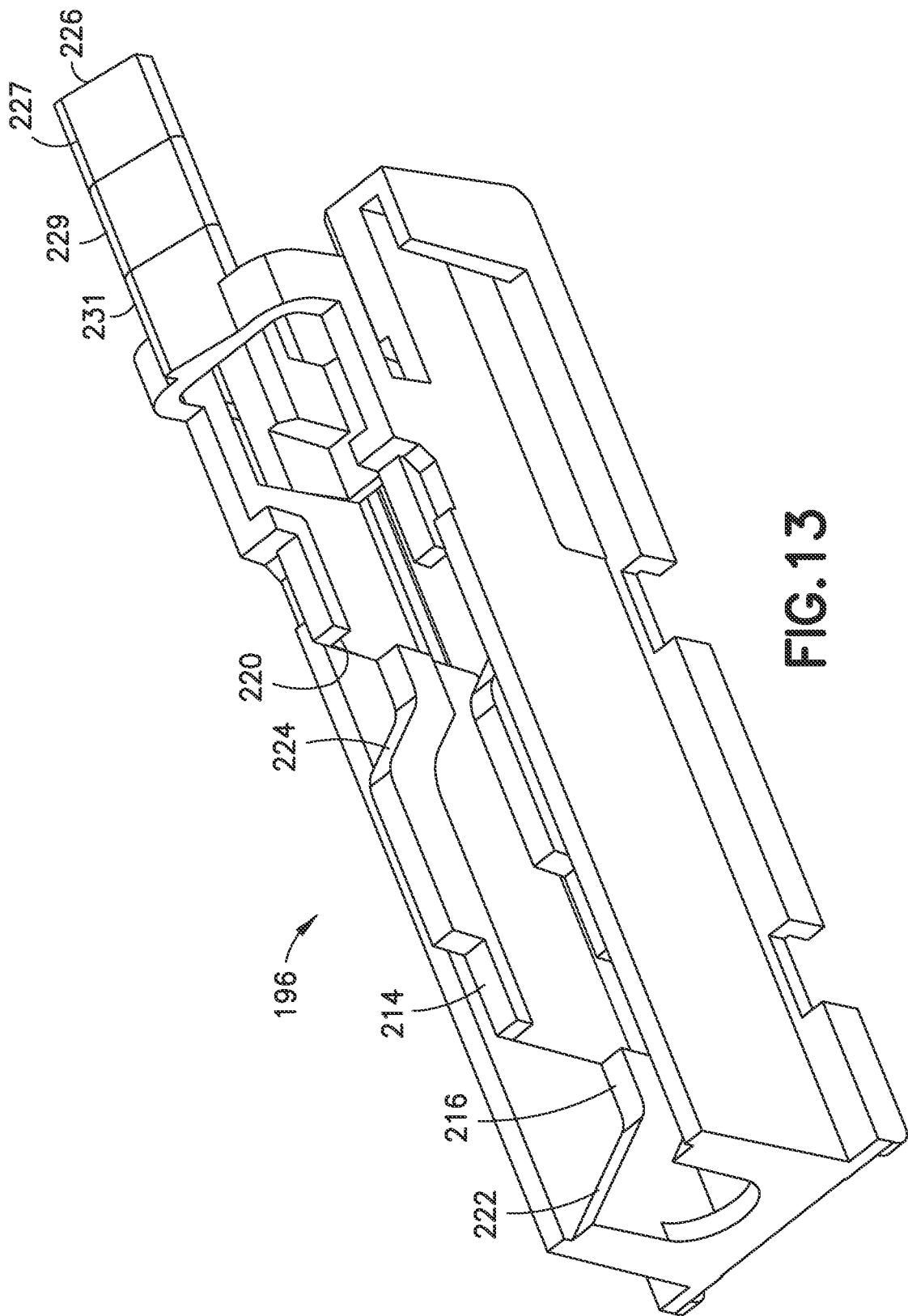
FIG. 13 is a perspective view of a needle actuation slider of the device of FIG. 1.

Turning to FIG. 13, the needle actuator or slider 196 has a pair of loading cliffs 214, a pair of depth stops 216, a pair of needle-retracting ramps 222, a pair of pivot ramps 224, and a pair of pivot ledges 220. As subsequently described in greater detail, during operation of the device 100, the slider 196 moves toward the second end of the device 100, and thereby controls the movement of several of the components of the device 100. For example, the wings 210 of the flexible needle arm 130 are disposed on the loading cliffs 214 during the pre-activated stage. During the first activation stage, as subsequently described in greater detail, due to the displacement of the slider 196, the wings 210 slide off the loading cliffs 214 and contact the depth stops 216, which limit the insertion depth of the patient needle 124. Also, the loading element 218 of the lever 132 (shown in FIG. 11) is positioned beneath the pivot ledges 220, thereby preventing the lever 132 and the button 110 from lifting during the first activation stage. Further, during the second activation stage, the needle 124 is retracted into the device 100 because the wings 210 ride along the needle-retracting ramps 222, and the button 110 is lifted because the loading element 218 is lifted by the pivot ramps 224 as the slider 196 travels farther forward. The angle of the needle-retracting ramps can be varied to effect the desired timing or speed of the needle withdrawal without departing from the present invention's scope.

The slider 196 also includes a stage-indicating structure 226 with areas 227, 229, and 231 for indicating the pre-activated stage, first activation stage, and second activation stage, respectively, though the status viewport 112. As noted previously, each of these areas can have a different color, number, letter, word, phrase, combination of these indicators, or some other indicator to represent the different stages of operation of the device 100. According to one embodiment, as shown in FIG. 13, the face of the stage-indicating structure 226 that houses the areas 227, 229, and 231 is disposed at an angle to match the viewport 112, and to thereby be more readily visible through the viewport 112.

Figure 14:
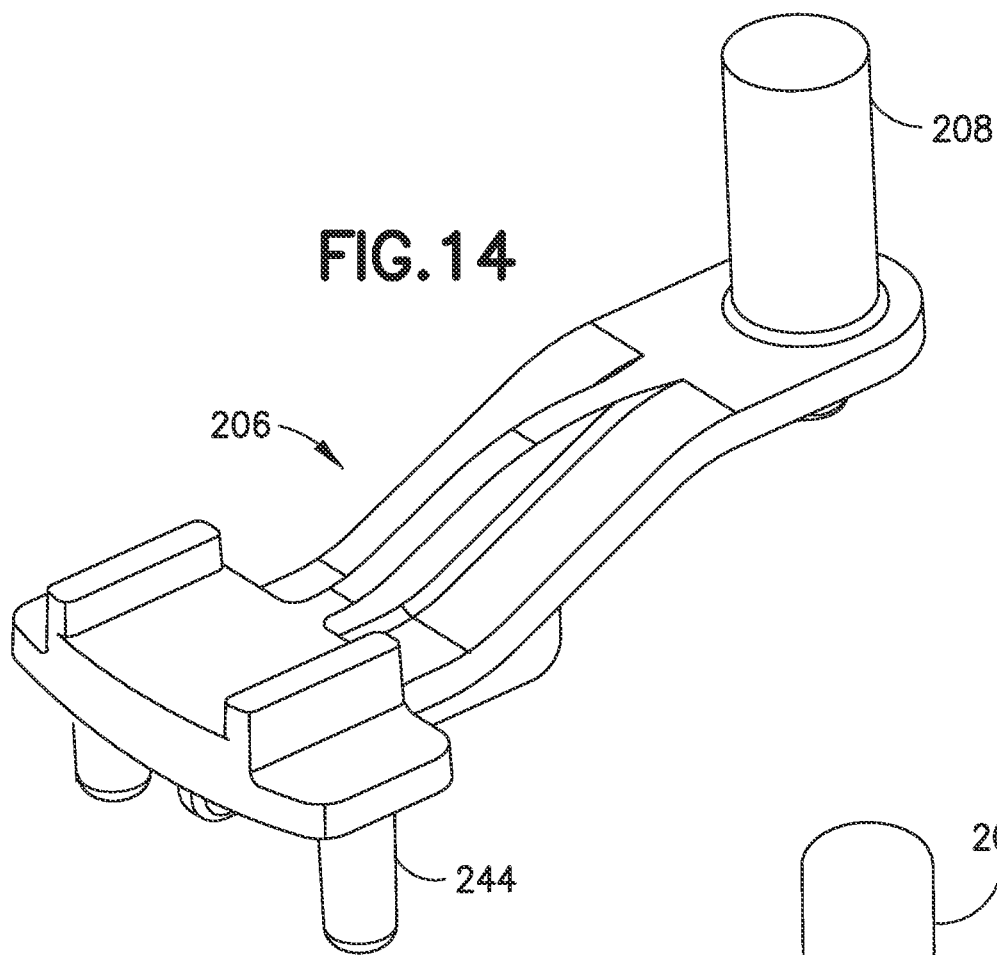
FIGS. 14 and 15 are respective top and bottom perspective views of a switch arm of the device of FIG. 1.
Figure 15:
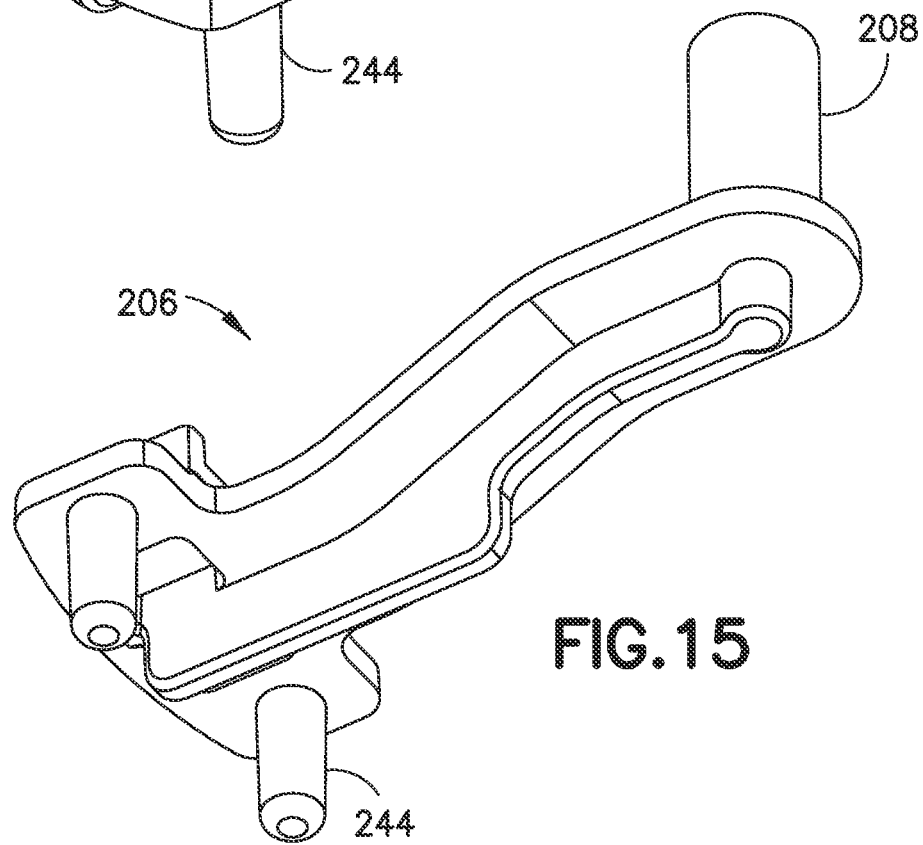
Figure 16:
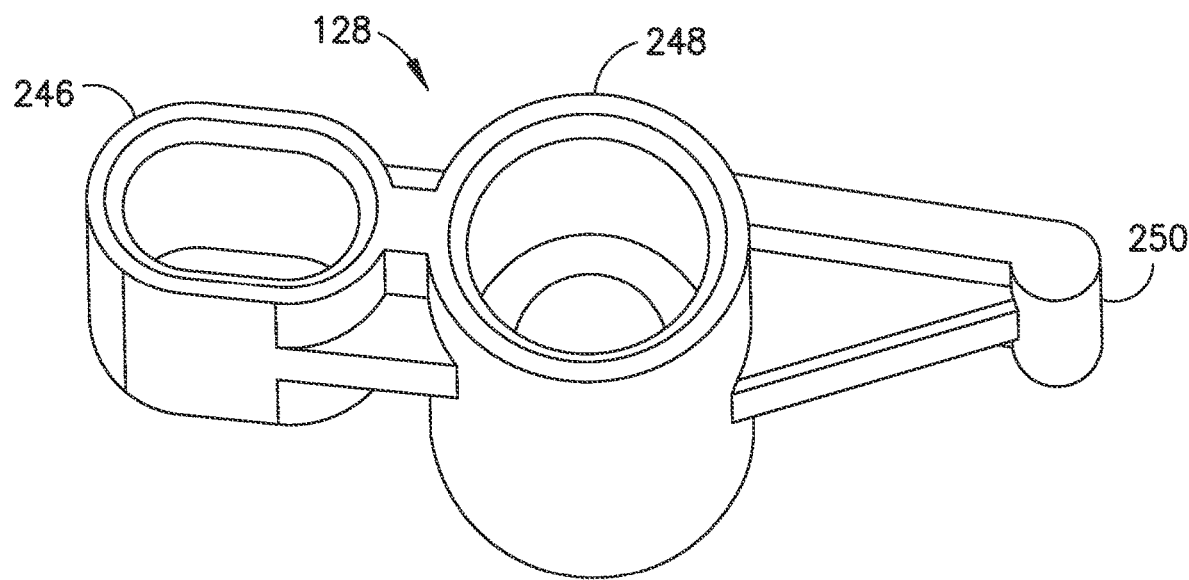
FIG. 16 is a perspective view of a rocker of the device of FIG. 1.

The second end of the slider 196 contacts a switch arm 206, which is shown in FIGS. 14 and 15. The switch arm 206 has a pair of leg posts extending from a bottom thereof, and has a rocker post 208 extending from a top thereof to engage a switch collar 246 of the rocker 128, which is illustrated in FIG. 16. A central portion 248 of the rocker 128 pivots about a post on the bottom cover 104, and a plate-engaging structure 250 is disposed on the opposite end of the rocker 128 from the switch collar 246. One skilled in the art will appreciate that dimensions of the rocker 128, for example, the distance between the switch collar 246 and the central portion 248, or the distance between the central portion 248 and the plate-engaging structure 250 can be modified without departing from the present invention's scope to provide a desired mechanical advantage to the rocker. For example, the ratio of the force input to the rocker relative to the force output of the rocker 128 is preferably from about 0.8:1.0 to 1.0:1.0. As the ratio increases, the force required from the needle actuation spring 200 to open the valve is reduced.

Figure 17:
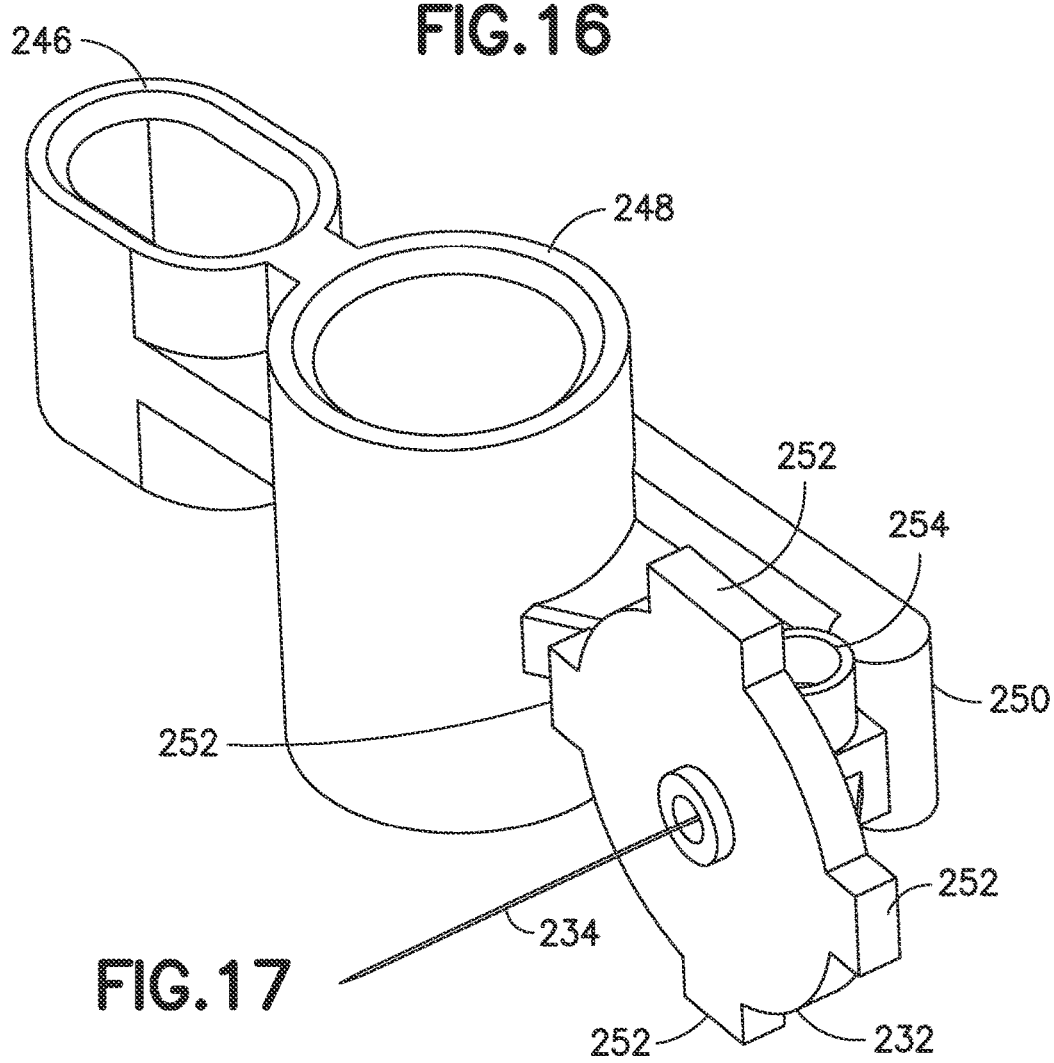
FIG. 17 is a perspective view of the rocker of FIG. 16 and a valve plate of the device of FIG. 1.

As shown in FIG. 17, the plate-engaging structure 250 engages the valve plate 232. According to one embodiment, the valve plate 232 is movably connected with the plate-engaging structure 250. Preferably, however, the plate-engaging structure 250 simply contacts the valve plate 232. The valve plate 232 includes a plurality of guiding wings 252 that maintain the orientation of the valve plate relative to the valve cover 126 during movement of the valve plate 232. The valve plate 232 also includes a valve port 254 fluidly connected to a hollow valve needle 234. The connecting tube 228 or tubing 228 connects the valve port 254 to the port 238 disposed on the end of the needle arm 130. For clarity, the connecting tube 228 is omitted from the majority of the drawings, but is shown, for example, in FIG. 27.

Figure 18:
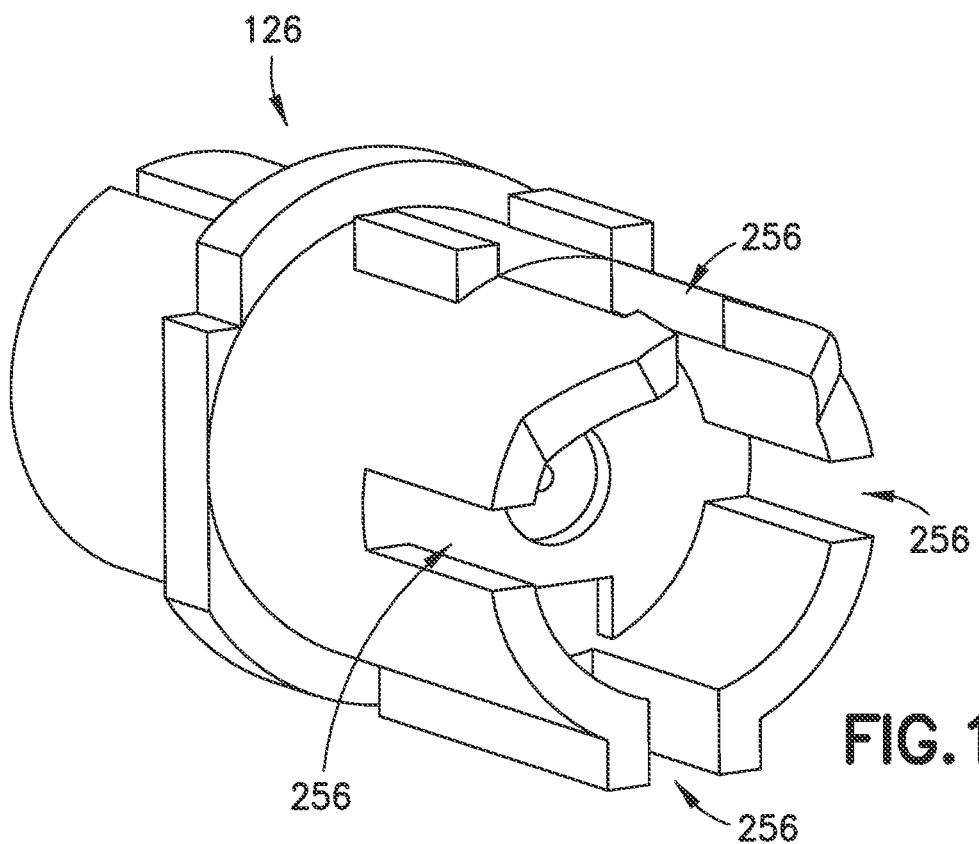
FIG. 18 is a perspective view of one side of a valve cover of the device of FIG. 1.
Figure 19:
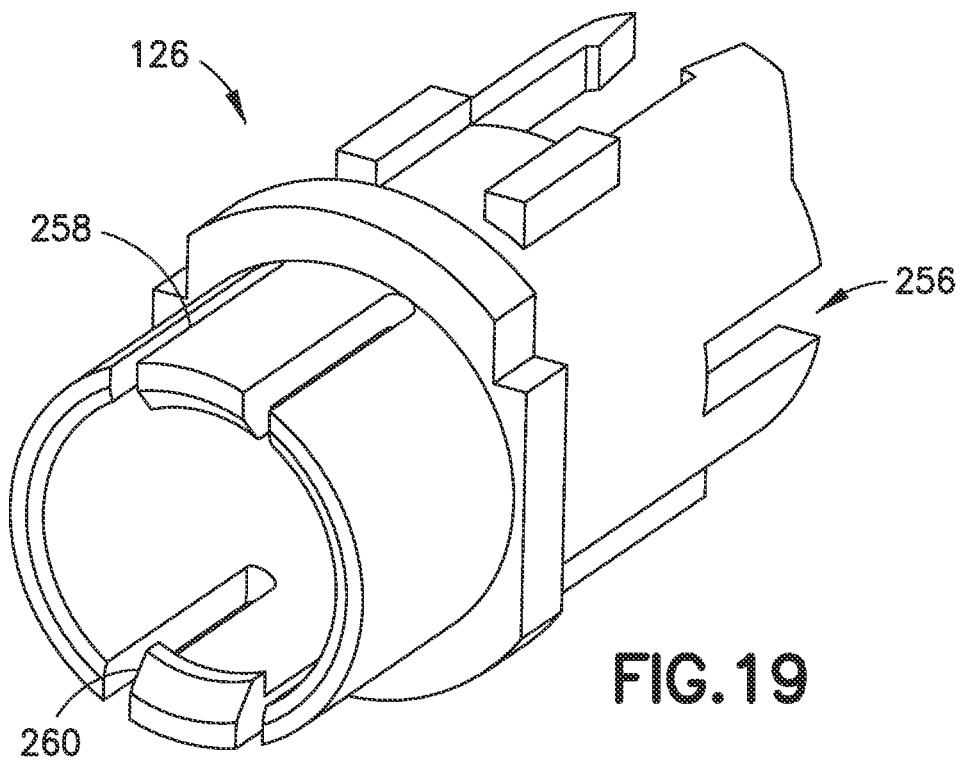
FIG. 19 is a perspective view of another side of the valve cover of FIG. 18.

As shown in FIG. 18, the valve cover 126 has a plurality of slots 256 corresponding to the guiding wings 252 of the valve plate 232. The slots 256 guide the guiding wings 252 during displacement of the valve plate 232 relative to the valve cover 126. The opposing side of the valve cover 126 includes a pair of cantilevered arms 258 with hooks 260 disposed at the free end thereof, as shown in FIG. 19, for securing the syringe barrel 108 with the valve cover 126.

Figure 20:
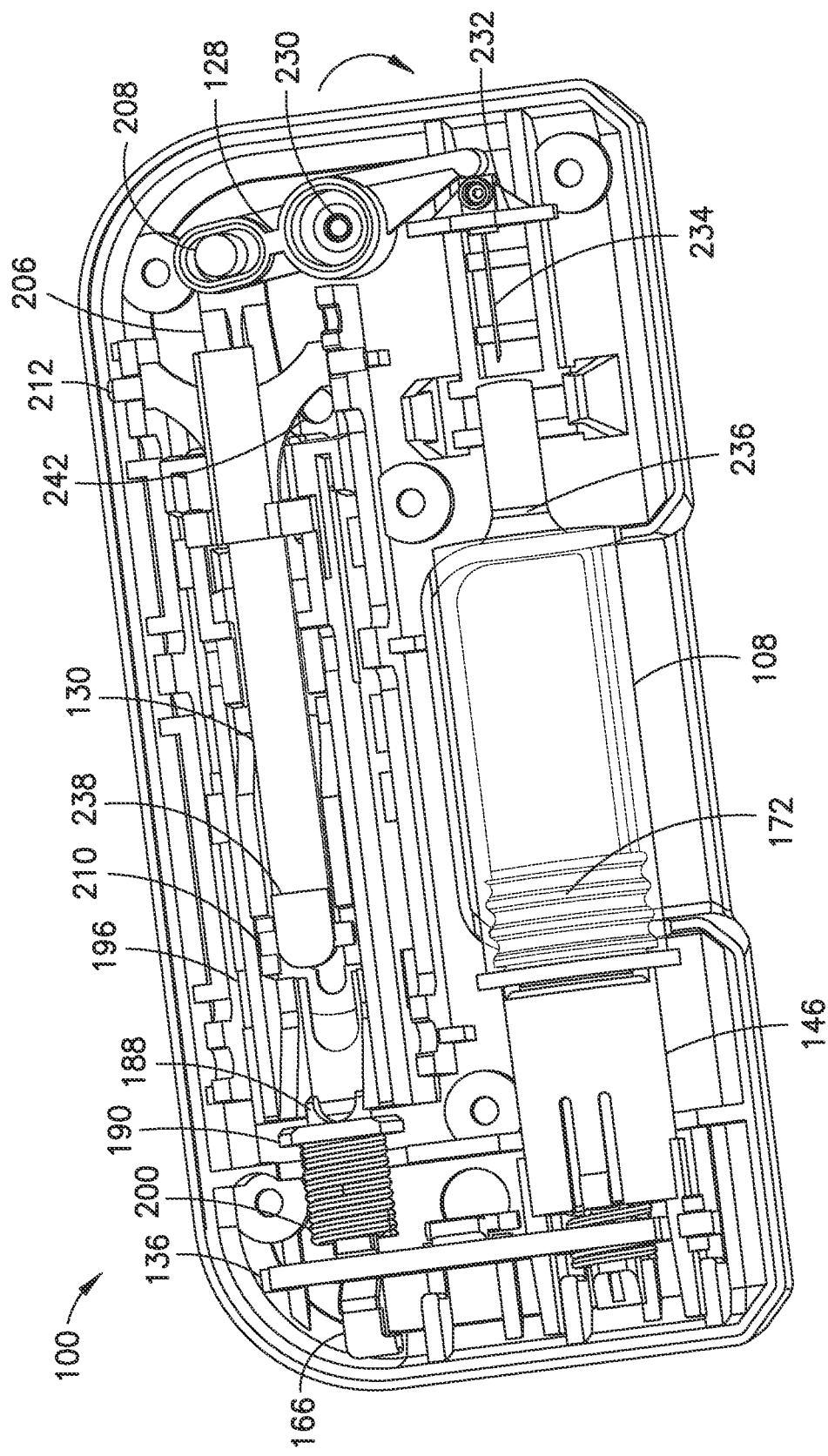
FIG. 20 is a perspective view of the device of FIG. 1 in the pre-activated stage, with several elements removed for clarity.

FIG. 20 is a perspective view of the device 100 in the pre-activated stage, with several elements removed for illustrative purposes. The protrusion 188 and the slider-engaging surface 194 of the needle actuation plunger 166 engage the slider 196 at the first end thereof. At the second end, the slider 196 engages the movable switch arm 206, the post 208 of which engages the rocker 128. The detents or wings 210 of the needle arm 130 are disposed on the loading cliffs 214 of the slider 196.

After removing the adhesive liner, the user secures the device 100 to the user's skin. To activate the device 100 and enter the first activation stage (shown in FIGS. 21 and 22), the user slides the button 110 forward, and at the end of the forward motion, pushes button 110 down. According to one embodiment, to the user, this feels like a single motion. For example, it can feel like sliding the button 110 on a ramp with a flat (horizontal) portion at the top of the ramp. The downward push of the button 110 rotates the lever 132 about the pivots 134. This lever rotation moves the loading element 218 down to deflect a middle portion of the flexible needle arm 130, thereby loading the needle arm 130. In other words, the deflection of the middle portion of the needle arm 130 biases the first end of the needle arm 130 (and thereby, the patient needle 124) to rotate down. Because the wings 210 are still resting on the loading cliffs 214, however, the patient needle 124 is maintained within the device 100.

Once the lever 132 rotates, the blocking arm 204 no longer prevents movement of the shutter latch 156. And once the shutter latch 156 is permitted to move, because the needle actuation plunger 166 is biased by the spring 178 toward the second end of the main body 106, the needle actuation plunger 166 moves and the sloped side of the first engaging structure 202 of the needle actuation plunger 166 displaces the shutter 136 upward. This frees the needle actuation plunger 166 and the barrel plunger 152 to move longitudinally forward toward the second end of the main body 106 under the force of their respective springs 178 and 200. The needle actuation plunger 166 moves forward until the second engaging structure 186 contacts the second engaging surface 164 of the shutter 136. The spring 200 continues to move the plunger 166 forward. Although the timing of events can be varied without departing from the present invention's scope, it is preferable that the loading element 218 biases the patient needle prior to the initial forward movement of the needle actuation plunger 166.

The forward displacement of the needle actuation plunger 166 until the second engaging structure 186 contacts the second engagement surface 164 longitudinally displaces the slider 196 forward toward the second end of the main body 106. Briefly, this displacement of the slider 196 causes the patient needle 124 to extend outside of the main body 106 (into the skin of the patient) and causes a valve to open, thereby permitting the medicament to flow from the syringe barrel 108, through the tubing 228, and through the hollow patient needle 124.

Figure 22:
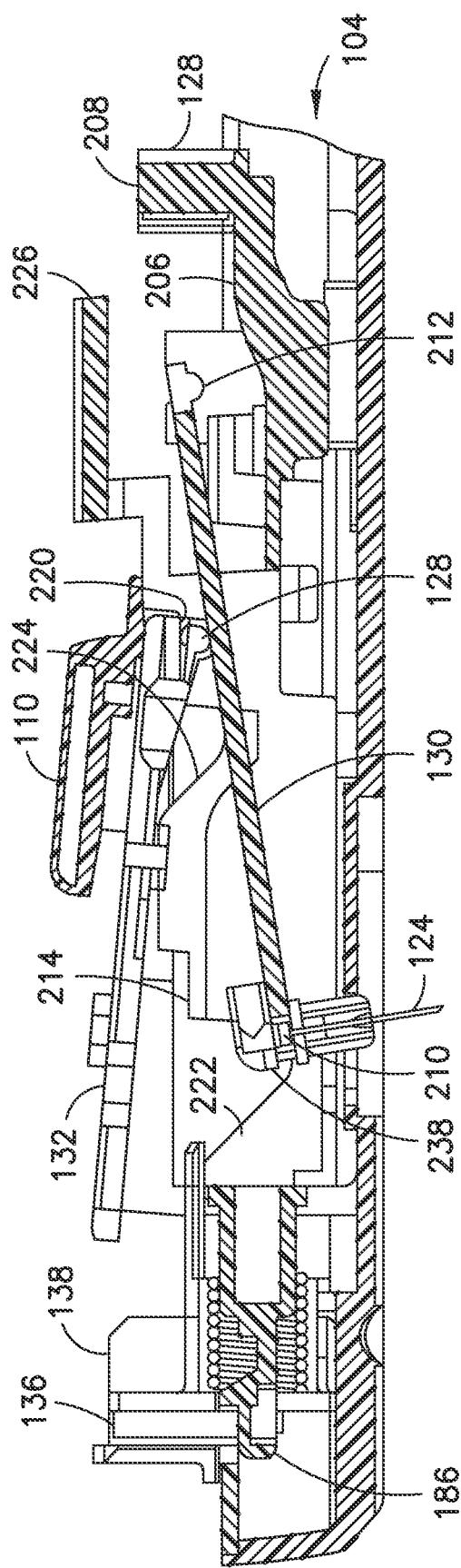
FIG. 22 is a cross-sectional view of the device of FIG. 1 in the first activation stage with the top cover removed.

In more detail, as the slider 196 moves forward under the force of the spring 200, via the plunger 166, the end of the loading cliff 214 reaches the wings 210, and because of the bias induced by the loading element 218, the patient needle quickly rotates down to extend outside of the main body 106 and into skin of the patient, as shown in FIG. 22. The wings 210 contact the depth stop 216 to limit movement of the patient needle 124. Put another way, the insertion depth of the patient needle 124 is determined by the length of the patient needle 124 and the height of the depth stop 216.

Figure 21:
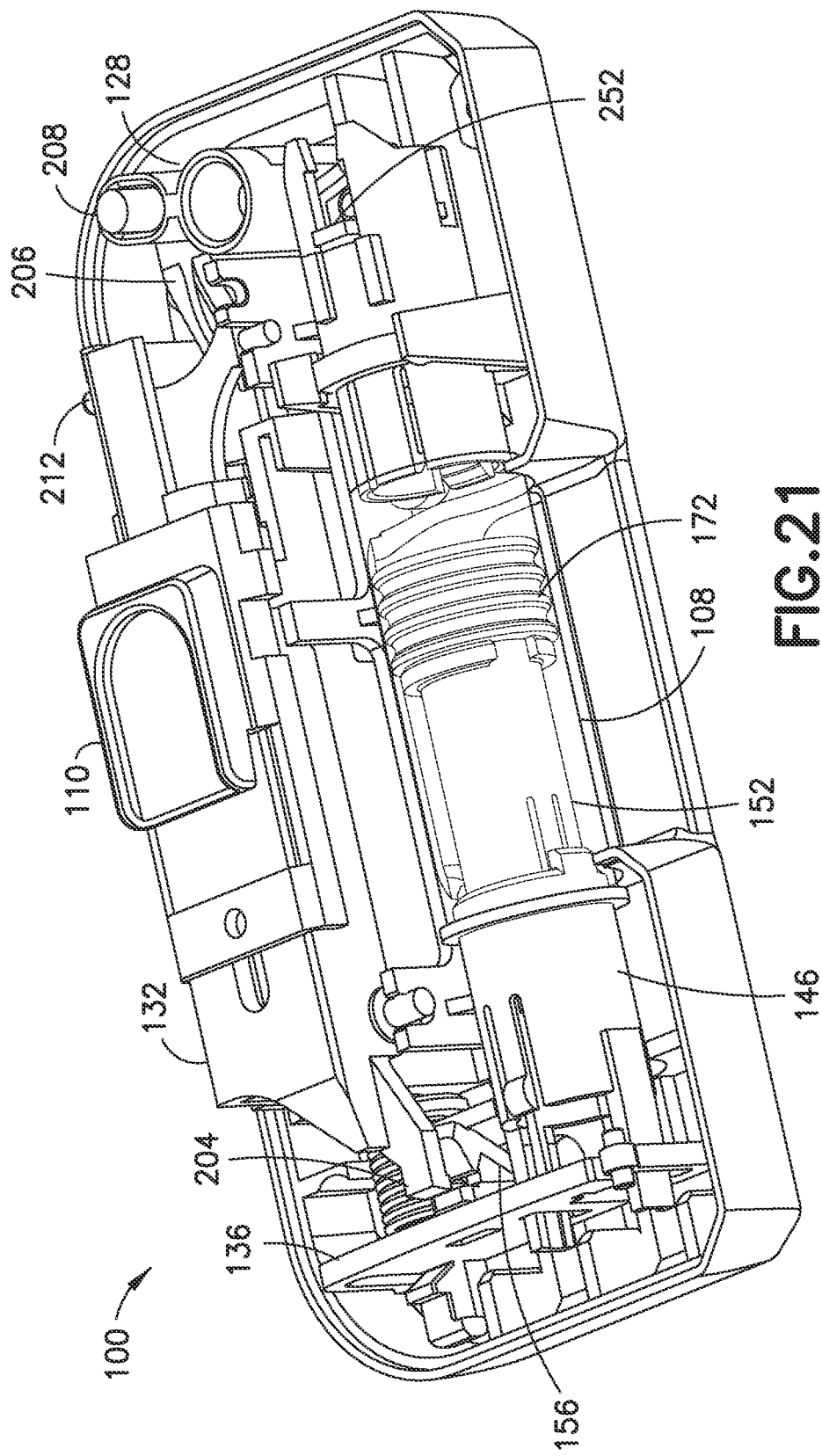
FIG. 21 is a top perspective view of the device of FIG. 1 in a first activation stage with the top cover removed.

In addition, as the slider 196 moves forward under the force of the spring 200, the pivot ledge 220 of the slider 196 moves over the loading element 218 of the lever 132, thereby preventing the lever 132 and the button 110 from moving upward, and maintaining the loading on the needle arm 130. The forward movement of the slider 196 also displaces the switch arm 206 forward. Because of the engagement of the post 208 with the rocker 128, as shown in FIG. 21, the forward motion of the switch arm 206 rotates the rocker 128 about a rocker pivot 230, thereby displacing the valve plate 232 toward the first end of the bottom cover 204.

According to one embodiment, the valve includes a valve septum 236 (see, for example, FIG. 31) disposed at the forward end of the syringe 108, and the valve needle 234 fixedly connected to the valve plate 232. According to one embodiment, the valve needle 234 is a Whitacre valve needle having a conical tip and a side port (see FIG. 31). The shape of the Whitacre valve needle 234 prevents coring of the valve septum 236. As the valve needle 234 is displaced by the motion of the rocker 128, the side port passes through the valve septum and communicates with the medicament in the syringe 108. The valve needle 234 communicates with the tubing 228, which is connected to the patient needle 124 at the port 238 on the needle arm 130. It will be understood by one skilled in the art that other valve mechanisms or valve assemblies can be used without departing from the present invention's scope. For example, although not shown, the valve needle can be fixed relative to the main body 106 and the valve septum can move to complete the fluid connection between the syringe 108 and the patient needle 124. Additionally, as subsequently described in greater detail, valve mechanisms or assemblies without a needle and septum can be employed.

Furthermore, as the slider 196 moves forward, the portion of the stage-indicating structure 226 visible through the status viewport 112 changes from the area 227 to the area 229, indicating the change from the pre-activation stage to the first activation stage. Also, as the slider 196 pushes the switch arm 206 forward, after a predetermined travel distance, the leg posts 244 of the switch arm 206 enter a floor recess 242 (best shown in FIG. 20) in the bottom cover 204 and the switch arm 206 drops down. As subsequently described in greater detail, this permits the second, or front end of the slider 196 to travel over a portion of the switch arm 206 during the second activation stage. This functionality permits a greater travel for the slider 196 within the confines of the main body 106. In other words, it allows the device 100 to be more compact.

Also during the first actuation stage, as previously noted, the barrel plunger 152 moves longitudinally forward toward the second end of the main body 106 under the force of the barrel spring 178, thereby moving the stopper 172 forward. This pressurizes the medicament in the syringe 108.

Preferably, although the release of the barrel plunger 152 and the needle activation plunger 166 from the shutter 136 is substantially simultaneous, their release and subsequent forward motions are independent. By changing the travel distance of the respective plungers or other elements, the timing of events can be determined. For example, according to one embodiment, it is preferable to pressurize the medicament prior to the opening of the valve.

As the barrel plunger 152 moves forward and pushes the medicament through the tubing 228 and patient needle 124 during the first activation stage, referring back to FIGS. 5 and 6, the barrel plunger hooks 176 engage the stopped ends of the stopped grooves 182. Continued forward motion of the barrel plunger 152 pulls the outer telescoping member 146 forward. Once the sliding arms 144 slide out of engagement with the shutter 136, the biasing arm 158 of the shutter 136 displaces the shutter 136 toward the barrel side of the bottom cover 104, thereby automatically initiating the second activation stage or end-of-dose stage. The length of the sliding arms can be varied to vary the timing of the end-of-dose stage initiation.

As the shutter 136 displaces toward the barrel side of the bottom cover 104, the second engaging surface 164 of the shutter 136 slides out of engagement with the second engagement structure or foot 186 of the needle actuation plunger 166. Because of the continued forward bias by the needle actuation spring 200, the needle actuation plunger 166 displaces further forward and drives the slider 196 further forward and over the rear portion of the switch arm 206. Briefly, this secondary forward movement of the slider 196 retracts the patient needle 124, rotates the lever 132 upward and raises the button 110, and makes the end-of-dose indicator 231 visible through the status viewport 212.

Figure 23:
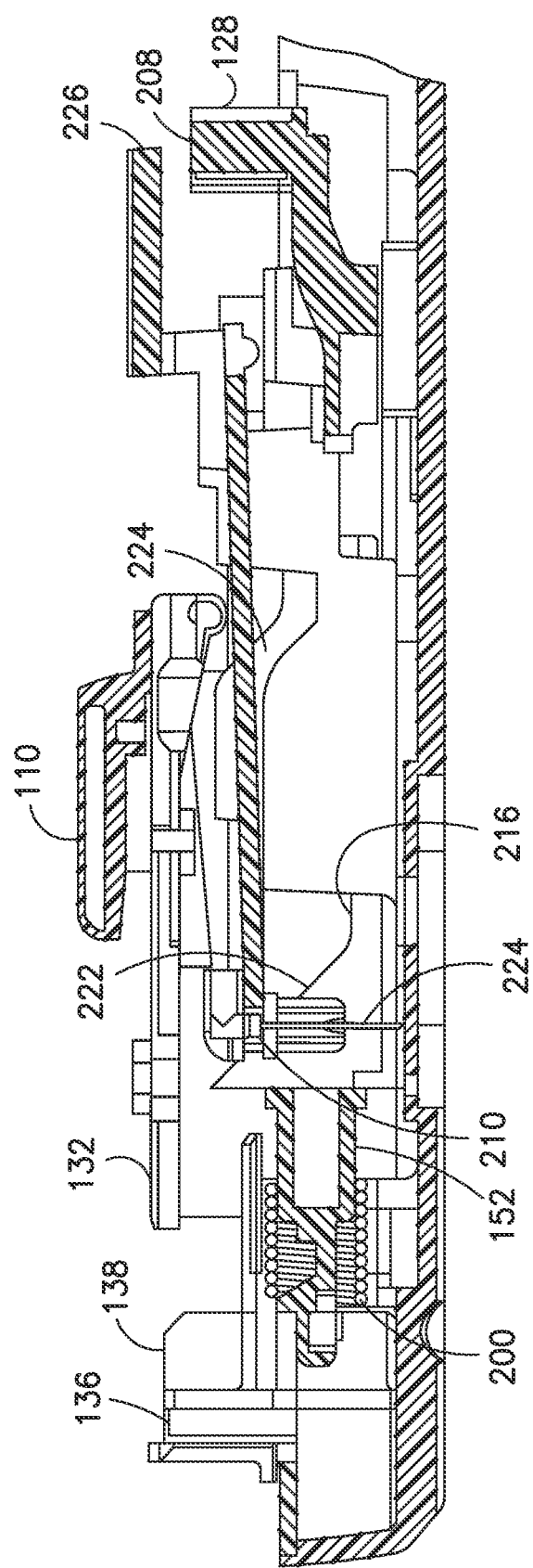
FIG. 23 is a cross-sectional view of the device of FIG. 1 in a second activation stage with the top cover removed.

In greater detail, as the slider 196 moves farther forward during the second activation stage, the needle-retracting ramps 222 of the slider 196 engage the wings 210, thereby retracting the patient needle 124 back into the main body 106. Similarly, with the additional forward motion of the slider 196, the pivot ramps 224 of the slider 196 engage the loading element 218 of the lever 132 and rotate the lever 132 back up about the pivot 134, thereby releasing the loading of the needle arm 130 and raising the button 110, as shown in FIG. 23.

Figure 24:
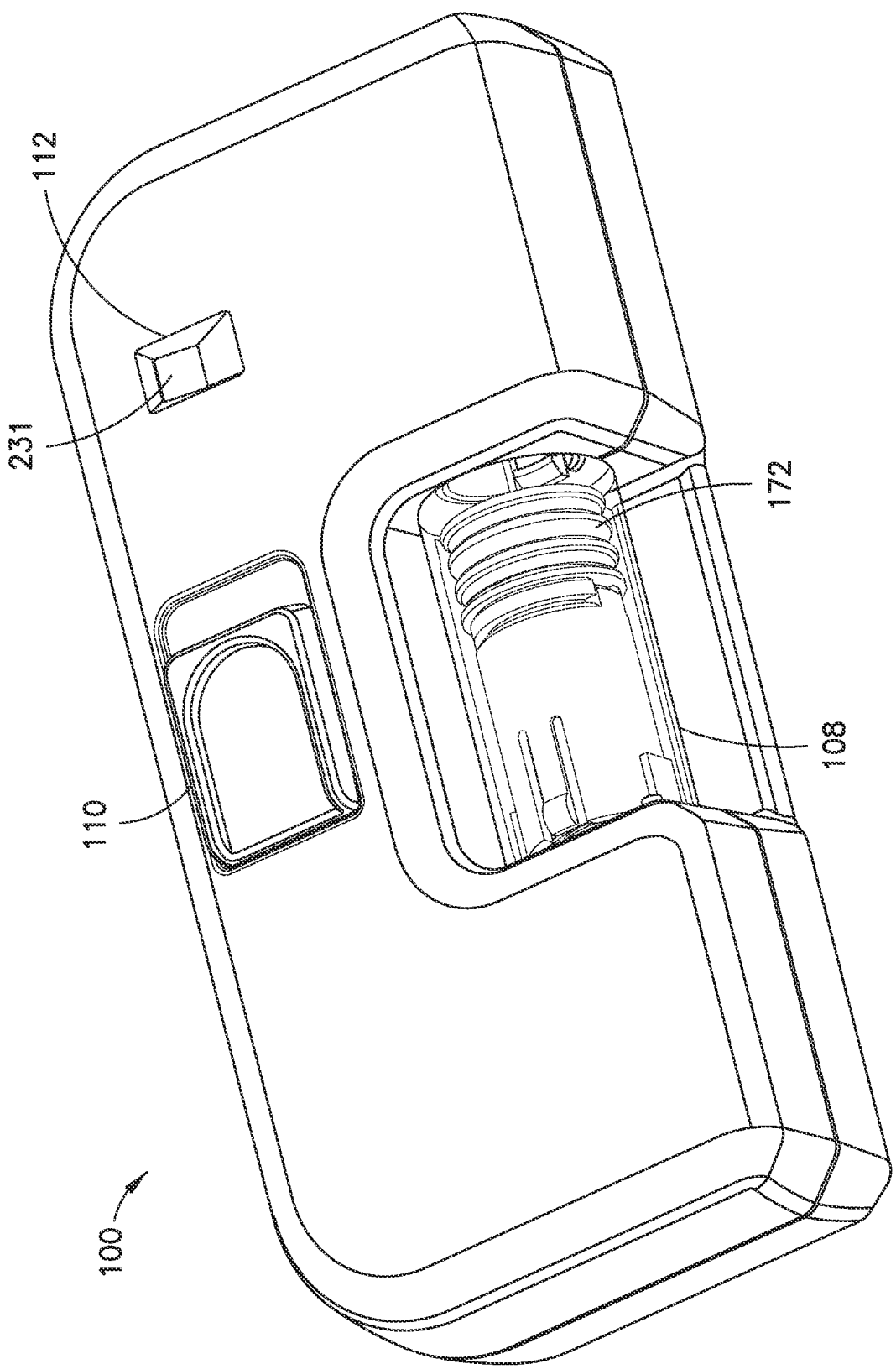
FIG. 24 is a top perspective view of the device of FIG. 1 in the second activation stage.

As shown in FIG. 24, with the secondary movement of the slider 196, the portion of the stage-indicating structure 226 visible through the status viewport 112 changes to the area 231, indicating the change from the first activation stage to the second activation stage (or end-of-dose stage). According to one embodiment, continued forward motion of the slider 196 is prevented by interference with the main body 106.

Once the end-of dose stage has been attained, the user can remove the device 100 from his or her skin and safely dispose of the device 100.

Figure 25:
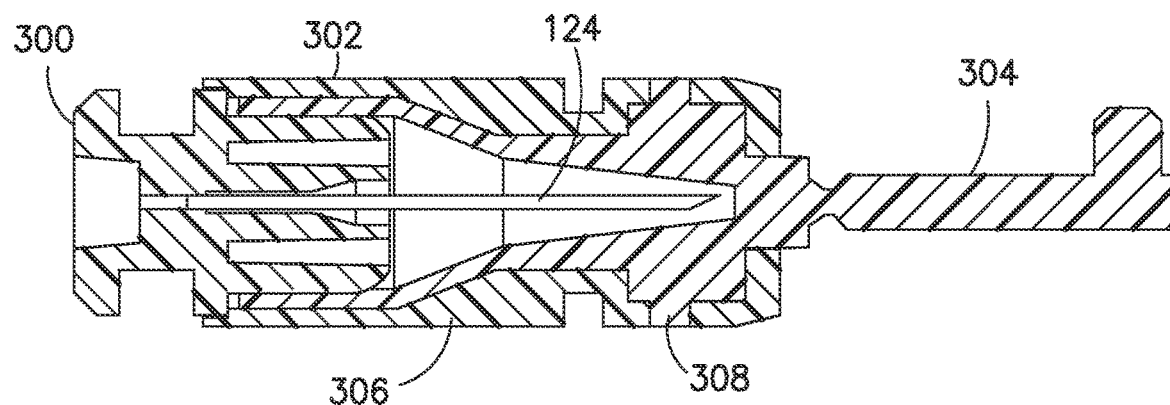
FIG. 25 is a cross sectional view of a port, a patient needle, and a needle cover portion in accordance with an embodiment of the present invention.
Figure 26:
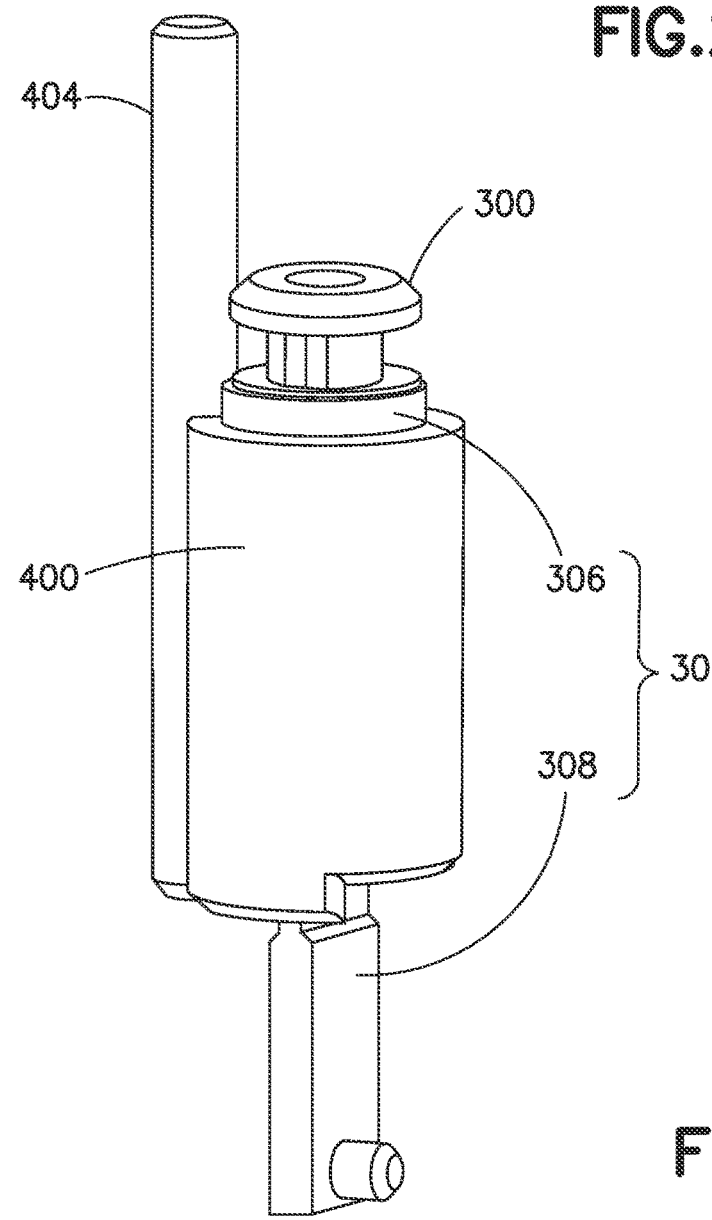
FIG. 26 is a top perspective view of the port and needle cover portion of FIG. 25 and a button lock portion in accordance with an embodiment of the present invention.

FIGS. 25 and 26 illustrate another embodiment of a needle cover 400. FIG. 25 is a cross sectional view of a port 300, the patient needle 124, and a needle cover portion 302 that includes a tab 304. One end of the tubing 228 connects to the valve plate 232 and the other end connects to the port 300. According to one embodiment, the needle cover 302 is manufactured in a two-shot molding process, with a first molding shot portion 306 and a second molding shot portion 308. As shown in FIG. 26, in combination with the needle cover portion 302, a button locking portion 402 forms the needle cover 400. The button lock portion 402 includes a safety extension 404 that engages the button or actuation button in a similar manner as the previously-described safety extension 120. As subsequently described in greater detail, this embodiment permits the needle cover portion 302 (along with the port, the patient needle, and other components of the fluid pathway) to be sterilized prior to assembly with the button lock portion 402. The button lock portion 402 and the needle cover portion 302 can be joined in several different ways, or a combination of ways, including snap-fit features, a friction fit, and an adhesive.

Figure 27:
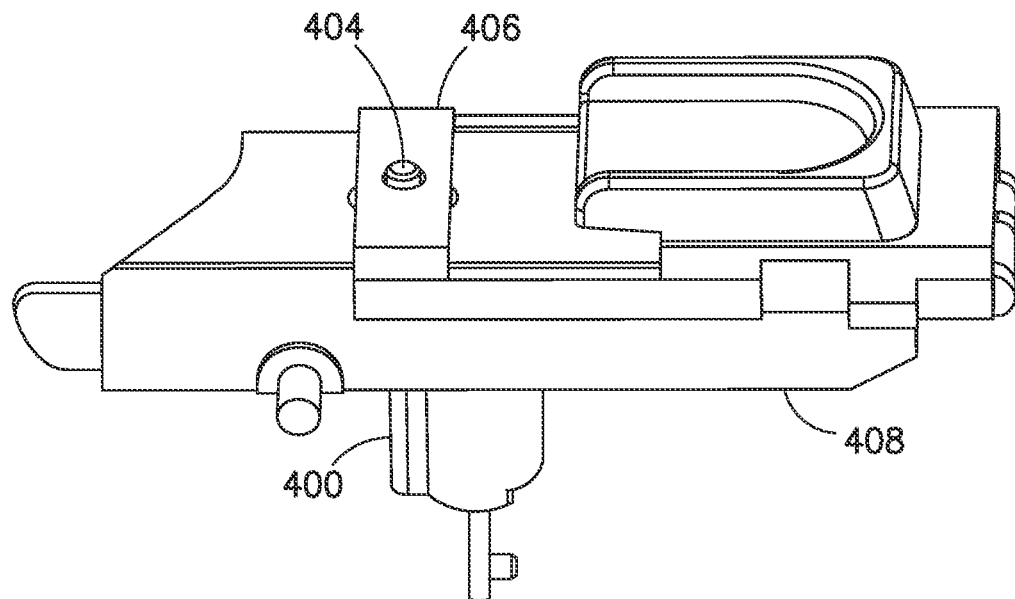
FIGS. 27 and 28 are top perspective views of a button retraction mechanism in accordance with an embodiment or the present invention.
Figure 28:
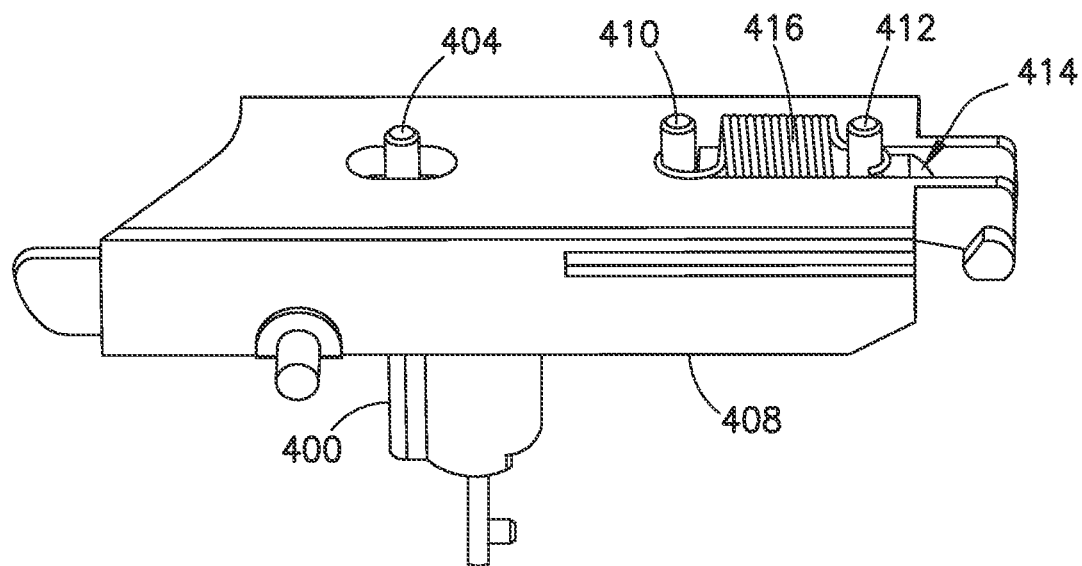

The medical device can include a feature for retracting the actuation button to an initial position if the button is displaced subsequent to the removal of the needle cover, but not sufficiently displaced to activate the device. For example, FIGS. 27 and 28 illustrate a mechanism for retracting the actuation button 406. A fixed pin 410 is fixedly disposed in the lever or lift lever 408 and a movable pin 412 is fixedly connected to the underside of the button 406, but permitted to move in a slot 414 in the lift lever 408. According to one embodiment, the pins 410 and 412 are held in place by friction, but other methods of securing the pins 410 and 412, such as an adhesive, can be employed without departing from the present invention's scope. A spring 416 connects the two pins 410 and 412. If the button 406 is displaced by a distance that is insufficient to activate the device and subsequently released, the spring 416 retracts the movable pin 412 (and thus, the button 406) to its initial position. For example, if the user does not apply sufficient force to the button 406 to activate the device and then releases it, the button 406 will return to its initial position. This feature can help prevent accidental actuation and aid device assembly.

Figure 29:
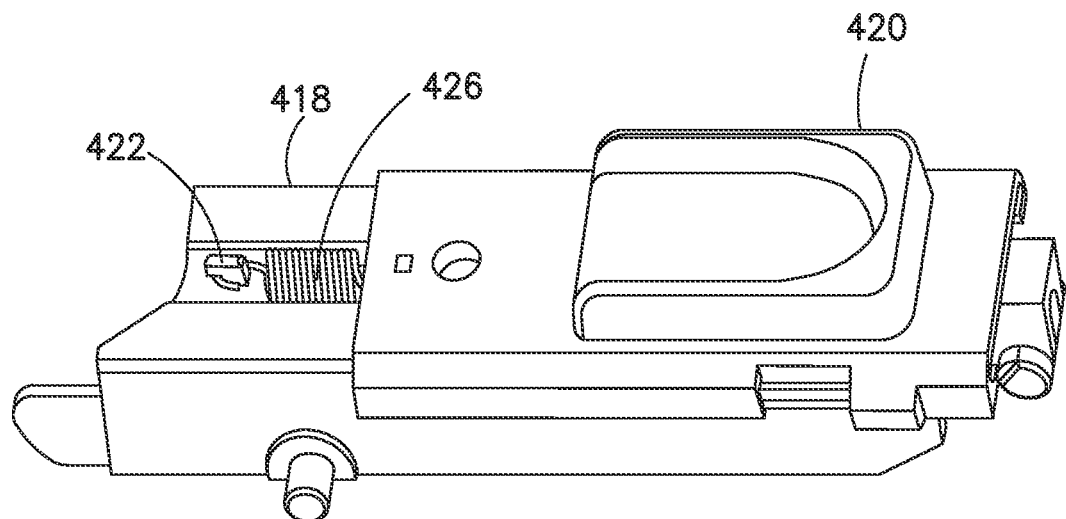
FIGS. 29-31 are respective top, top, and bottom perspective views of a button retraction mechanism in accordance with another embodiment or the present invention.
Figure 30:
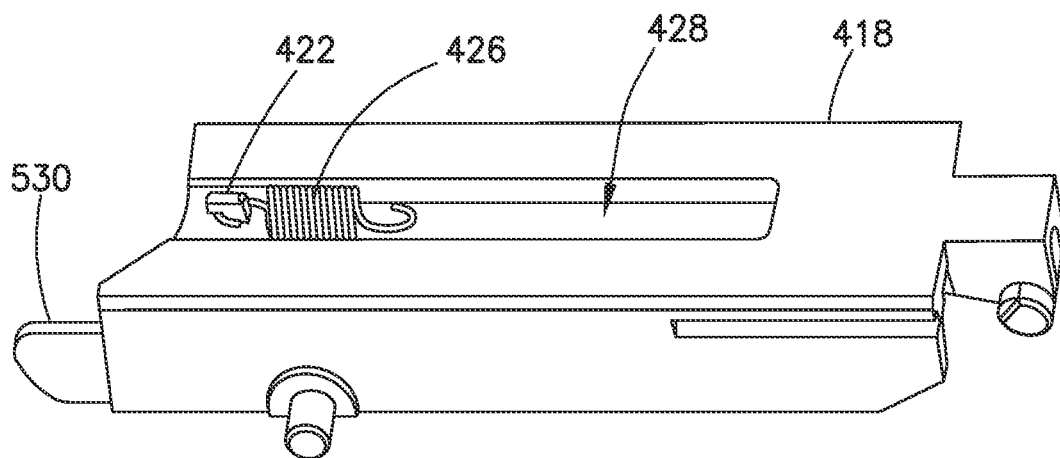
Figure 31:
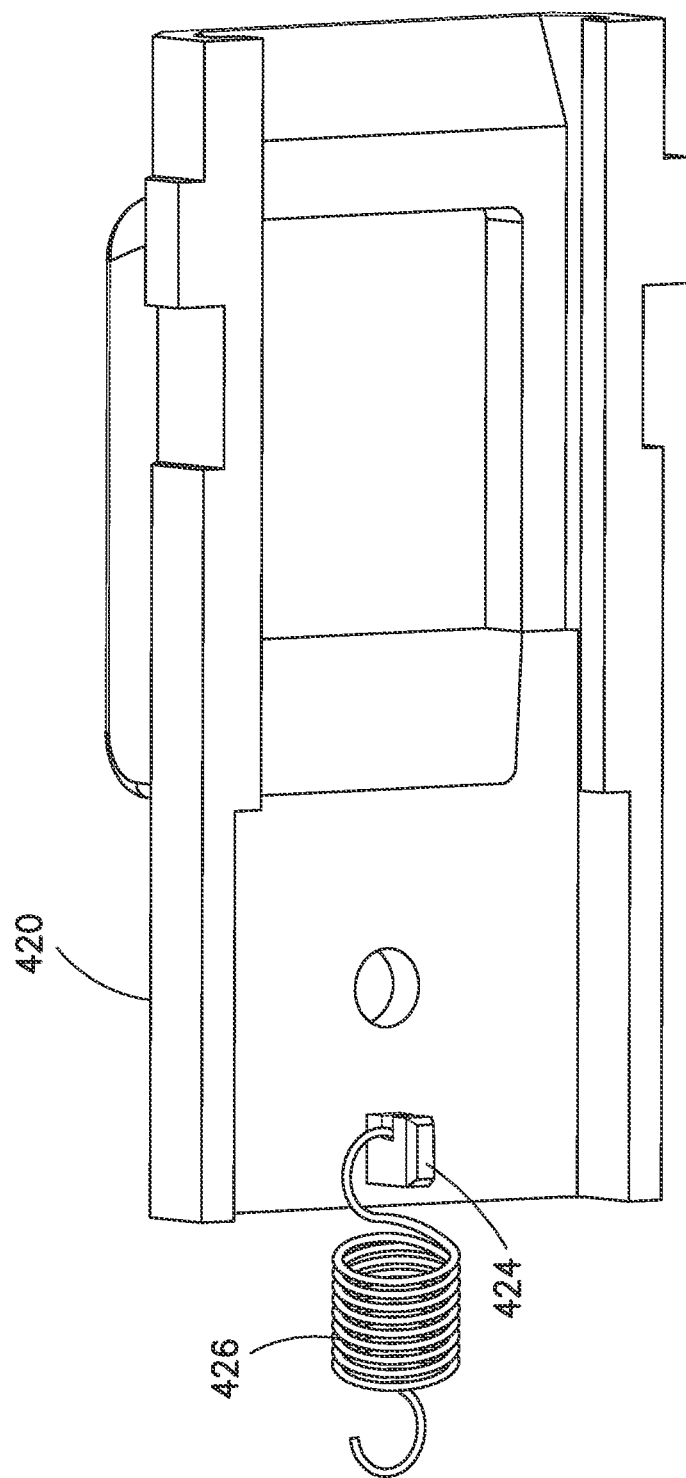

FIGS. 29-31 illustrate another embodiment to achieve the same goals. Rather than pins, both the lift lever 418 and the button 420 include hooks. More specifically, as shown in FIGS. 29 and 30, the lever 418 has a lever hook 422 disposed on a top thereof, and as shown in FIG. 31, the button 420 has a button hook 424 disposed on its bottom side. A spring 426 connects the two hooks 422 and 424. The button hook 424 travels in a slot 428 in the lever 420 when the button is displaced. Similar to the previously-described embodiment, subsequent to the removal of the needle cover, if the button 420 is displaced by a distance insufficient to activate the device and then released, the spring 426 retracts the button hook 424 (and thus, the button 420) to its initial position shown in FIG. 29. In addition, the slot 428 and the positioning of the lever hook 422 to the rear of the lever 418 provides additional clearance for the needle arm and port when the needle is retracted.

Figure 32:
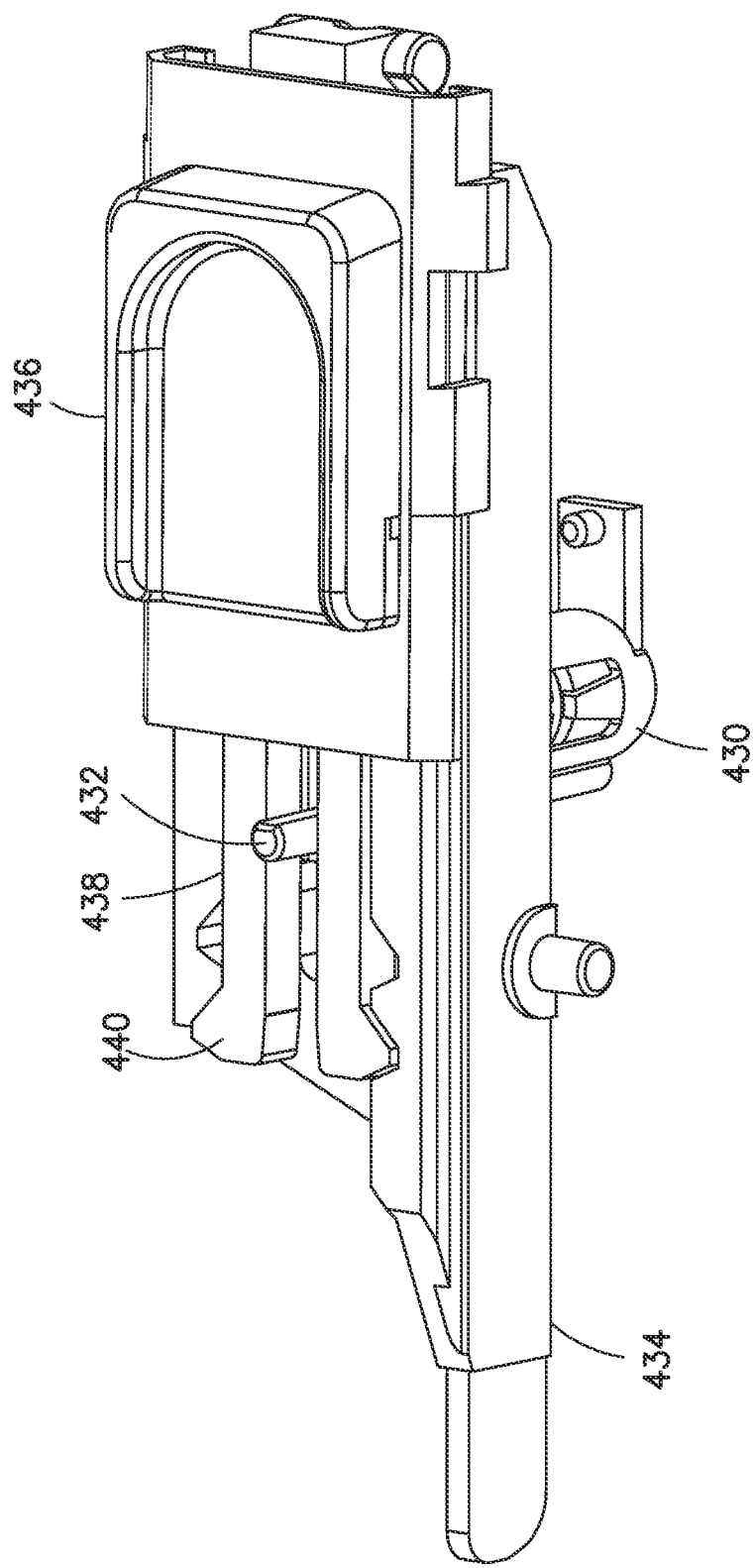
FIG. 32 is a top perspective view of a locking mechanism for selectively preventing activation of a drug delivery device in accordance with an embodiment of the present invention.

FIG. 32 is a perspective view of a locking mechanism for selectively preventing activation of a drug delivery device in accordance with an embodiment of the present invention. The mechanism includes a needle cover 430 with a safety extension 432, a lift lever 434, and an actuation button 436. The button 436 includes a pair of flexible, cantilevered snap arms 438 separated laterally by a distance substantially equal to a lateral dimension of the proximal end of the safety extension 432. A pair of angled locking protrusions 440 is respectively disposed at the free ends of the snap arms 438.

Figure 33:
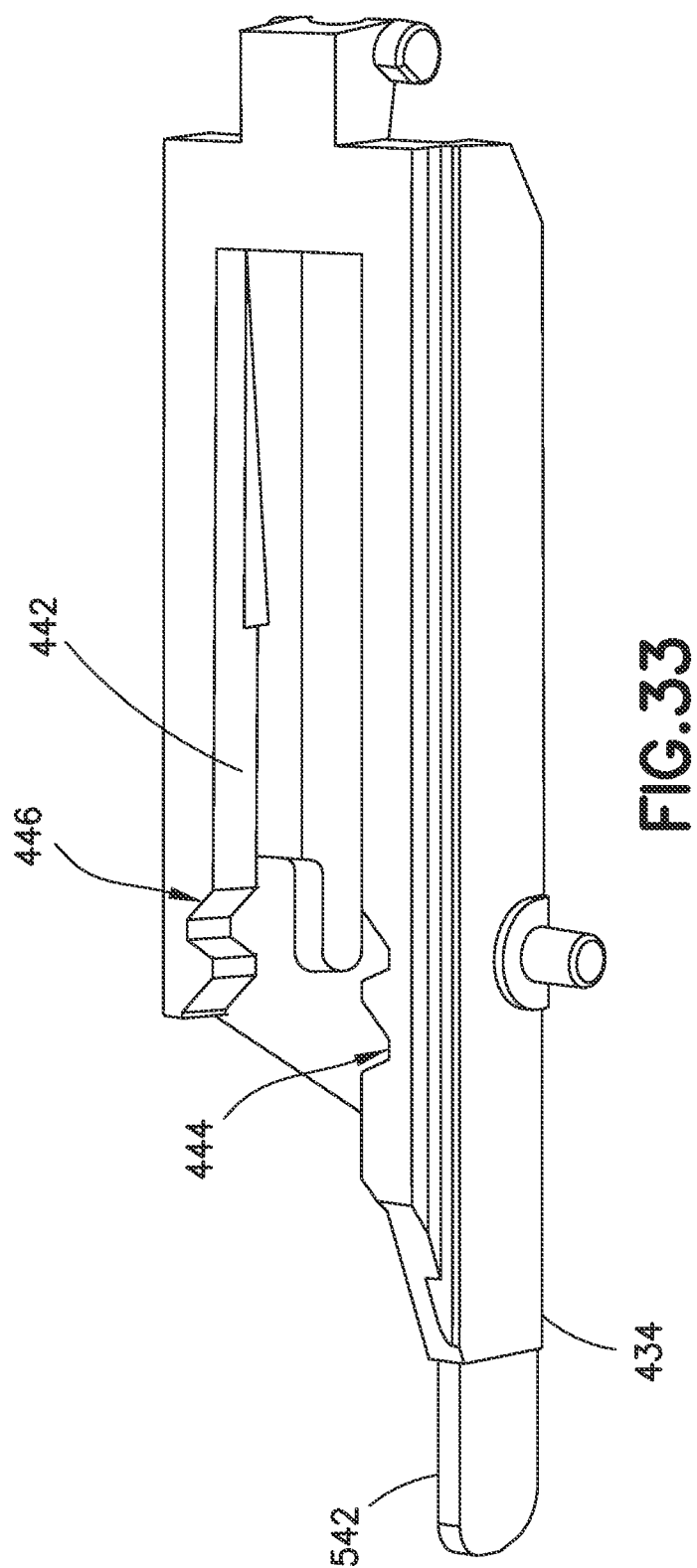
FIG. 33 is a top perspective view of a lift lever of the mechanism of FIG. 32.

As shown in FIGS. 32 and 33, the lift lever 434 includes a track 442 that the snap arms 438 ride against. According to one embodiment, on each side, the track 442 has a pair of detents 444 and 446. In an initial position and prior to removal of the needle cover 430, the snap arms 438 are held in place or locked against the track 442 by the needle cover 430. In other words, the safety extension 432 prevents the snap arms 438 from displacing toward each other and disengaging from the detents 444. Once the needle cover 430 is removed, the user is able to slide the button 436 forward toward the second end of the device. During this movement of the button 436, because of the forward angled faces of the detents 444 and the forward angled faces of the locking protrusions 440, the free ends of the snap arms 438 laterally deform or deflect toward each other, thereby permitting the locking protrusions to disengage from the detents 440 and engage the detents 446. Once this occurs, according to one embodiment, because of the interaction of the rear angled faces of the detents 446 and the rear angled faces of the locking protrusions 440, the user cannot return the button to its initial position.

Thus, according to one embodiment, the actuation button 436 includes at least one cantilevered snap arm 438, and prior to needle cover removal, the snap arm 438 engages a detent 444 in the device and the safety extension 432 contacts the snap arm 439 and prevents the snap arm 438 from disengaging from the detent 444.

When the button 436 is in the initial position and the needle cover 430 is removed, unless the user applies sufficient force to deflect the snap arms 438 inward and engage the locking protrusions 440 with the detents 446, the interaction between the forward angled faces of the detents 444 and the forward angled faces of the locking protrusions 440, combined with the flexibility of the snap arms 438, causes the button 436 returns to its initial position with the locking protrusions engaged with the detents 444.

The angles of the forward faces of the locking protrusions 440 and the forward faces of the detent 444 can be modified to adjust a force profile required from the user to activate the medical device. For example, the obtuse angle between the of the forward face of the locking protrusion 440 and the straight portion of the snap arms 438 can be increased (and the corresponding angle of the forward face of the detent 444 can be modified) to lower the amount of force required by a user to overcome the interaction with the detent 444 and activate the device. Preferably, the force required to activate the device is between about 4-10 N (0.9-2.2 $lb_F$).

Figure 34:
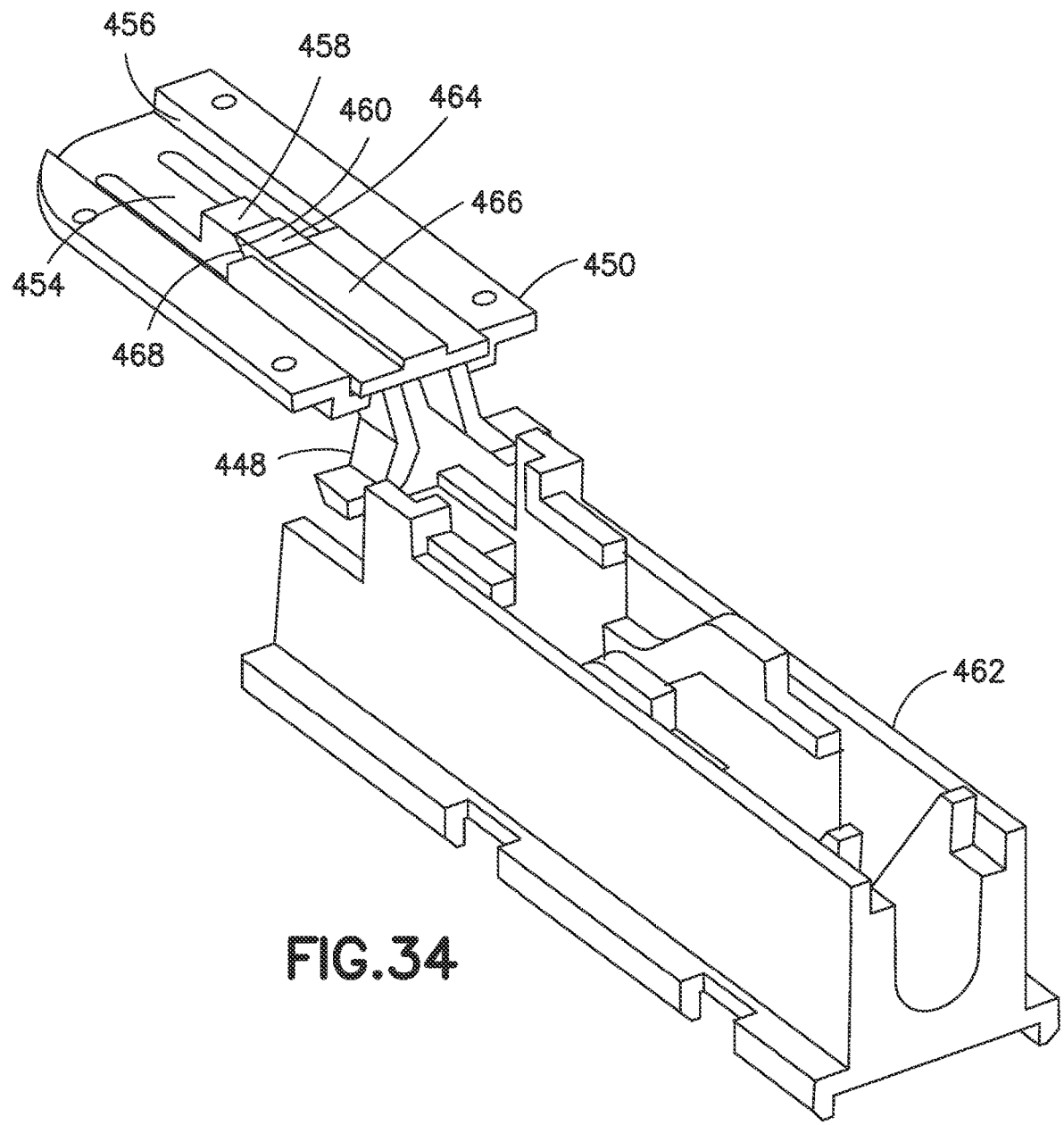
FIGS. 34 and 35 are respective top and bottom perspective views of an embodiment of a stage-indicating mechanism in accordance with an embodiment of the present invention.
Figure 35:
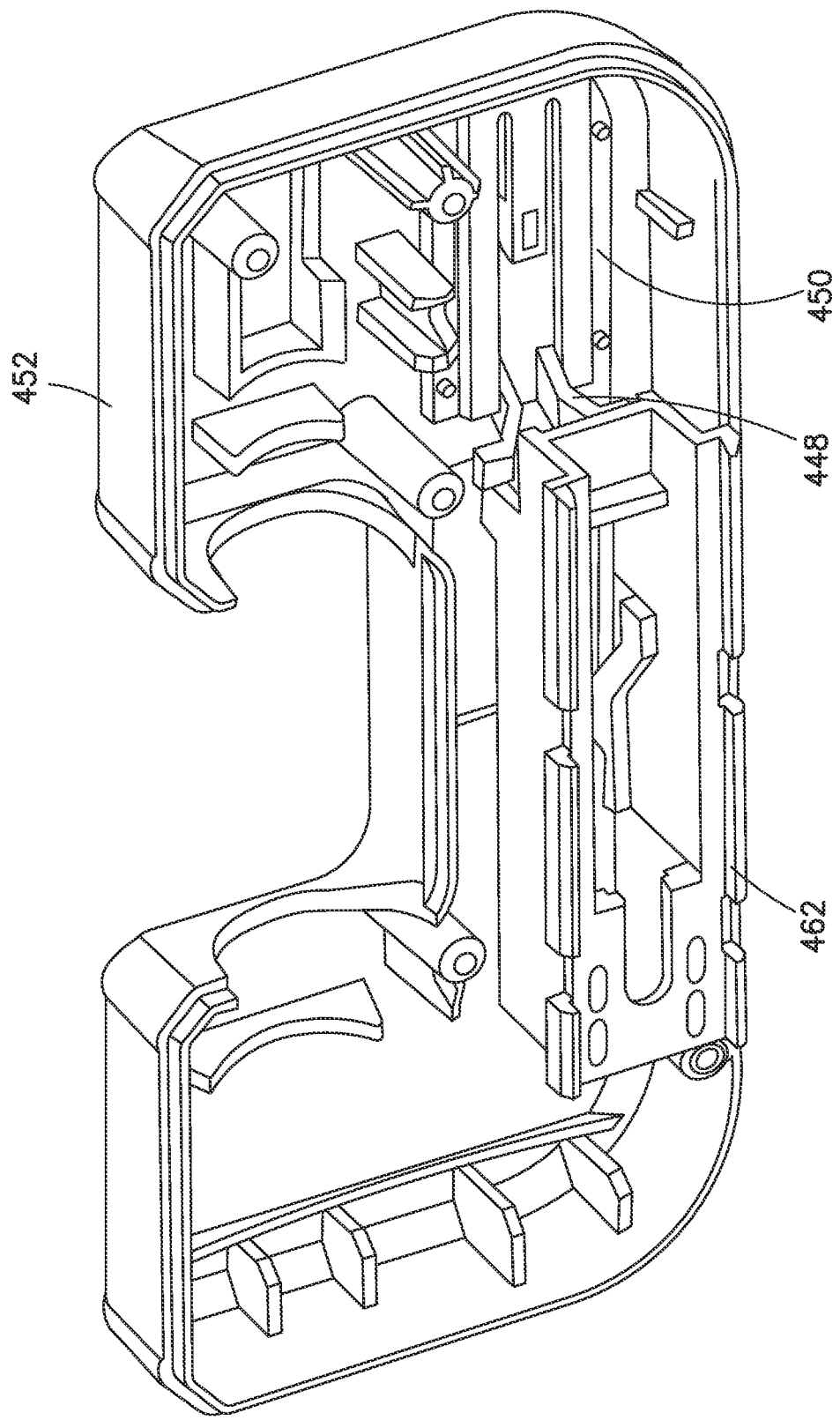

In contrast to the stage-indicating structure 226 shown in FIG. 13, another embodiment of a stage-indicating mechanism is illustrated in FIGS. 34 and 35. The mechanism includes an indicator 448 and an indicator guide 450. The indicator guide 450 is fixedly connected to the top cover 452 and includes a cantilevered arm 454 and a guide slot 456 vertically supporting and guiding the indicator 448. The free end of the cantilevered arm 454 includes an indicator face 458 and an angled sliding surface 460. Prior to activation, the indicator face 458 is visible through the status viewport of the top cover 452 to indicate that the device has not yet been activated. This embodiment provides more room for assembling fluid path components in the device.

The top surface of the indicator includes an area indicating the first activation stage 464 and an area indicating the second activation stage 466. The end of indicator has an angled surface 468 that is substantially complimentary to the angled sliding surface 460 of the cantilevered arm 454. When the device is assembled, the indicator 448 is adjacent to and contacts the needle actuation slider or slider 462, but is not connected to the slider 462. Instead, subsequent to activation, as the slider displaces, the slider moves the indicator 448.

More specifically, as previously described, during the first activation stage, the slider 462 displaces forward by a first distance (permitting the needle insertion into the user). In this embodiment, the first forward displacement of the slider also displaces the indicator 448 forward. The forward displacement of the indicator 448 causes the angled surface 468 to ride over the angled sliding surface 460, downwardly deflecting the free end of the cantilevered arm 454, and displaying the area indicating the first activation stage 464 through the status viewport. During the second activation stage, the slider 462 displaces forward by a second distance, and displaces the indicator 448 forward to display the area indicating the second activation stage 466 through the status viewport.

Figure 36:
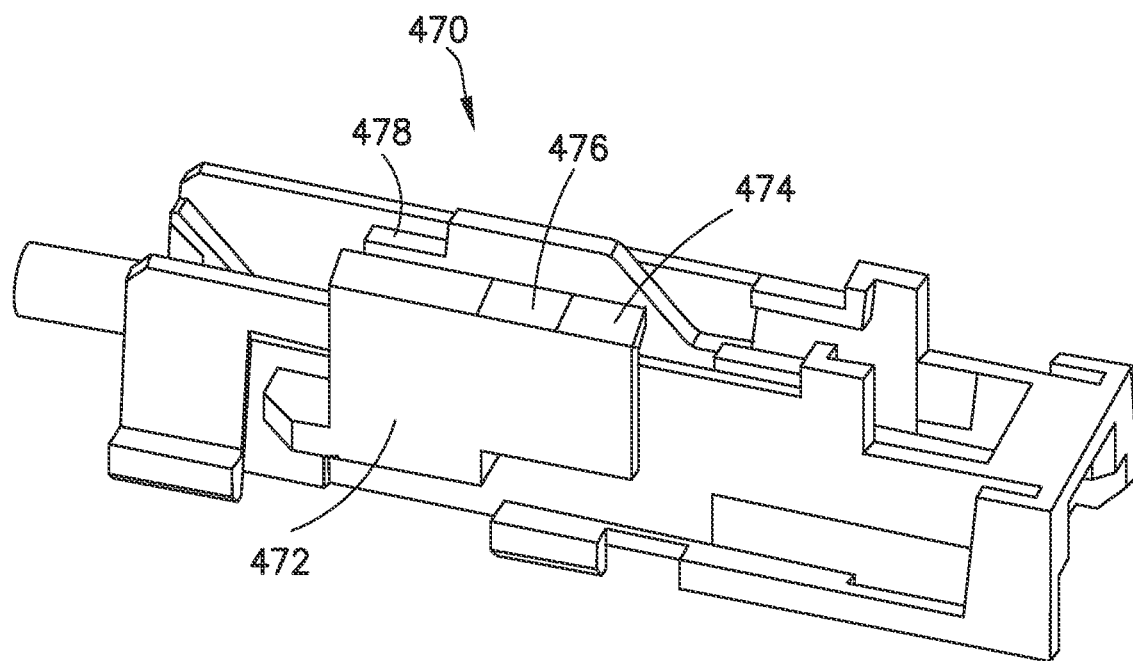
FIG. 36 is a top perspective view of a needle actuation slider in accordance with another embodiment of the present invention.
Figure 37:
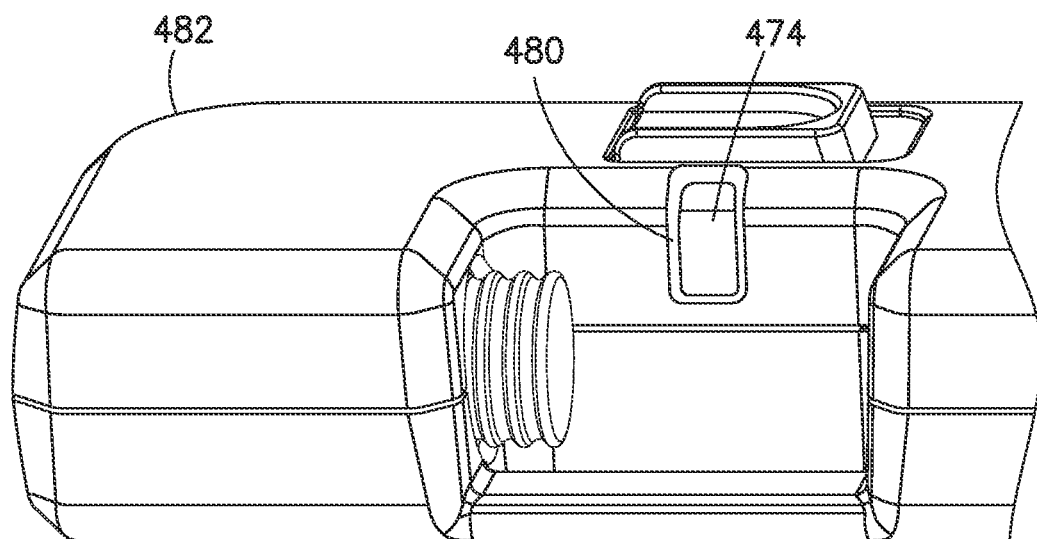
FIG. 37 is a partial top perspective view of a top cover in accordance with another embodiment of the present invention.

FIG. 36 illustrates another embodiment of the needle actuation slider or slider 470. Similar to the slider 196, in this embodiment, the slider 470 includes a stage-indicating structure 472 fixedly connected thereto. But rather than being disposed at the forward end, in this embodiment, the stage-indicating structure 472 is disposed on the side of the slider 470. The stage-indicating structure 472 includes an area indicating the pre-activated stage 474, and area indicating the first activation stage 476, and an area indicating the second activation stage 478. As shown in FIG. 37, the various stage-indicating areas (474, 476, and 478) are visible through the status viewport 480 of the top cover 482.

Figure 38:
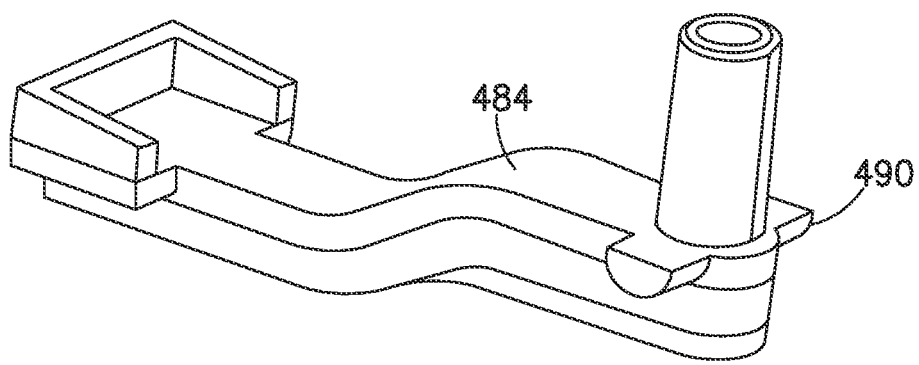
FIG. 38 is a top perspective view of a switch arm in accordance with another embodiment of the present invention.
Figure 39:
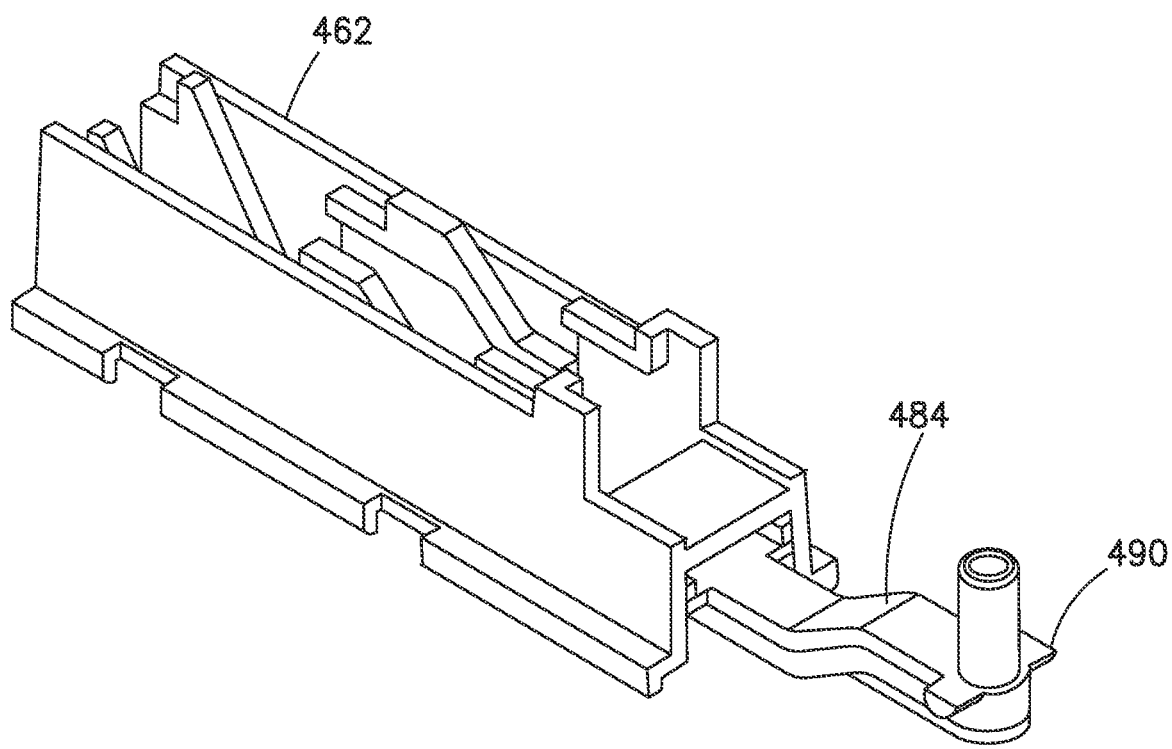
FIG. 39 is a top perspective view of the switch arm of FIG. 38 and a needle actuation slider in accordance with another embodiment of the present invention.
Figure 40:
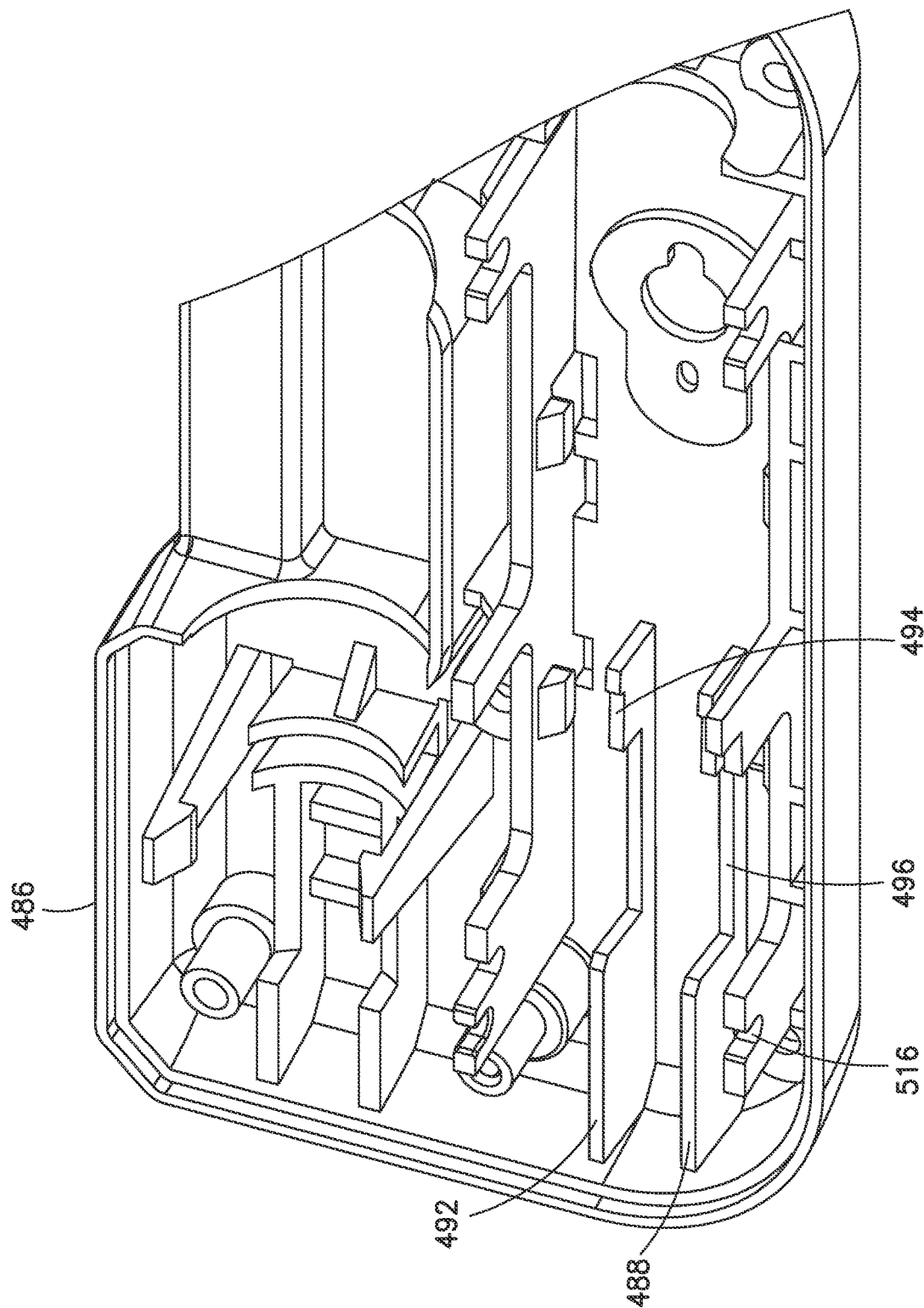
FIG. 40 is a partial top perspective view of a bottom cover in accordance with an embodiment of the present invention.
Figure 41:
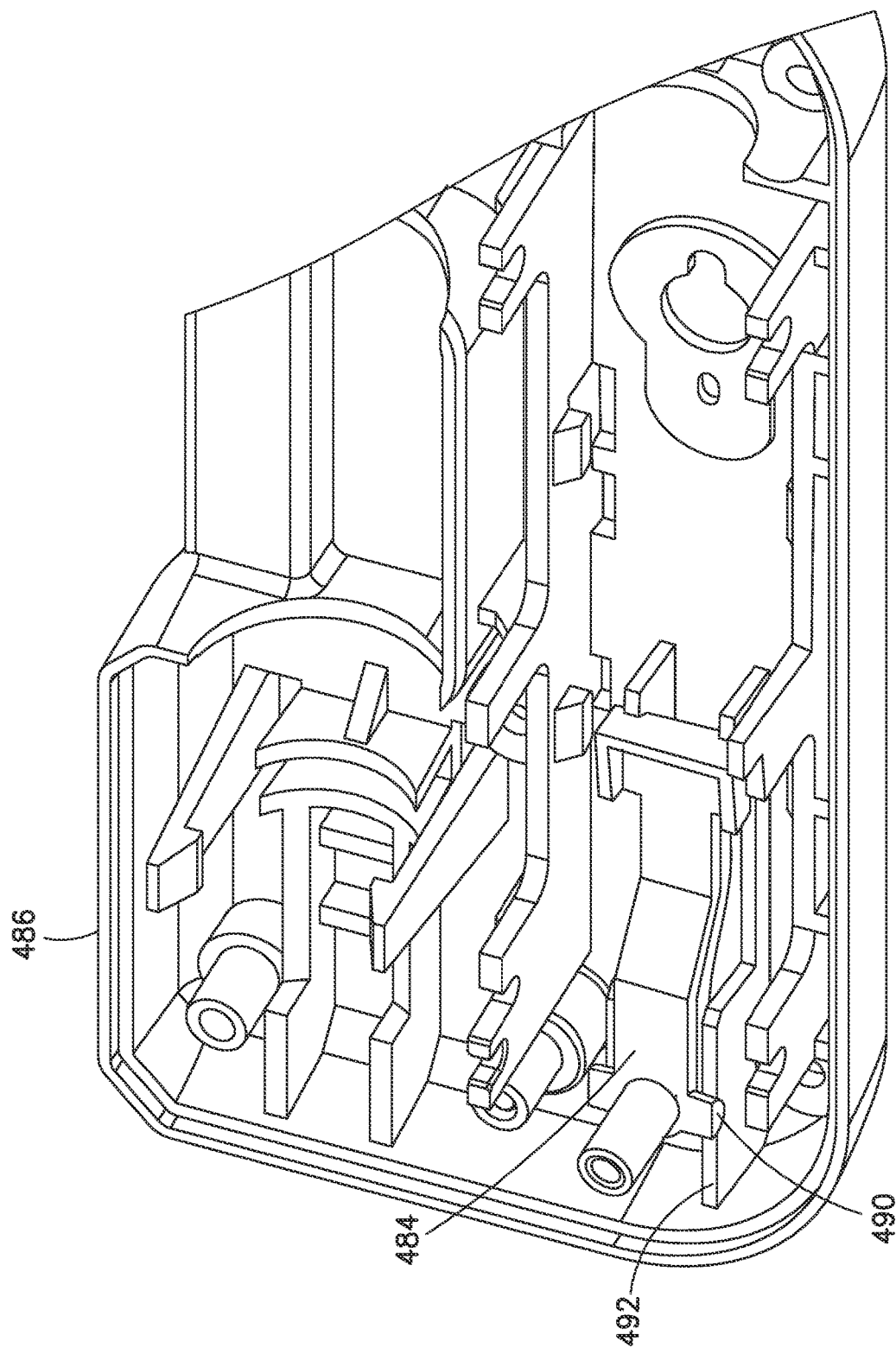
FIG. 41 is a partial top perspective view of the switch arm of FIG. 38 and the cover of FIG. 40.

FIG. 38 illustrates another embodiment of a switch arm or flip arm 484. Prior to the device's activation, the rear portion of the switch arm 484 resides in a recess of the needle actuation slider 462, as shown in FIG. 39. In addition, as shown in FIGS. 40 and 41, the bottom cover 486 includes a switch arm track 488 for guiding movement of the switch arm 484. FIG. 41 illustrates the switch arm prior to activation of the device. Front protrusions 490 rest on an upper track portion 492 and the rear portion of the switch arm 484 rests on the initial track portion 494.

Figure 42:
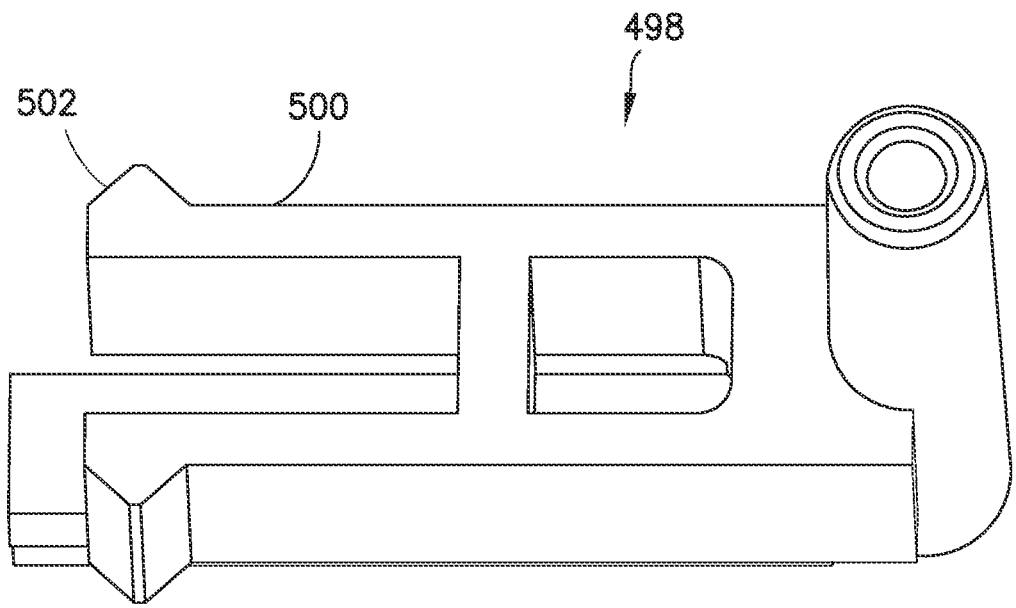
FIGS. 42 and 43 are respective top and bottom perspective views of a switch arm in accordance with another embodiment of the present invention.
Figure 43:
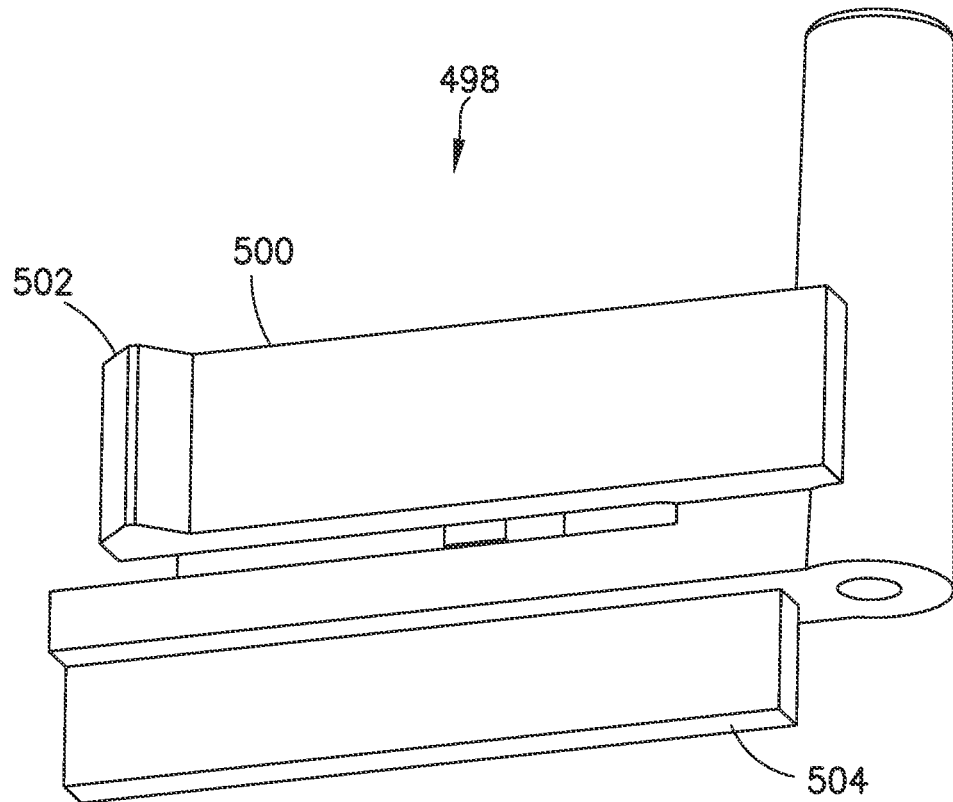

Subsequent to activation, during the first activation stage, the slider 462 displaces forward by a first distance, displacing the switch arm 484 forward (to rotate the rocker) until the rear portion of the switch arm 484 falls off the initial track portion onto a lower track portion 496. By lowering the rear portion of the switch arm 484 in this manner, the slider 462 can pass over the rear portion of the switch arm 484 without further displacing the switch arm 484 during the second activation stage. This configuration allows the slider 462 to travel a greater internal total distance FIGS. 42 and 43 are respective top and bottom perspective views of a switch arm or flip arm 498 in accordance with another embodiment of the present invention. The switch arm 498 includes a pair of rear cantilevered arms 500, each having a snap protrusion 502 on its free end. The switch arm 498 also includes a guide rail 504 disposed on a bottom thereof that rides in a guide track in the bottom cover (not shown) to guide movement of the switch arm 498.

Figure 44:
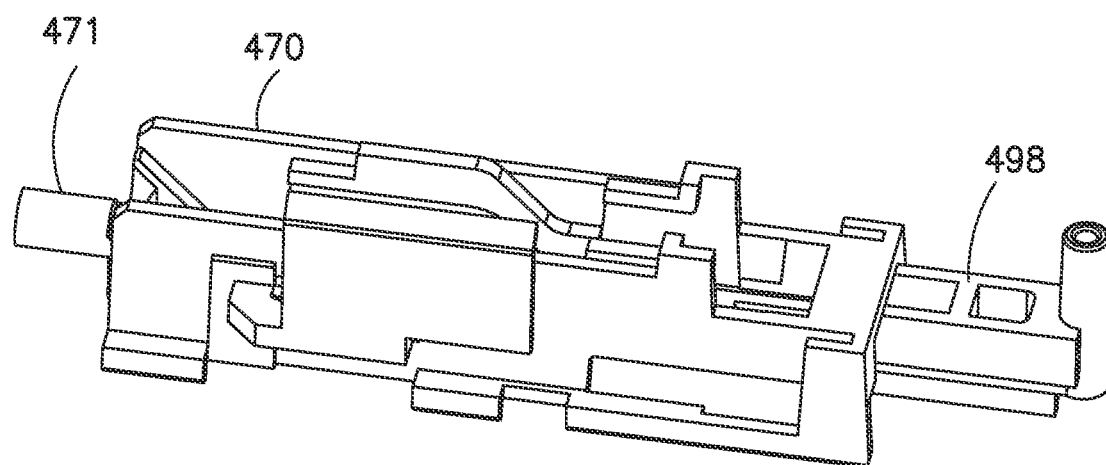
FIG. 44 is a top perspective view of the switch arm of FIG. 42 and the needle actuation slider of FIG. 36.

Prior to activation, the snap protrusions 502 rest against the forward end of the slider 470. Subsequent to activation, during the first activation stage, the slider 470 displaces forward by a first distance, displacing the switch arm 498 forward (to rotate the rocker) to its final forward position. According to one embodiment, at the beginning of the second activation stage, the slider 470 displaces further forward, but because the switch arm 498 does not displace further forward, the forward end of the slider 470 rides against the angled surfaces of the snap protrusions 502, deflecting the two cantilevered arms 500 toward each other. Further forward motion of the slider 470 bypasses the snap protrusions 502, as shown in FIG. 44, thereby permitting the slider 470 to travel further forward still. According to another embodiment, the forward end of the slider 470 bypasses the snap protrusions 502 at the end of its travel during the first activation stage. Additionally, as shown in FIG. 44 and subsequently described in greater detail, the slider 470 includes a rear protrusion 471 for registration with the needle actuation plunger.

Figure 45:
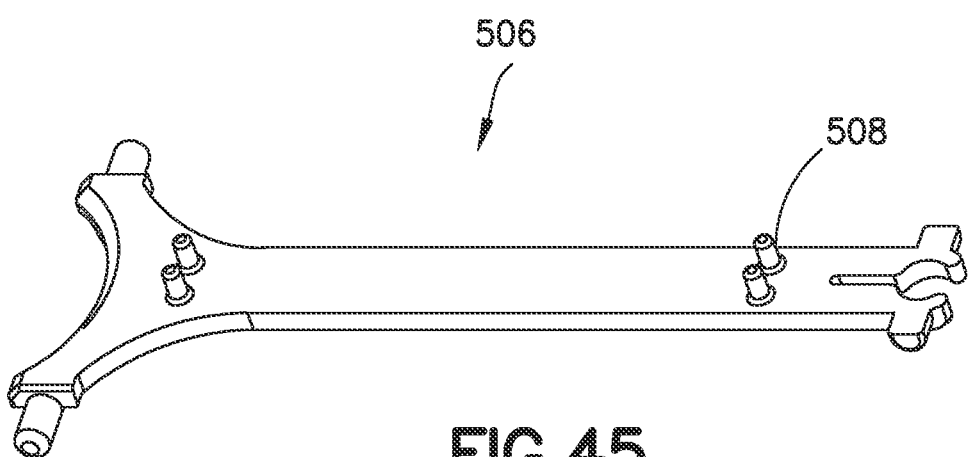
FIG. 45 is a top perspective view of a another needle arm in accordance with an embodiment of the present invention.
Figure 46:
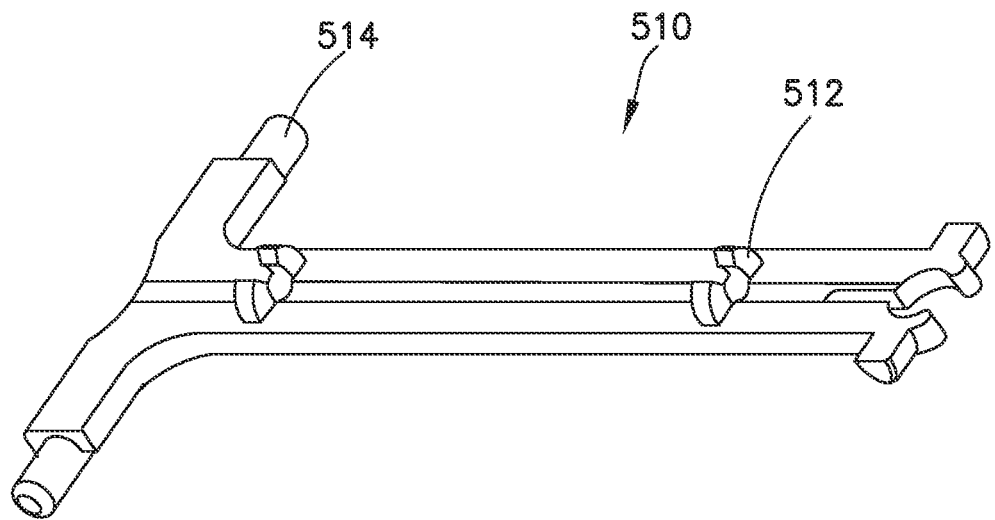
FIG. 46 is a top perspective view of a another needle arm in accordance with an embodiment of the present invention.

FIGS. 45 and 46 illustrate alternative embodiments of the needle arm. As shown in FIG. 45, the needle arm 506 includes two pair of substantially vertical guide posts 508 for guiding installation and preventing lateral displacement of the tubing of the fluid pathway. In contrast, the needle arm 510 of FIG. 46 includes two pairs of snap guides 512 to which the tubing is secured during installation. Additionally, according to one embodiment, the pivots 514 and the corresponding pivot yokes 516 (see, for example, FIG. 40).

Figure 47:
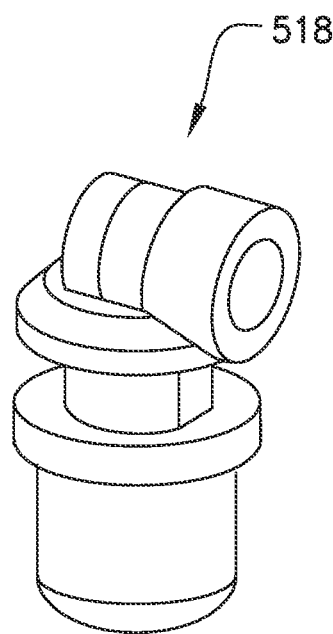
FIG. 47 is a top perspective view of a port in accordance with an embodiment of the present invention.

FIG. 47 is a top perspective view of a port 518 in accordance with an embodiment of the present invention. In contrast to the previously-described port 300 (see, for example, FIG. 25) which makes a vertical connection with the tubing, the port 518 makes a substantially horizontal connection with the tubing. This provides for less bending of the tubing during installation and additional clearance for the tubing once the needle is withdrawn.

Figure 48:
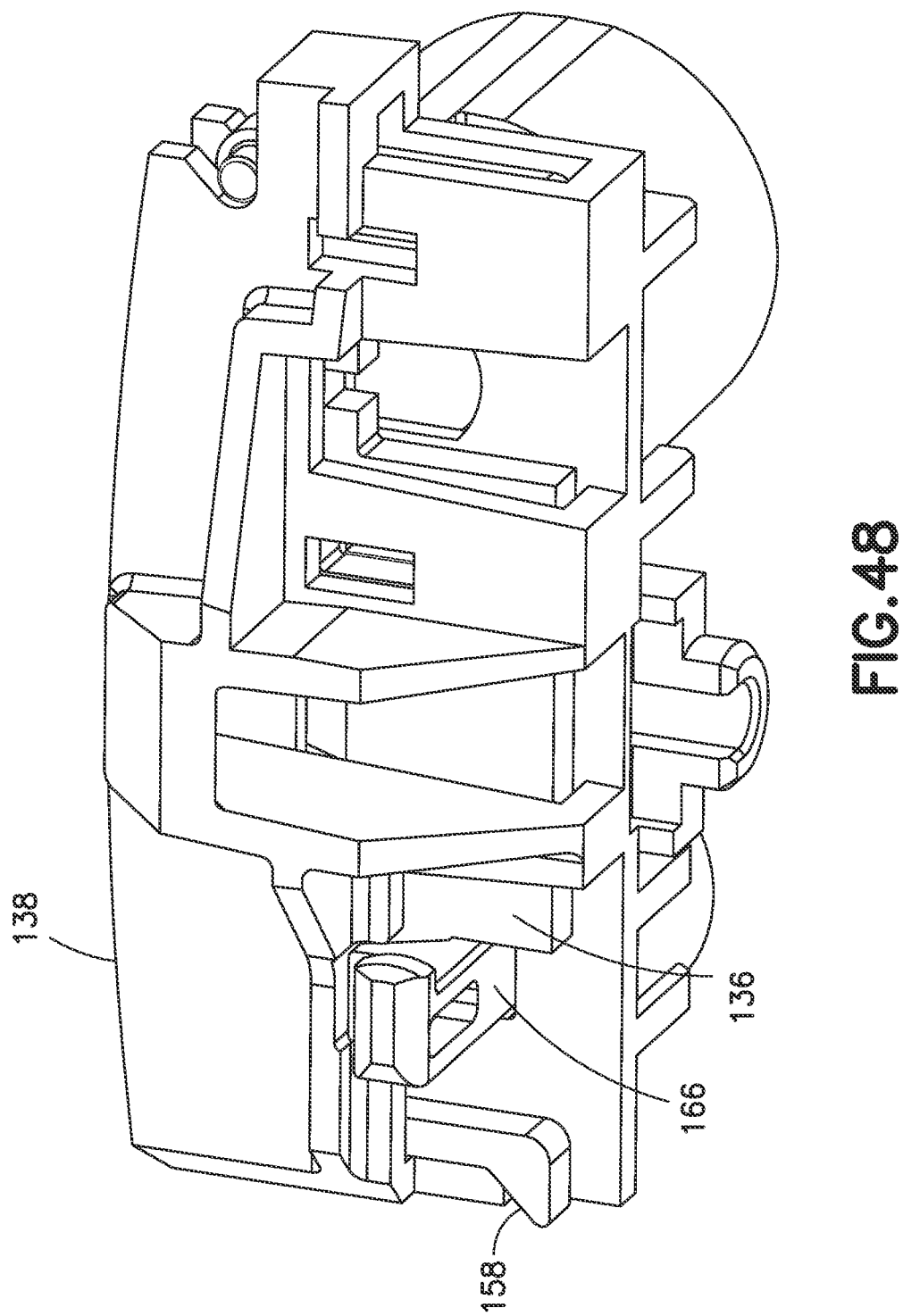
FIG. 48 is a rear perspective view of power module elements of the device of FIG. 1.
Figure 49:
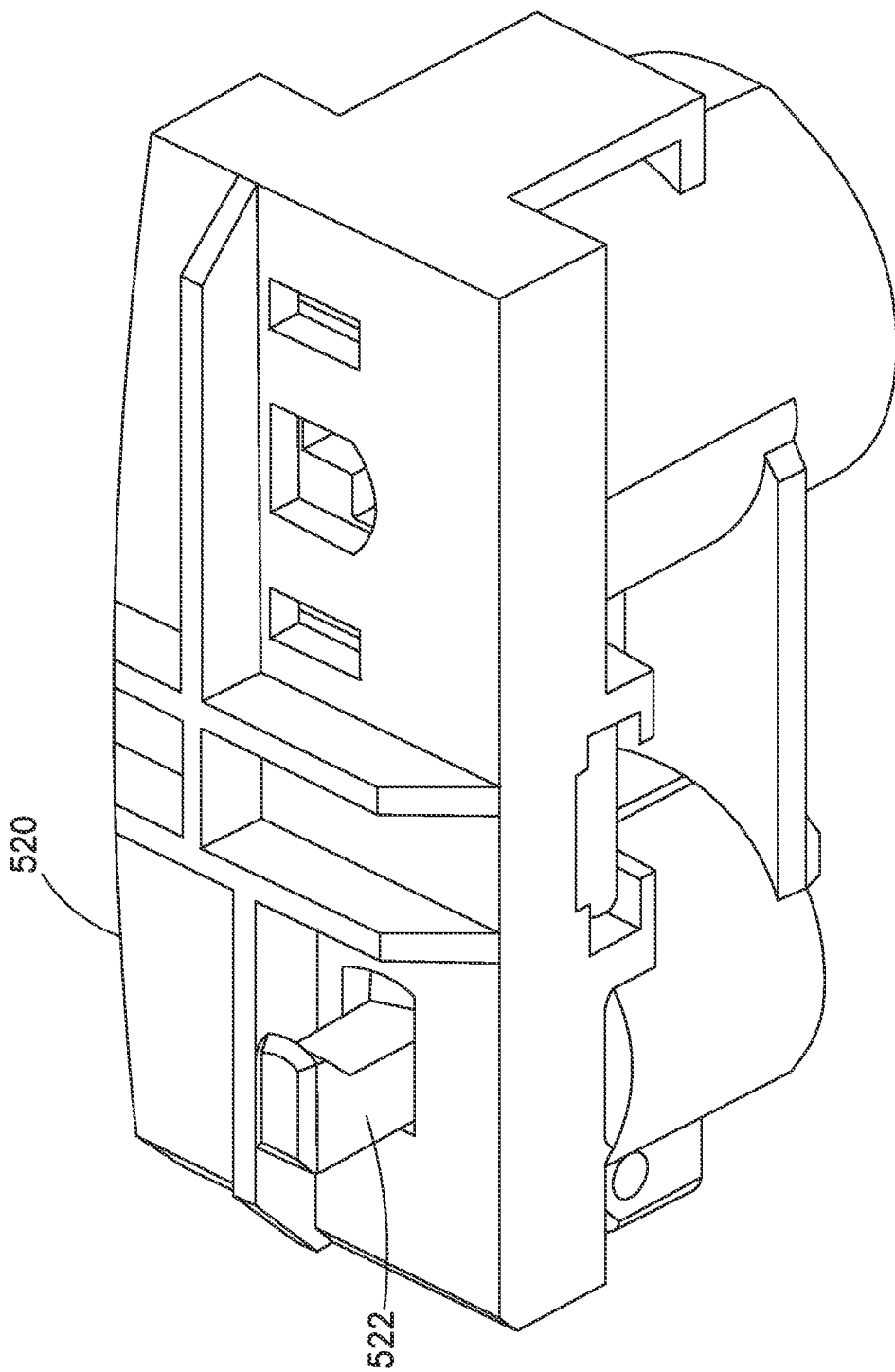
FIG. 49 is a rear perspective view of power module elements in accordance with another embodiment of the present invention.

FIG. 48 is a rear perspective view of a power module of the device 100, illustrating the relative positioning of the frame 138, the shutter 136, and the needle actuation plunger 166 prior to activation of the device 100. In contrast, FIG. 49 illustrates another embodiment of the frame 520 that substantially encloses the shutter except for its top, and supports the bottom of the needle actuation plunger 522 during its travel.

Figure 50:
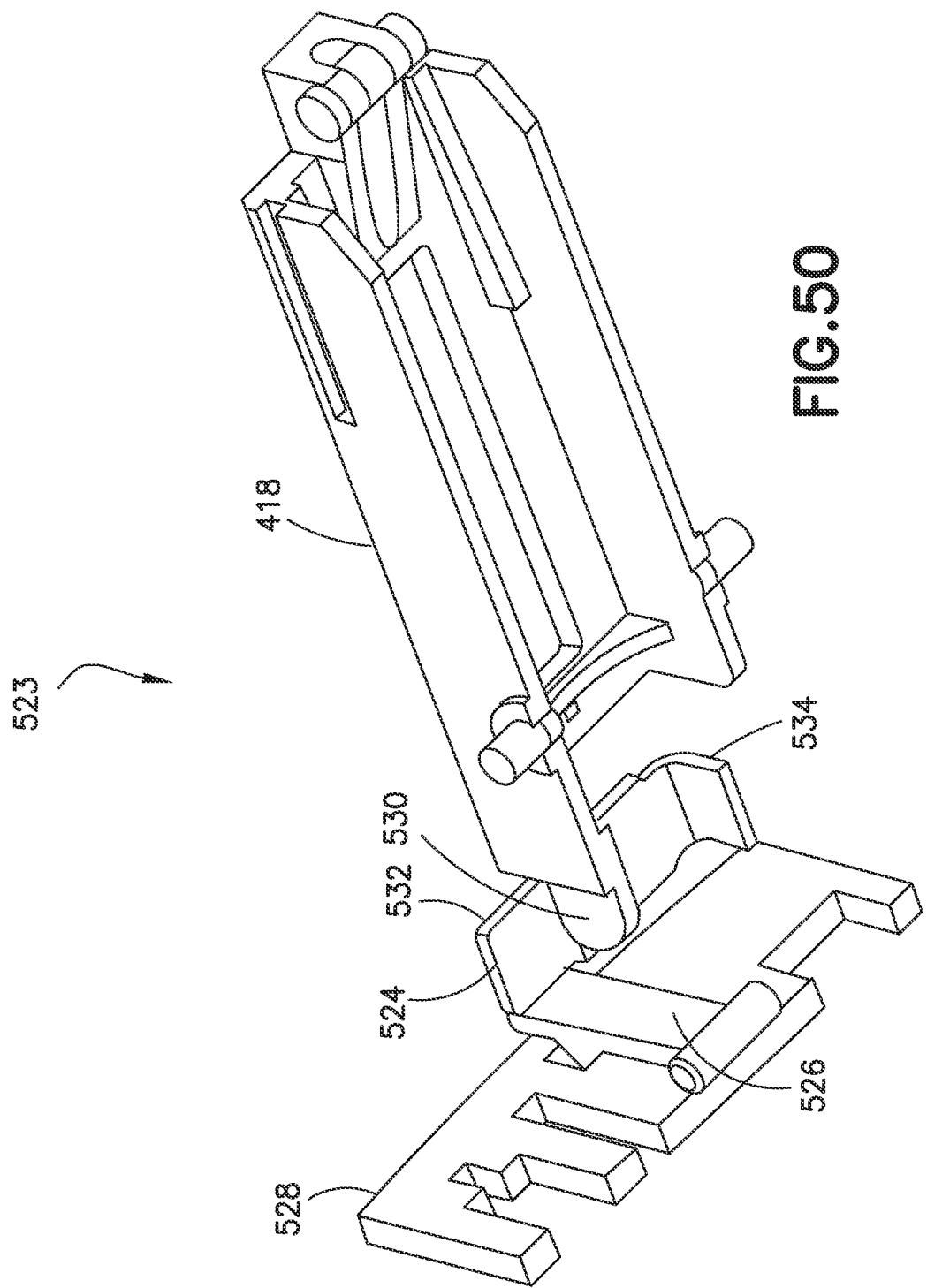
FIG. 50 is a bottom perspective view of a shutter latching mechanism in accordance with an embodiment of the present invention.

FIG. 50 is a bottom perspective view of a shutter latching mechanism 523 in accordance with an embodiment of the present invention. The shutter latching mechanism of this embodiment includes the lift lever 418, a latch beam 424, the shutter latch 526, and the shutter 528 illustrated prior to activation The lift lever 418 (also shown in FIG. 30) includes a lifting arm 530 that engages the latch beam 424, which keeps the shutter latch 526 engaged with the shutter 528. The latch beam 524 is an L-shaped element having a long portion 532 and a short portion 534. According to one embodiment, the short portion 534 is secured in a pocket of the frame 520. Preferably, the latch beam 424 is made of sheet metal or spring metal, and is strong but flexible.

In operation, when the device is activated, the front portion of the lift lever 418 rotates down (due to the user force on the button), thereby rotating the rear portion of the lift lever 418 up and lifting or deflecting the long portion 532 of the latch beam 524 so that it no longer contacts and supports the shutter latch 526. Subsequently, as in previously-described embodiments, the shutter latch 526 is freed from the shutter 528 and the needle actuation plunger 522 lifts the shutter 528.

Figure 51:
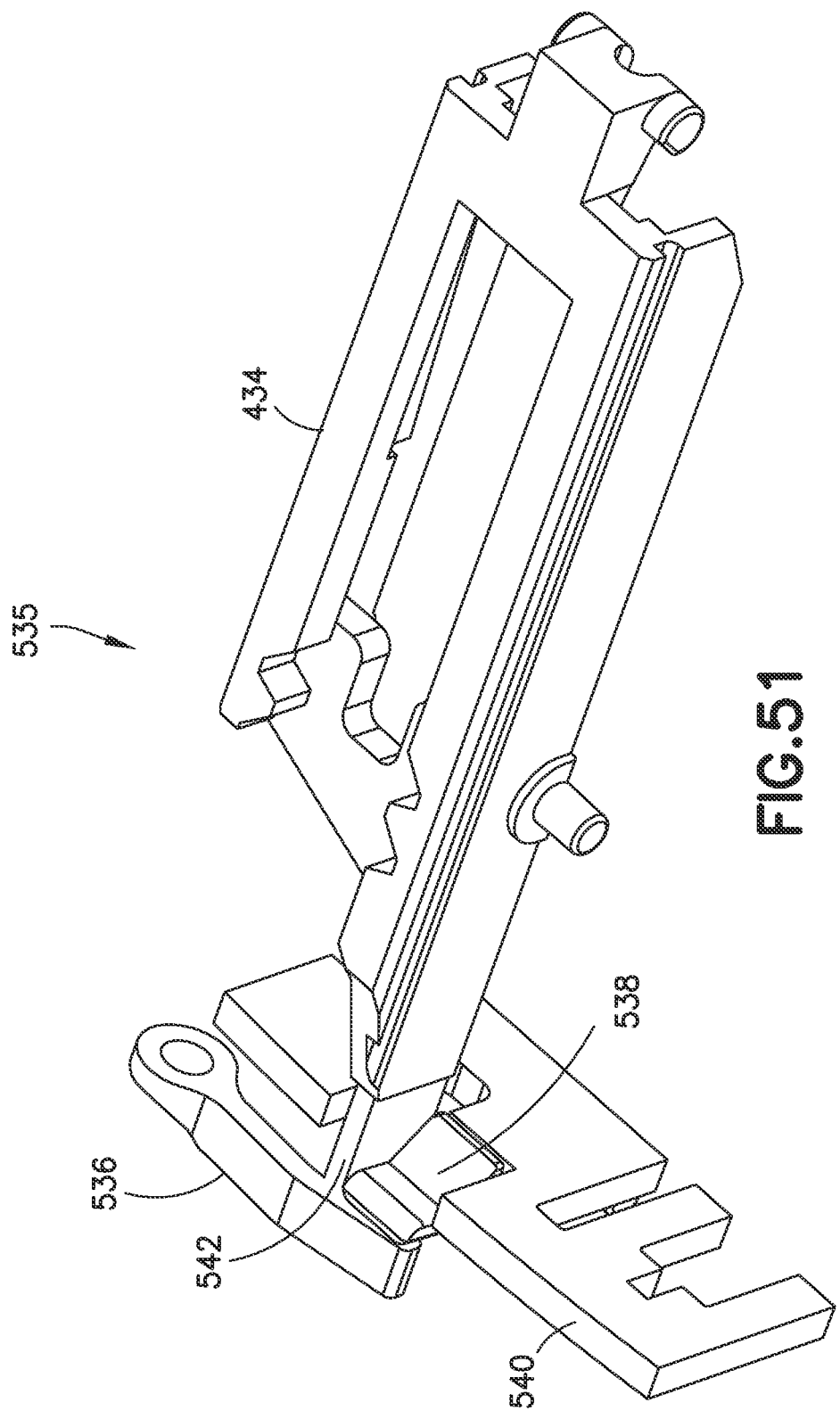
FIG. 51 is a bottom perspective view of a shutter latching mechanism in accordance with another embodiment of the present invention.
Figure 52:
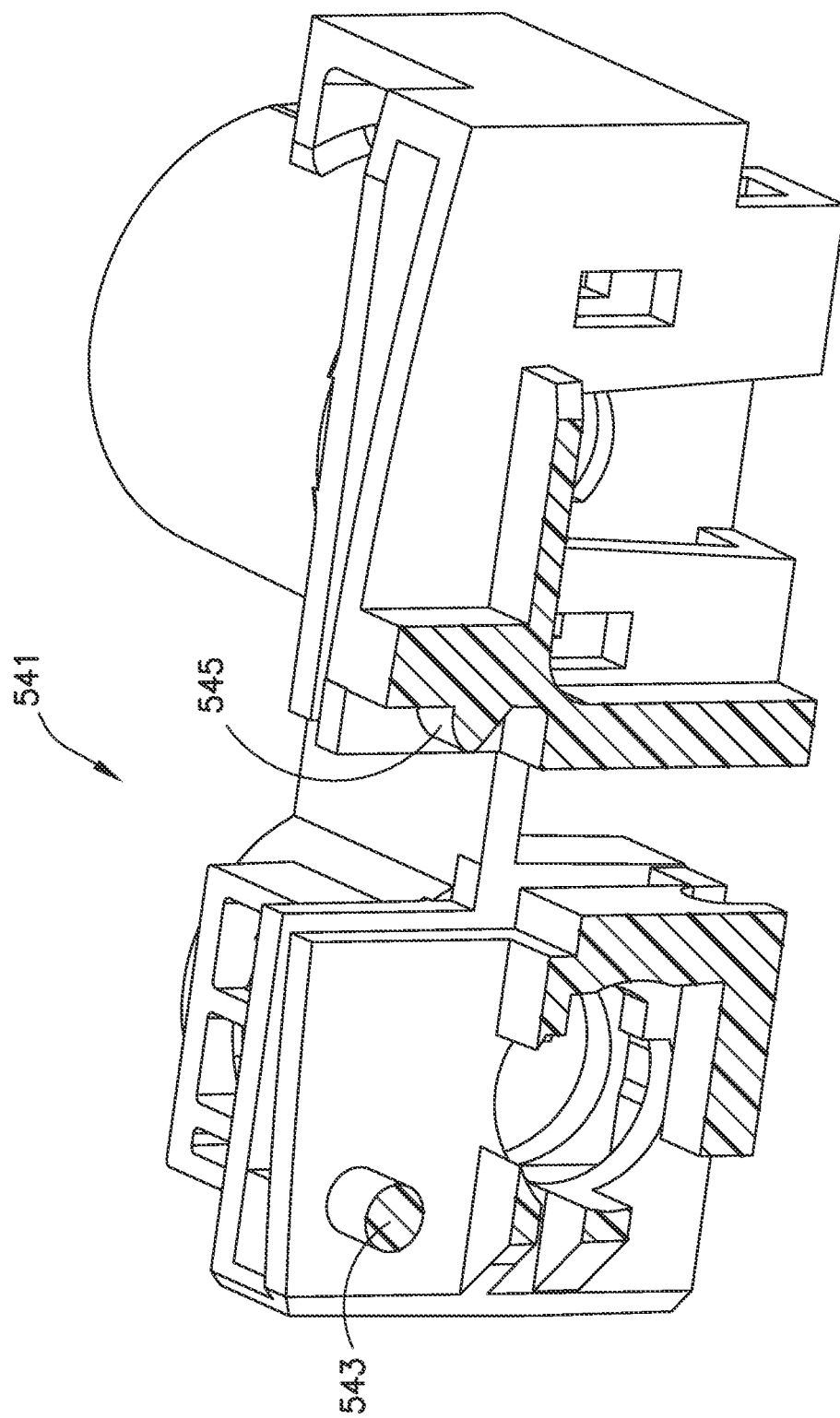
FIG. 52 is a rear perspective, cross-sectional view of a frame in accordance with an embodiment of the present invention.

FIG. 51 is a bottom perspective view of a shutter latching mechanism 535, and FIG. 52 is a rear perspective cross-sectional view of a frame or power module frame 541. The shutter latching mechanism of this embodiment includes the lift lever 434, a swing arm 536, the shutter latch 538, and the shutter 540 illustrated prior to activation in accordance with an embodiment of the present invention. The lift lever 434 (also shown in FIG. 33) includes a lifting arm 542 that engages the swing arm 536, which selectively keeps the shutter latch 538 engaged with the shutter 540.

The swing arm 536 is rotatably connected to the frame 541 at a stud 543 (see FIG. 52), and is preferably made of plastic. Prior to activation, the free end of the swing arm 536 is disposed beneath a frame protrusion 545. In operation, when the device is activated, the front portion of the lift lever 434 rotates down (due to the user force on the button), thereby raising the lifting arm 542 and rotating the swing arm 536 so that the free end is disposed above the frame protrusion 545 and the swing arm 536 no longer contacts and supports the shutter latch 538. Subsequently, as in previously-described embodiments, the shutter latch 538 is freed from the shutter 540 and the needle actuation plunger 548 (see FIG. 54) lifts the shutter 540.

In contrast to the shutter latching mechanism 523 shown in FIG. 50, in the embodiment shown in FIGS. 51 and 52, the swing arm 536 and the shutter latch 538 are located on the rear side of the shutter 540 and frame 541. This arrangement combined with the longer lifting arm 542 increases the lifting arm's effective travel. In addition, being able to make the swing arm out of plastic and its arrangement in the mechanism helps prevent creep prior to activation of the device.

Figure 53:
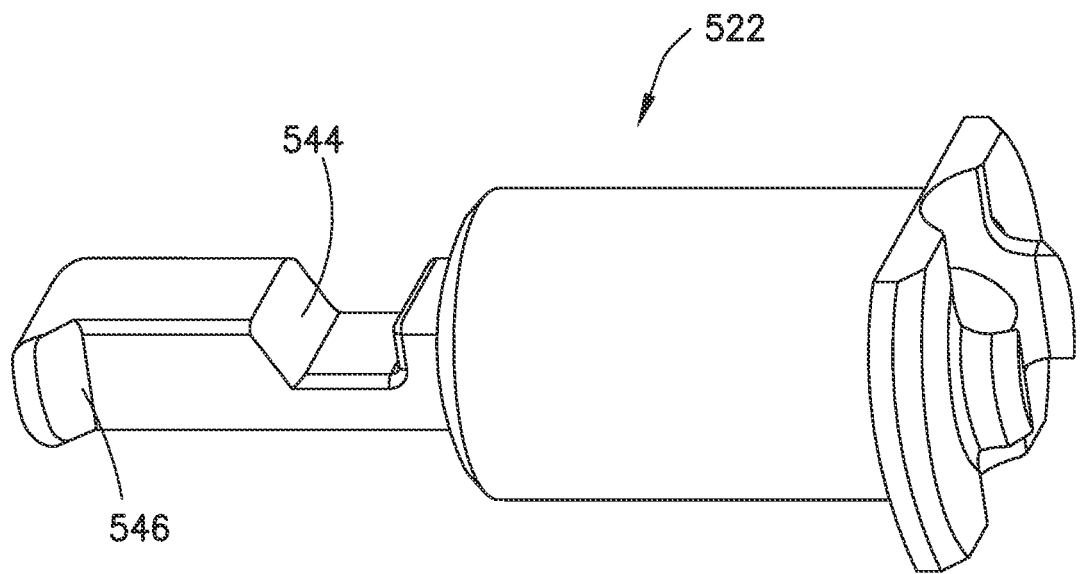
FIGS. 53 and 54 are top perspective views of needle actuation plungers in accordance with embodiments of the present invention.
Figure 54:
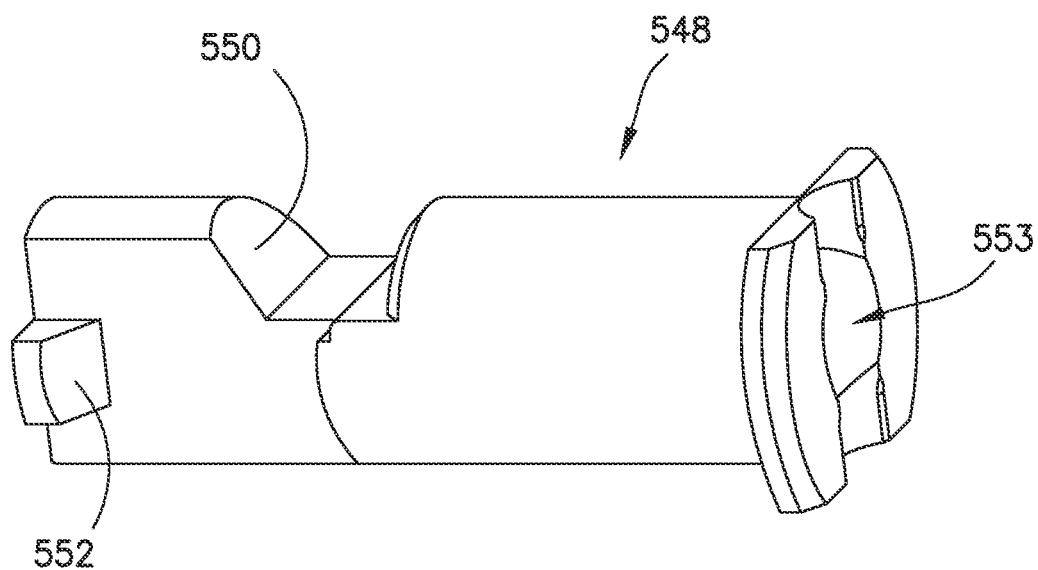

FIGS. 53 and 54 are top perspective views of needle actuation plungers in accordance with embodiments of the present invention. In comparison to the previously-described needle actuation plunger 166 (shown in FIG. 9), the needle actuation plunger 522 (also shown in FIG. 49) has a lower first engaging structure 544, and the second engaging structure 546 is angled. The needle actuation plunger 548 in FIG. 54 has a similar configuration with a lower first engaging structure 550 and an angled second engaging structure 552. Additionally, the needle actuation plunger 548 has a cavity 553 with a front opening that receives the slider's rear protrusion 471 (shown in FIG. 44). By linking the plunger 548 and the slider 470, the interaction between the cavity 553 and the rear protrusion 471 provides registration and guidance for the plunger 548 during its travel. The needle actuation plungers 522 and 548 can be made of plastic or metal, for example, aluminum.

Figure 55:
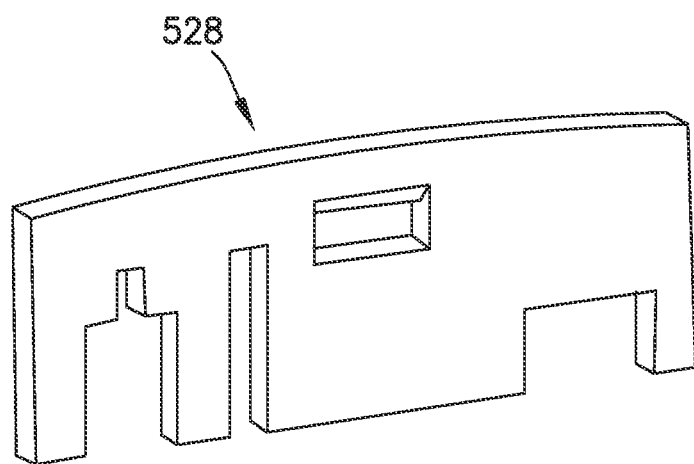
FIGS. 55 and 56 are top perspective views of shutters in accordance with embodiments of the present invention.
Figure 56:
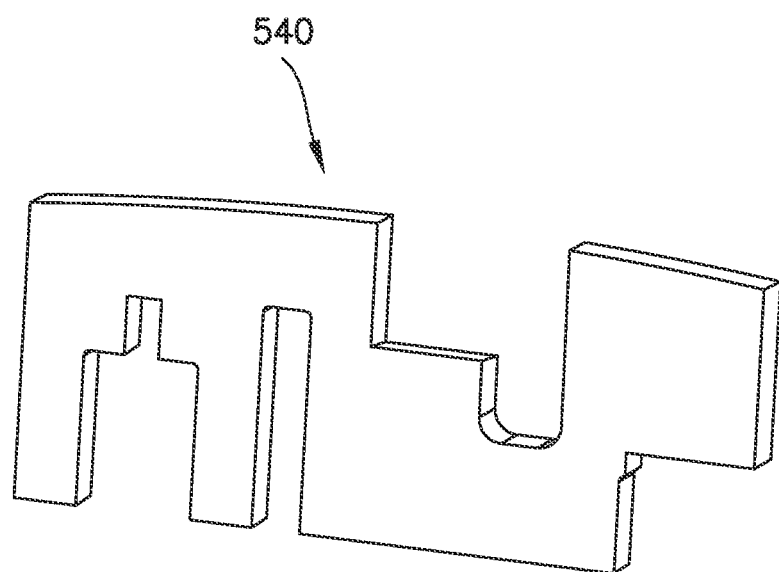

The lower first engaging structures 544 and 550 do not lift the shutter as high, and the angled second engaging structures 546 and 552 provide the side force to the shutter once the sliding arms 144 of the outer telescope member 146 displace and no longer contact the shutter, thereby eliminating the need for the biasing arm 158 of the shutter 136. Thus, in contrast to the previously-described shutter 136, the shutter 528 (shown in FIGS. 50 and 55) and the shutter 540 (shown in FIGS. 51 and 56) lack such a biasing arm.

FIG. 57 illustrates an embodiment of a two-part barrel plunger 554, which includes a plunger portion 556 and a plunger link 558. According to one embodiment, both the plunger portion 556 and the plunger link 558 have a cruciform shape. The plunger portion cruciform engages the barrel stopper and the plunger link cruciform engages the interior of the plunger portion cruciform, securing the two elements and preventing their relative rotation. Shapes other than a cruciform can be used without departing from the present invention's scope.

FIG. 58 illustrates a plunger link 560 in accordance with another embodiment of the present invention. The plunger link 560 includes a lift ramp 562 for lifting the shutter in concert with the needle actuation plunger's first engaging structure. Having both elements lift the shutter substantially simultaneously and to substantially the same height reduces the likelihood that the shutter will rack during lifting.

Figure 59:
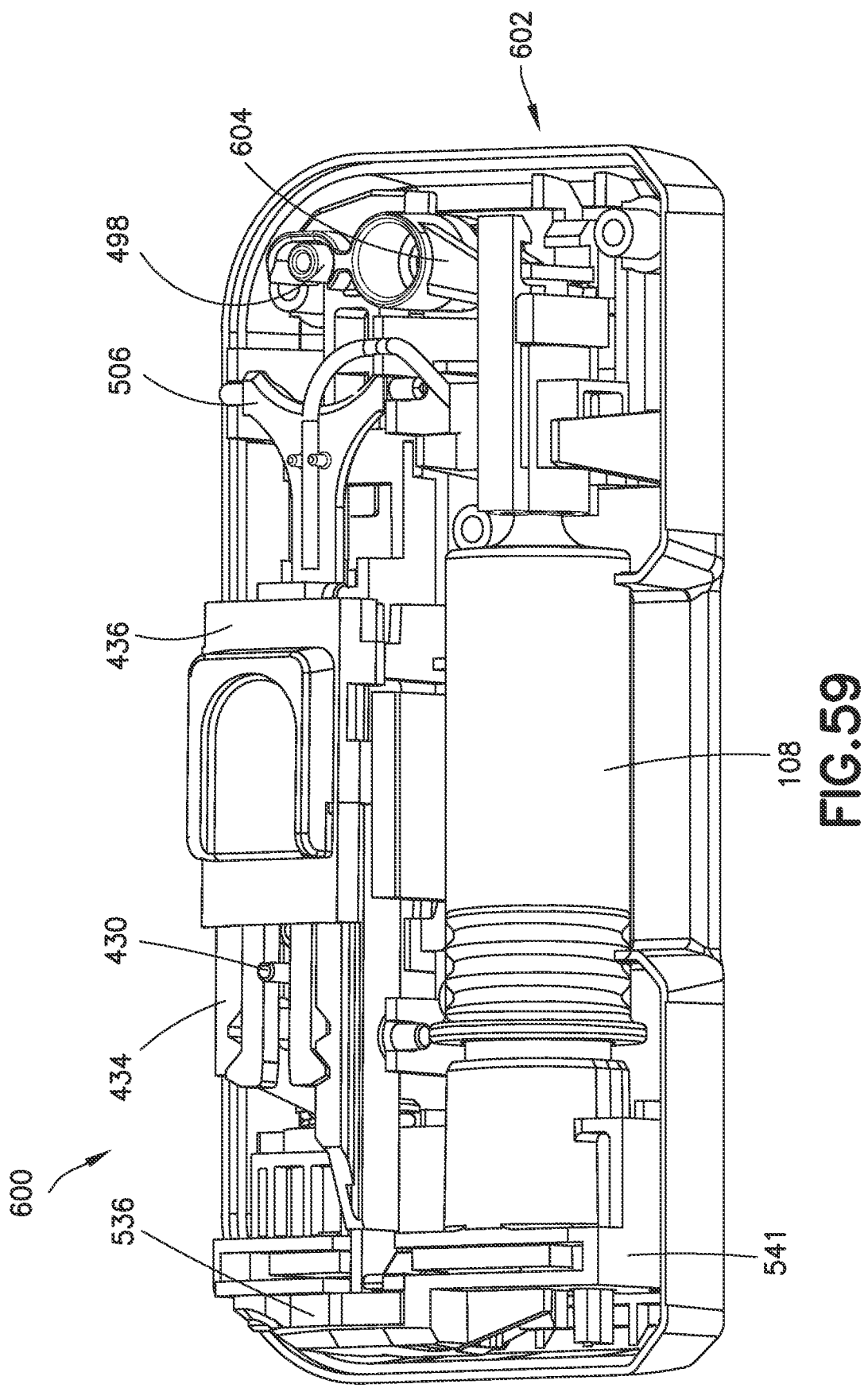
FIG. 59 is a top perspective rear view of a medical device in accordance with an embodiment of the present invention in a pre-activation stage and with a top cover removed.

FIG. 59 is a top perspective view of a medical device 600 incorporating selected ones of the previously-described features. For example, the device 600 includes the frame 541, the swing arm 536, the needle cover 430, the lift lever 434, the actuation button 436, the needle actuation slider 470, the needle arm 506, and the switch arm 498. The device 600 also includes a valve assembly 602, which includes the rocker 604, a valve release cap 606, and a septum fitting 608 disposed about the valve release cap 606, as shown in FIG. 59. The septum fitting 608 has a side port 618 connected to tubing 610 that fluidly connects to the patient needle.

Figure 60:
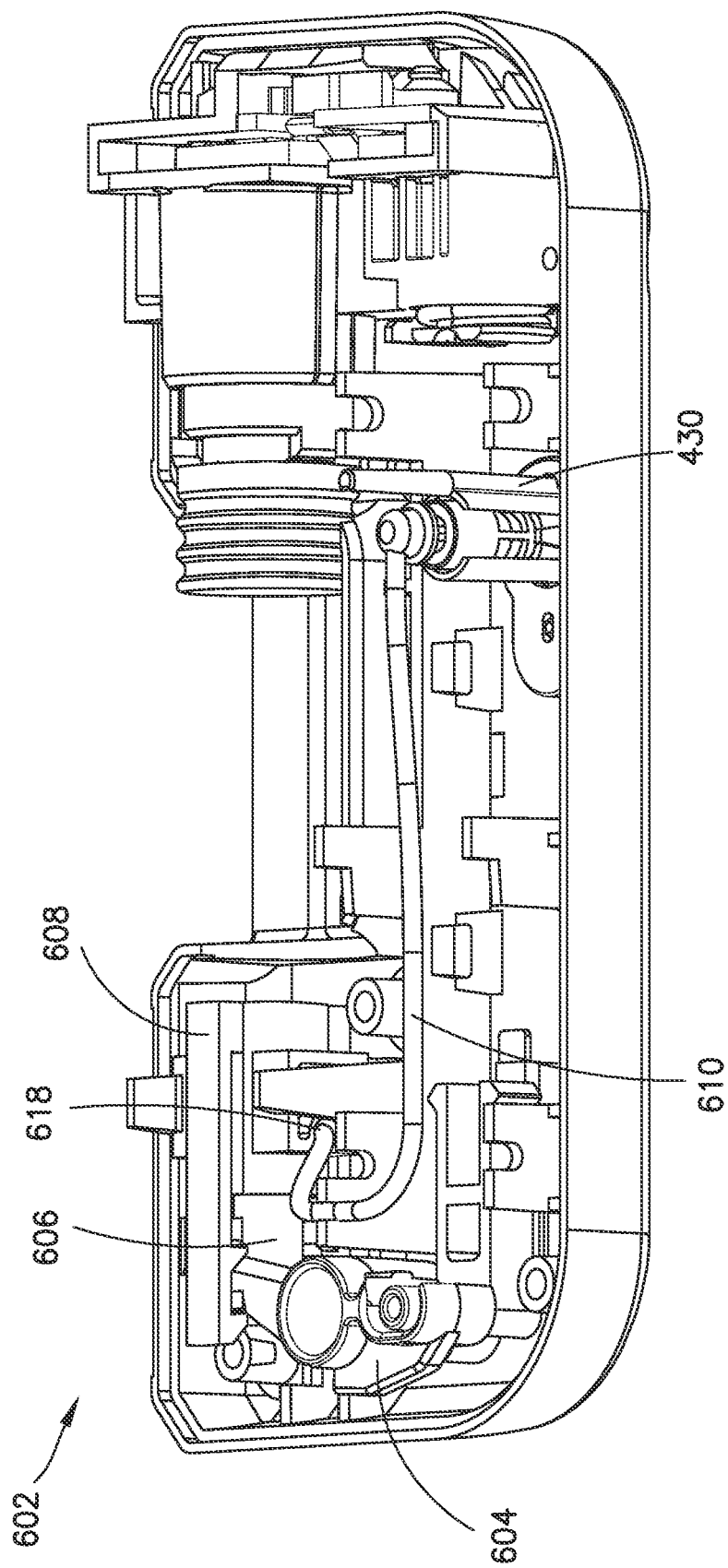
FIG. 60 is a top perspective front view of the device of FIG. 59 with several elements removed.
Figure 61:
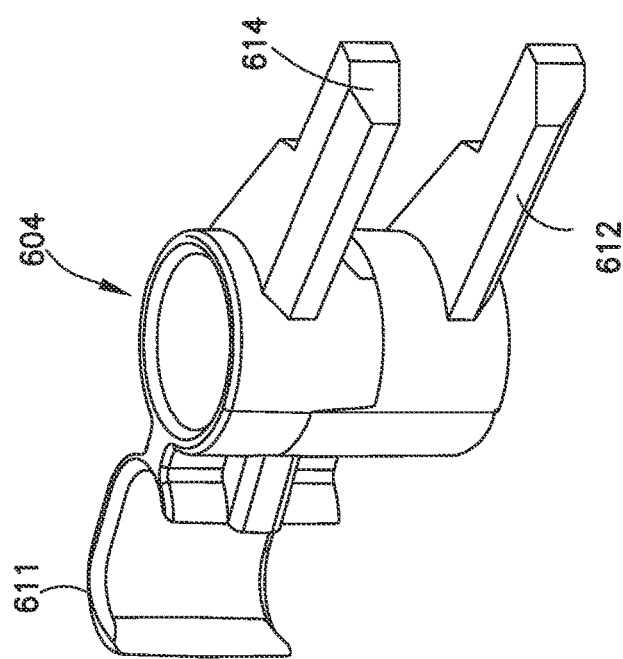
FIG. 61 is a top perspective view of a rocker in accordance with another embodiment of the present invention.

As shown in FIGS. 60 and 61, at the rocker's first end, the collar 611 that interfaces with the post of switch arm 498 is open, and at its second or valve end, the rocker 604 has a pair of arms 612. The ends of the rocker arms 612 include angled faces 614. As subsequently described in greater detail, upon activation of the device 600, the rocker arms splay apart the septum fitting's cantilevered base arms 616.

Figure 62:
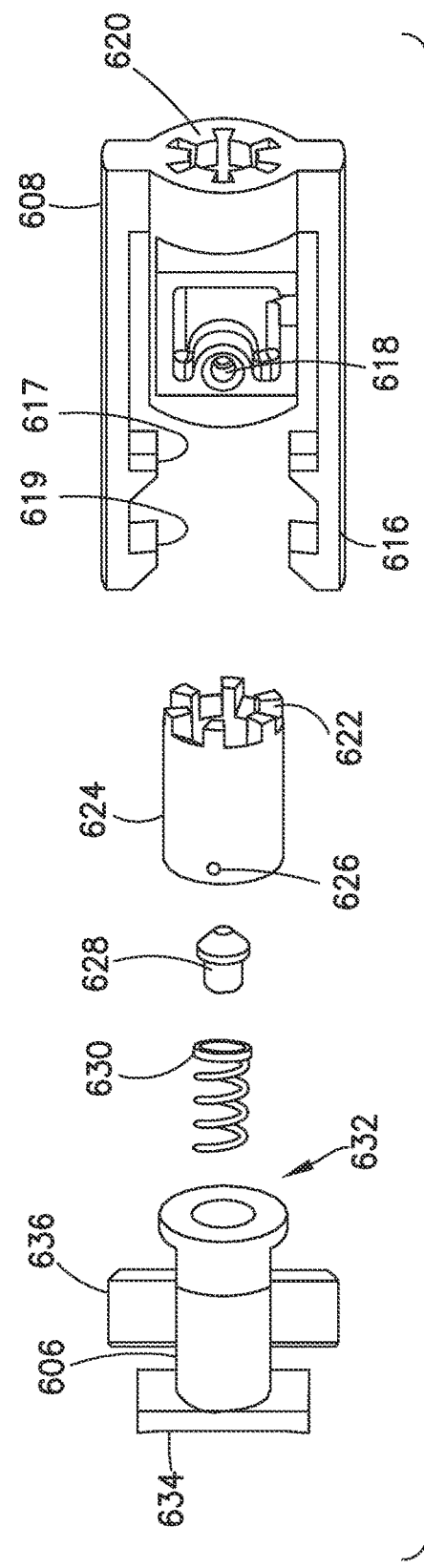
FIG. 62 is an exploded, top perspective view of a portion of a valve assembly in accordance with an embodiment of the present invention.
Figure 63:
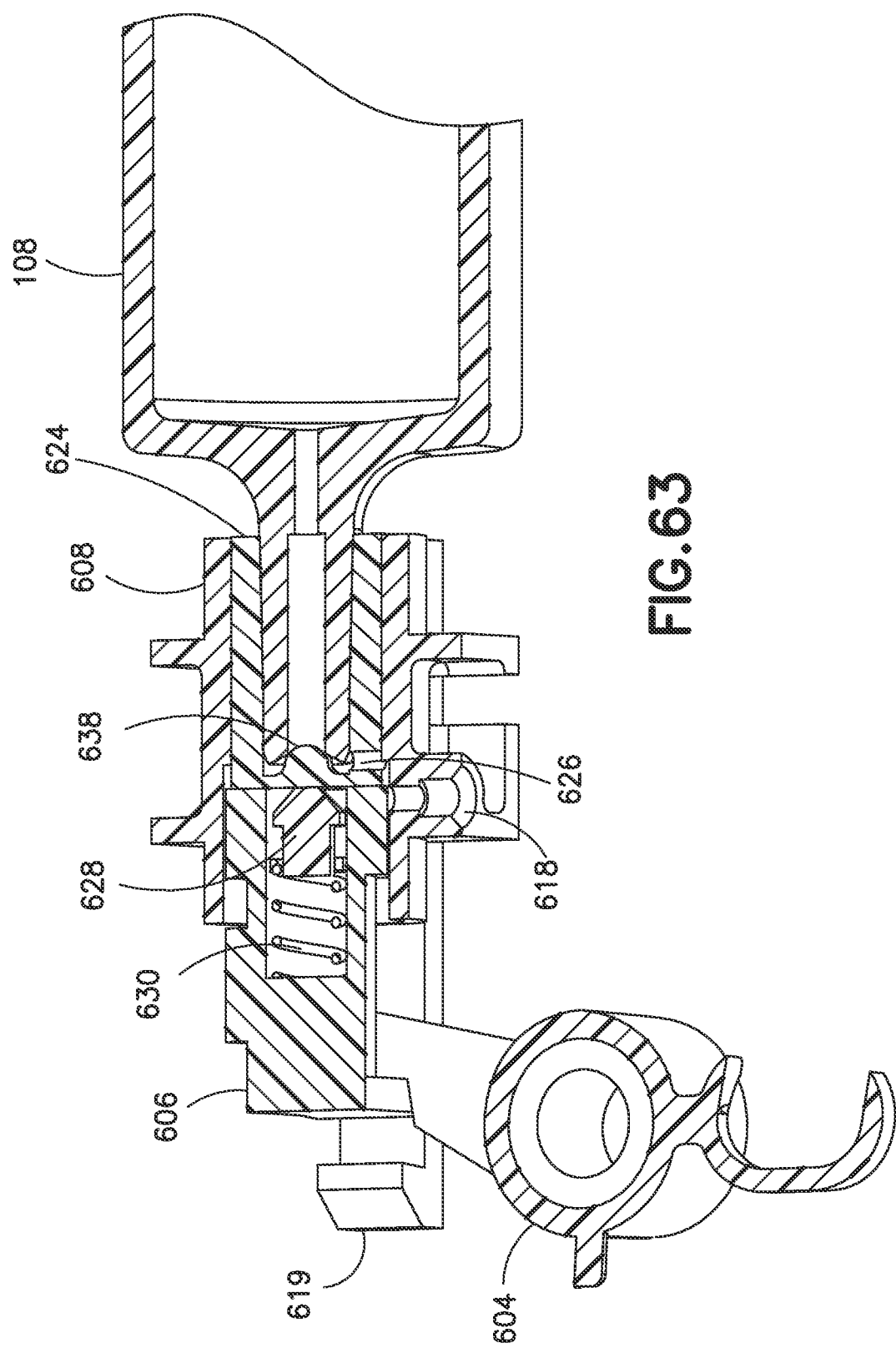
FIG. 63 is a cross-sectional, perspective plan view of a valve assembly in accordance with an embodiment of the present invention.

FIG. 62 is an exploded view illustrating additional components of the valve assembly 602, and FIG. 63 is a cross-sectional perspective plan view of the valve assembly 602. The septum fitting 608 includes teeth 620 at its first end that correspond with teeth 622 disposed at a first end of a one-piece plug valve 624, to prevent relative rotation between the septum fitting 608 and the plug valve 624. The plug valve 624 has a central lumen that fluidly communicates with the tip of the syringe barrel 108, and also has a side port 626 connected with the central lumen and aligned with the septum fitting's side port 618. The valve release cap 606 includes an end block 634 for securing the valve release cap 606 in a pre-activated position, and a guide block 636 that rides against a registration surface of the septum fitting 608 to prevent relative rotation between the septum fitting 608 and the valve release cap 606.

Prior to activation, as shown in FIG. 63, retaining protrusions at the free end of the septum fitting's base arms 616 retain an end block 634 of the valve release cap 606. An inner spring 630 is disposed within a cavity 632 of the valve release cap 606 and biases a valve impactor 628 toward the syringe barrel 108. Under the force of the inner spring 630, the valve impactor contacts and elastically deforms the end of the plug valve, thereby causing an internal valve protrusion 638 to seal the syringe barrel tip 626 and prevent medicament in the syringe barrel 108 from flowing through the side ports 626 and 618.

Figure 64:
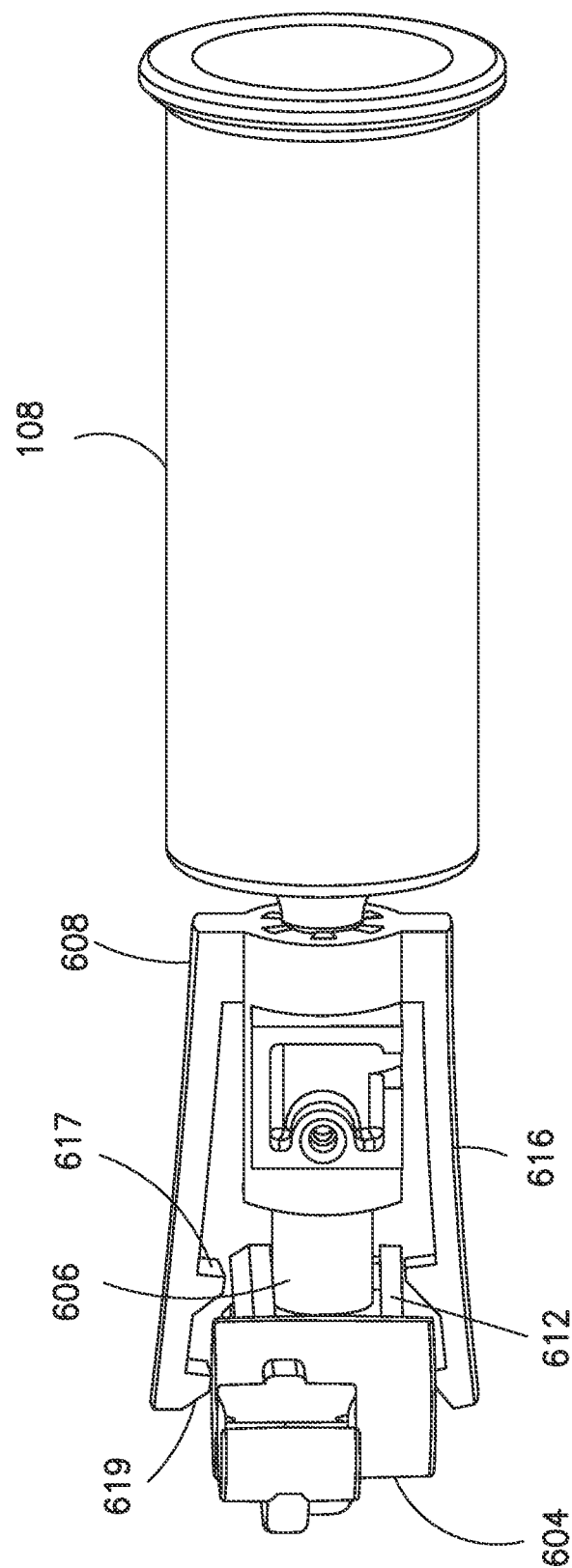
FIG. 64 is a partial perspective view of the valve assembly of FIG. 63.
Figure 65:
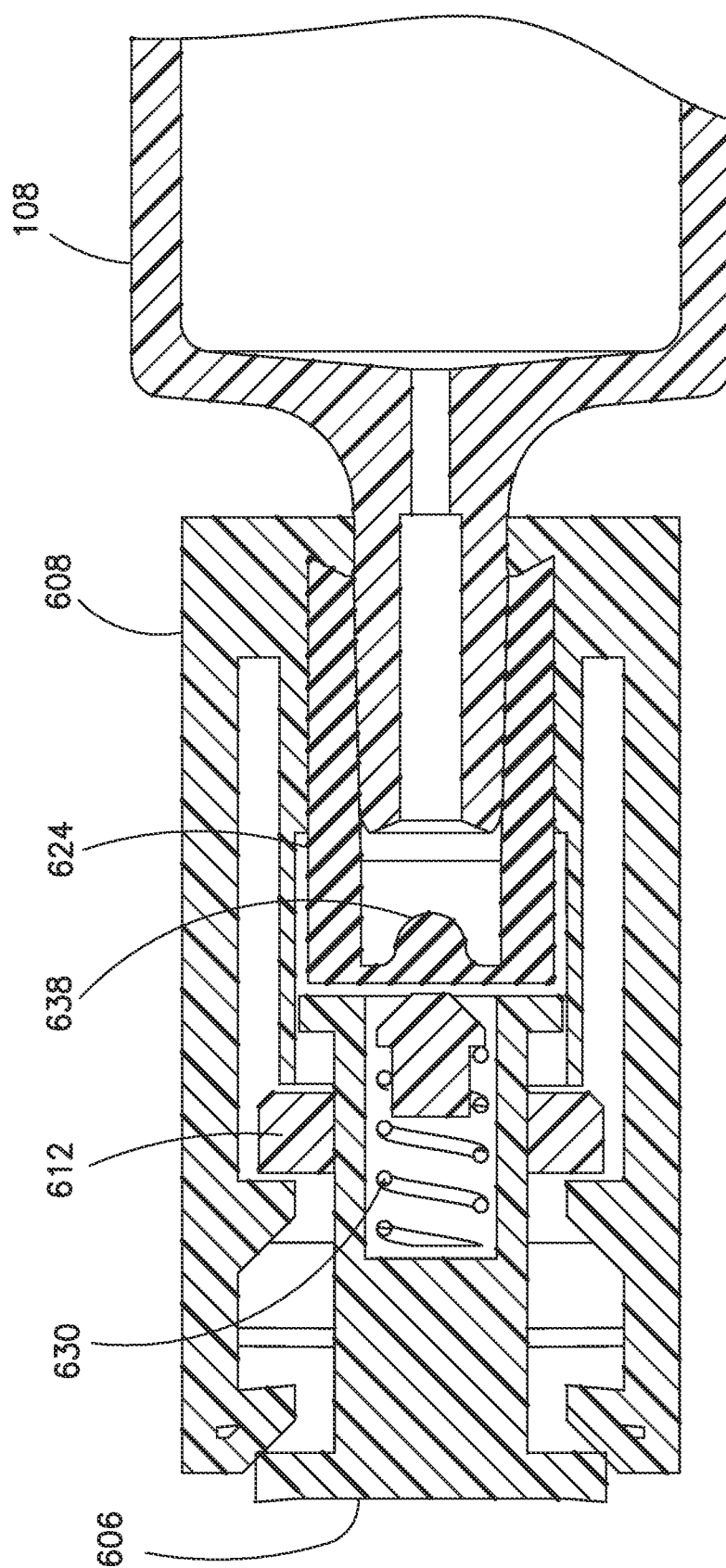
FIG. 65 is a side cross-sectional view of the valve assembly of FIG. 63.

Upon activation, as illustrated in FIG. 64, the as the rocker arms 612 rotate toward the syringe barrel 108, they contact and displace the splaying protrusions 617, splaying the free ends of the septum fitting's cantilevered base arms 616, and releasing the end block 634 from the retaining protrusions 619. Subsequently, as shown in FIG. 65, the rocker arms 612 bypass the splaying protrusions 617, and the spring 630 forces the valve release cap away from the syringe barrel 108. Because the spring 630 is substantially no longer biasing the valve impactor 628, the plug valve 624 returns to its un-deformed shape, displacing the internal valve protrusion 638 out of sealing engagement with the tip of the syringe barrel 108 and permitting medicament in the syringe barrel 108 to flow through the side ports 626 and 618.

Figure 66:
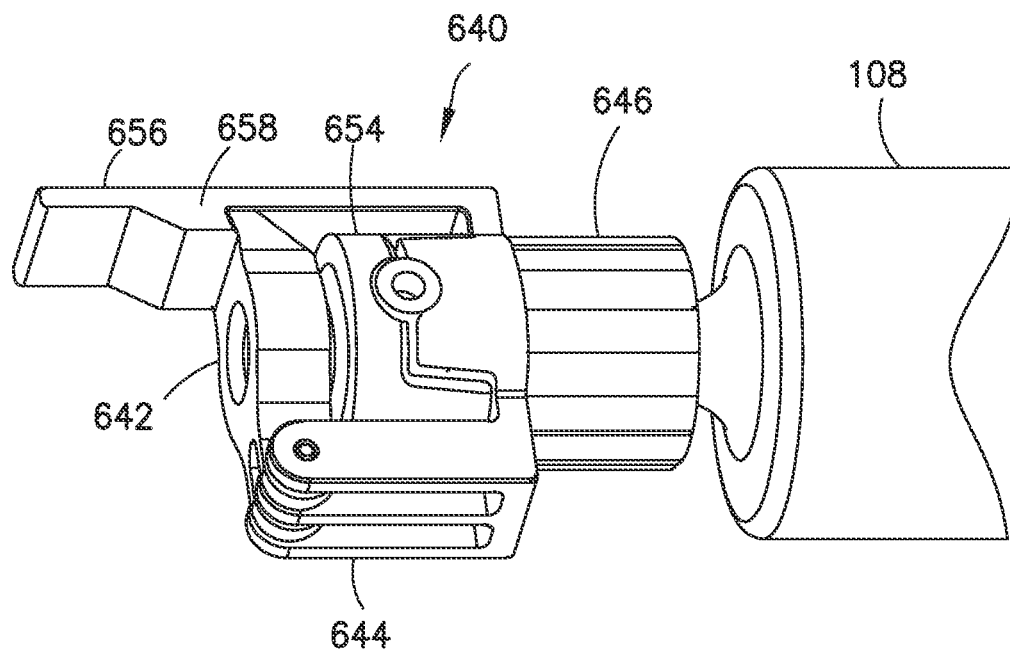
FIG. 66 is a bottom perspective view of a valve assembly in accordance with another embodiment of the present invention.
Figure 67:
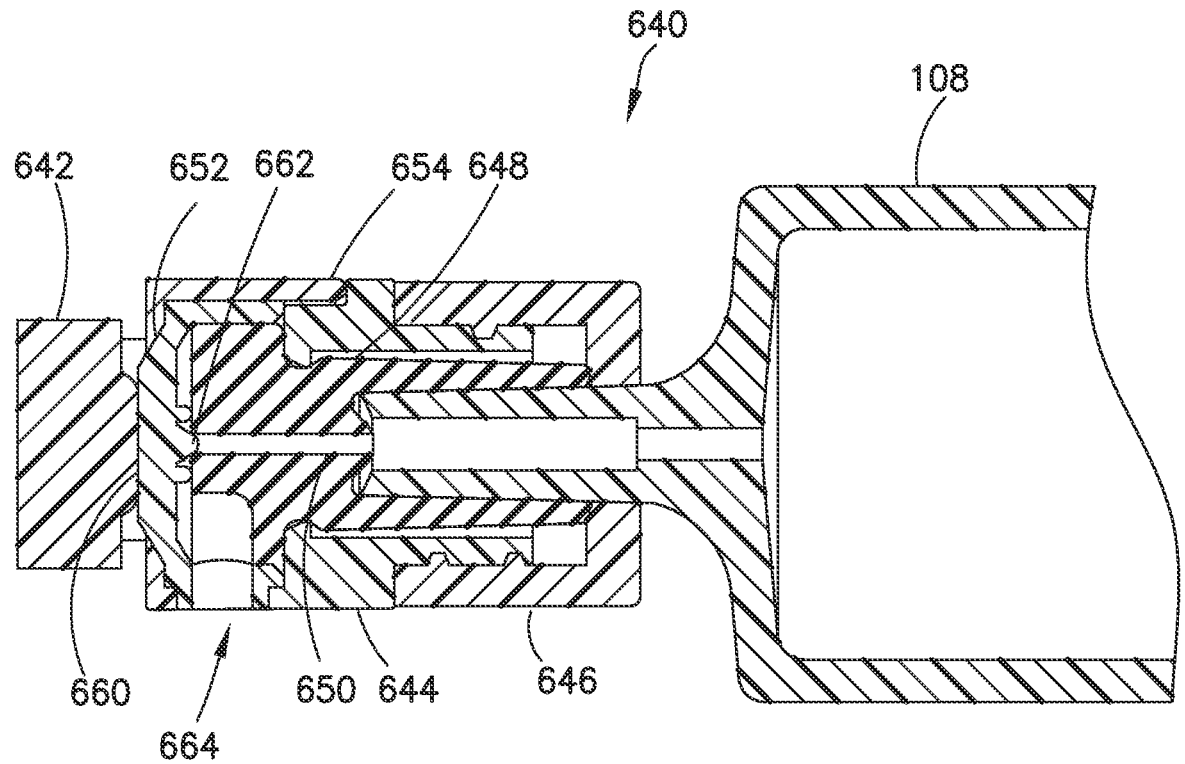
FIG. 67 is a partial, cross-sectional, plan view of the valve assembly of FIG. 66.

FIG. 66 is a bottom perspective view of a valve assembly 640 and FIG. 67 is a partial, cross-sectional, plan view of the valve assembly 640. FIGS. 66 and 67 illustrate a state prior to device activation. The valve assembly includes a lid 642 hingedly connected to a lid retainer 644, a valve case 646 connected with the tip of the syringe barrel 108, a valve body 648 disposed within the valve case and having a central lumen 650 fluidly communicating with the interior of the syringe barrel 108, an elastomeric valve member 652, and a cover 654 securing the valve member 652 to the valve body 648.

The lid retainer 644 includes a cantilevered retainer arm 656 with a catch 658 to selectively retain the lid 642. The lid 642 includes a lid protrusion 660 for selectively compressing the valve member 652 to seal the valve body's central lumen 650. The valve member 652 includes one or more sealing protrusions 662 (for example, a protrusion and a ring) that seal the central lumen 650 when the valve member 652 is compressed by the lid 642. The valve member 652 also includes a side port 664 for communicating with the patient needle via the tubing.

Upon device activation, an angled rocker arm (not shown) wedges up the retainer arm 656 freeing the catch 658 from the lid 642. Once the lid 642 is freed, the valve body 648 returns to its un-deformed shape, and rotates the lid away from the syringe barrel 108 while unsealing the central lumen 650, thereby permitting the medicament to flow from the syringe barrel 108, through the central lumen 650, and through the interior of the valve body 648 to the side port 664.

Except for needles and septa, unless otherwise specified the preferred materials for the components of the medical devices described herein are suitable plastics, such as ABS. Other suitable plastics can also be employed.

Figure 68:
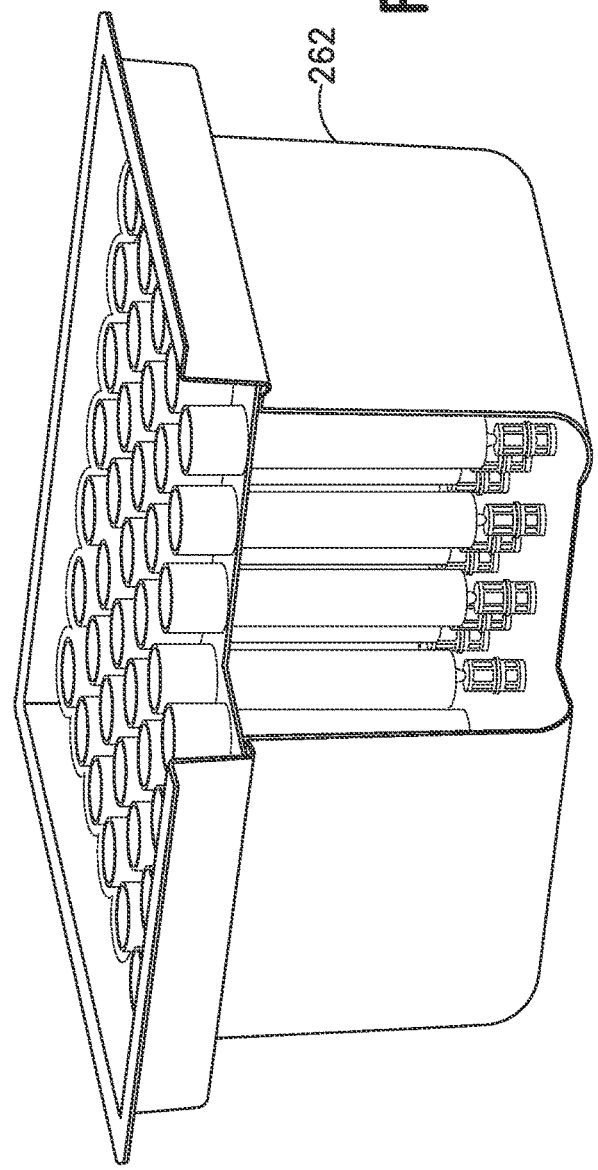
FIG. 68 is a perspective view of a tub for containing syringes.

FIG. 68 illustrates a tub 262 for containing and processing (for example, filling) syringes, such as 10 mL BD Hypak™ syringes. One skilled in the art will appreciate that any size syringe can be used and the tub can be sized and configured accordingly. The tub can be a four inch tub and can accommodate 42 barrels (Hypak™ syringes) per tub. As subsequently described in greater detail, the manufacturing process for the device 100 utilizes components that allow for the use of such tubs and standard syringe processing equipment.

Figure 69:
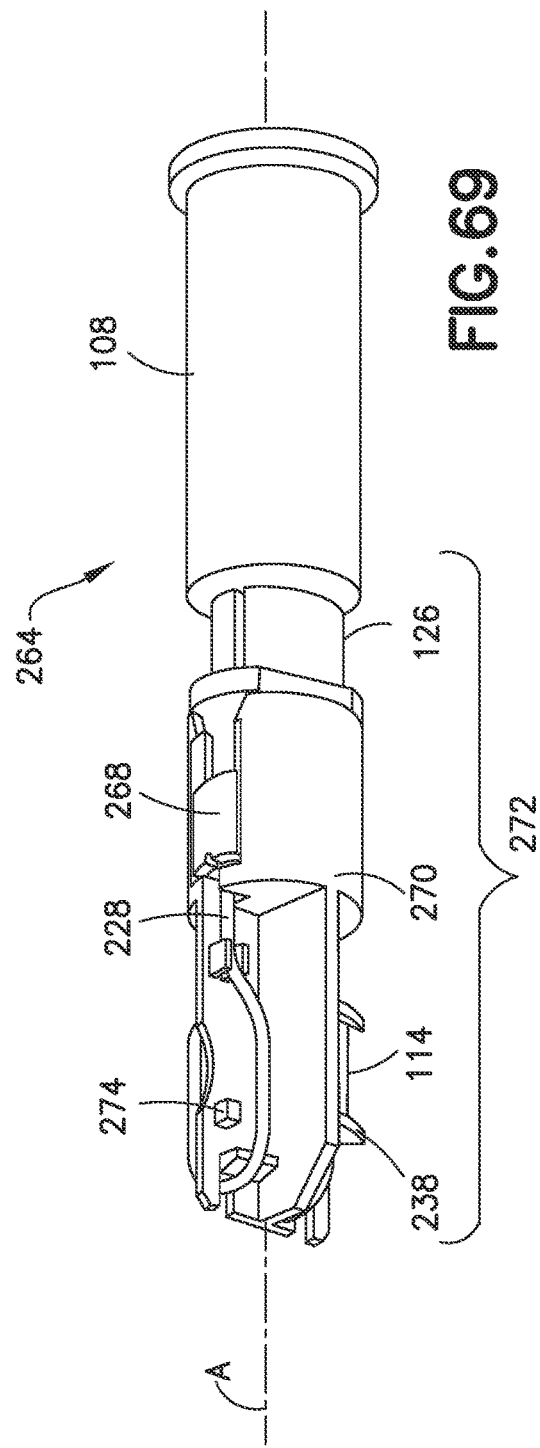
FIG. 69 is a perspective view of a fluid path subassembly in accordance with an embodiment of the present invention.
Figure 70:
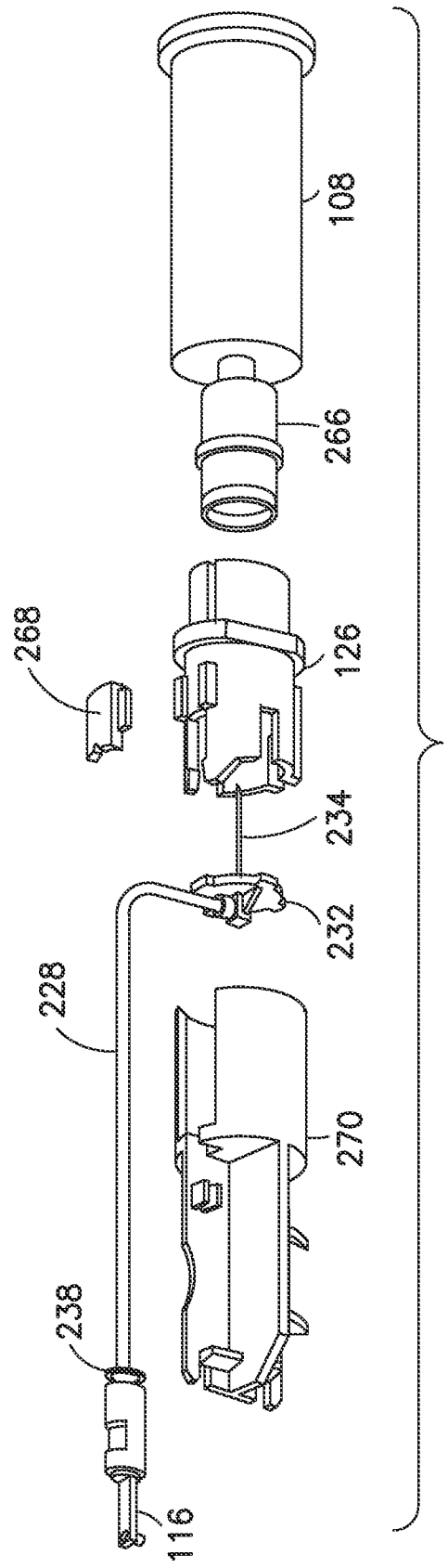
FIG. 70 is an exploded perspective view of the fluid path subassembly of FIG. 69.

FIG. 69 is a perspective view of a fluid path subassembly 264 in accordance with an embodiment of the present invention, and FIG. 70 is an exploded perspective view of the fluid path subassembly 264. The fluid path subassembly 264 includes the syringe barrel 108, the stopper 172 (not shown in FIGS. 69 and 70), the valve cover 126, an adapter 266 for connecting the syringe barrel 108 with the valve cover 126, the hollow valve needle 234, the valve plate 232, and a locking element or lock 268 to selectively prevent the valve plate 232 from moving with respect to the valve cover 126. According to one embodiment, the valve septum 236 is disposed within the adapter 266. The fluid path subassembly 264 also includes the connecting tube 228, the port or needle hub 238, the hollow patient needle 124, the needle cover 114, and a sacrificial retainer 270 for holding the components of the fluid path subassembly 264 prior to installation in the bottom cover 104.

In other words, the fluid path subassembly 264 includes all of the elements of the device that contact the medicament fluid plus the retainer 270 and the locking element 268. Additionally, the elements of the fluid path subassembly 264 minus the barrel 108 and the stopper 172 form a flow pathway subassembly 272, as subsequently described in greater detail. Although fluid path subassembly 264 in this embodiment is envisioned to be used in device 100, such a fluid path subassembly can also be utilized in other types of devices, such as autoinjectors, medication pens, and virtually any pre-filled device that requires sterility maintenance in the fluid path.

Preferably, the retainer 270 is re-usable. According to one embodiment, the retainer also includes a balancing feature or balancing weight 274 (see FIG. 69) for balancing the flow pathway subassembly 272 (as well as the fluid path subassembly 264) about its central longitudinal axis. In other words, preferably, the center of gravity of the flow pathway subassembly 272 is disposed on the central longitudinal axis, so that the subassembly 272 is rotationally balanced about the central longitudinal axis.

The balancing weight 274 can be connectable to the main body of the retainer 270, or alternatively, can be integrally formed with the main body of the retainer 270. According to one embodiment, the balancing weight 274 is adjustable relative to the main body of the retainer 270. For example, the balancing weight 274 can be affixed to different locations on the main body of the retainer 270. Alternatively, if the balancing weight 274 is integrally formed with the retainer's main body, for example, as a weight at the end of a cantilevered arm, the arm can be deformed or deflected to position the balancing weight 274. As subsequently discussed in greater detail, during inspection, the fluid path subassembly 264 is rotated at high speeds about its central longitudinal axis (for example, axis A in FIG. 69), so it is preferable that it be rotationally balanced about that axis).

As shown most clearly in FIG. 69, the retainer 270 has a path for looping and storing the connecting tube 228. This provides for space-efficient storage of the connecting tube 228, as well as protection for the tube 228. The retainer 270 also provides for convenient handling of the fluid path subassembly 264.

Once assembled, the fluid path subassemblies 264, which are substantially the same size as a 10 mL BD Hypack™ syringe barrel, can be loaded into a four-inch tub that can accommodate 42 fluid path subassemblies 264. Because of the additional components in a fluid path subassembly 264, the syringe barrel 108 is smaller than a 10 mL Hypak™ syringe barrel. According to one embodiment, the syringe barrel 108 can be filled with about 2-5 mL of medicament. Because of the size similarity of the fluid path subassembly 264 with respect to a Hypak™ syringe barrel, equipment standardized for filling and moving Hypak™ syringe barrels can be utilized to fill and move fluid path subassemblies 264.

Once the syringe barrel 108 has been filled with medicament and the stopper 172 has been inserted in the barrel 108, the medicament fluid path is self-contained, and therefore, sterile packaging or storage is not required. Instead, the fluid path subassemblies 264 can be stored and subsequently installed into the device 100 in a standard clean room.

Figure 71:
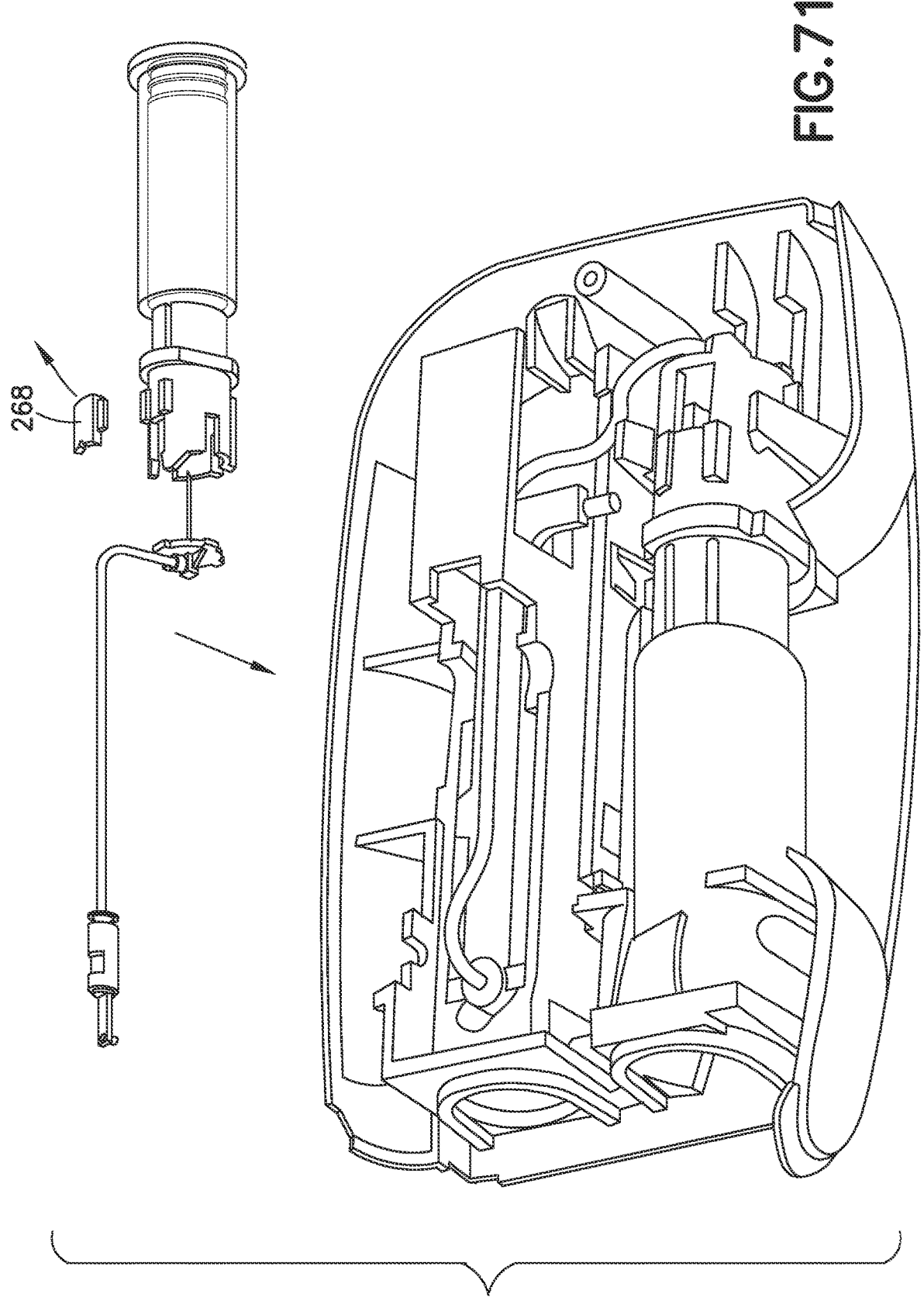
FIG. 71 is a perspective view illustrating installation of the fluid path subassembly into the device of FIG. 1.
Figure 72:
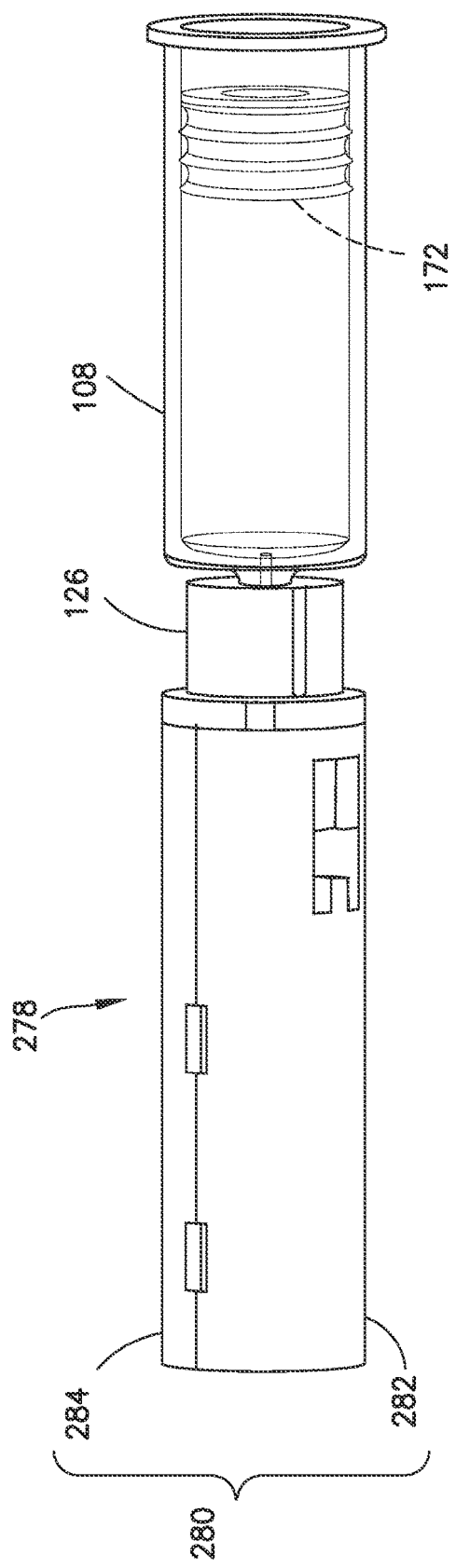
FIG. 72 is a perspective view of a fluid path subassembly in accordance with another embodiment of the present invention.

To install the fluid path subassembly 264 into the bottom cover 104, the installer unwinds the tubing 228 from the retainer 270, which is then discarded, re-used, or recycled. The installer secures the needle hub or port 238 at the end of the needle arm 130 and inserts the barrel 108 and valve cover 126 into the bottom cover 104, as shown in FIG. 71. Subsequently, the installer removes the locking element 268, which is then also discarded, re-used, or recycled.

FIGS. 25 and 72-76 illustrate another embodiment of a fluid path subassembly 278. The retainer 280 includes first and second retaining members 282 and 284. In this embodiment, the syringe barrel 108, the stopper 172, the valve cover 126, valve plate 232, the valve needle 234, the patient needle 124, and the tubing 228 are substantially similar to those previously described. Accordingly, the description of these elements is omitted for brevity. In addition, the valve cover 126 is omitted from FIG. 73 for clarity.

Figure 73:
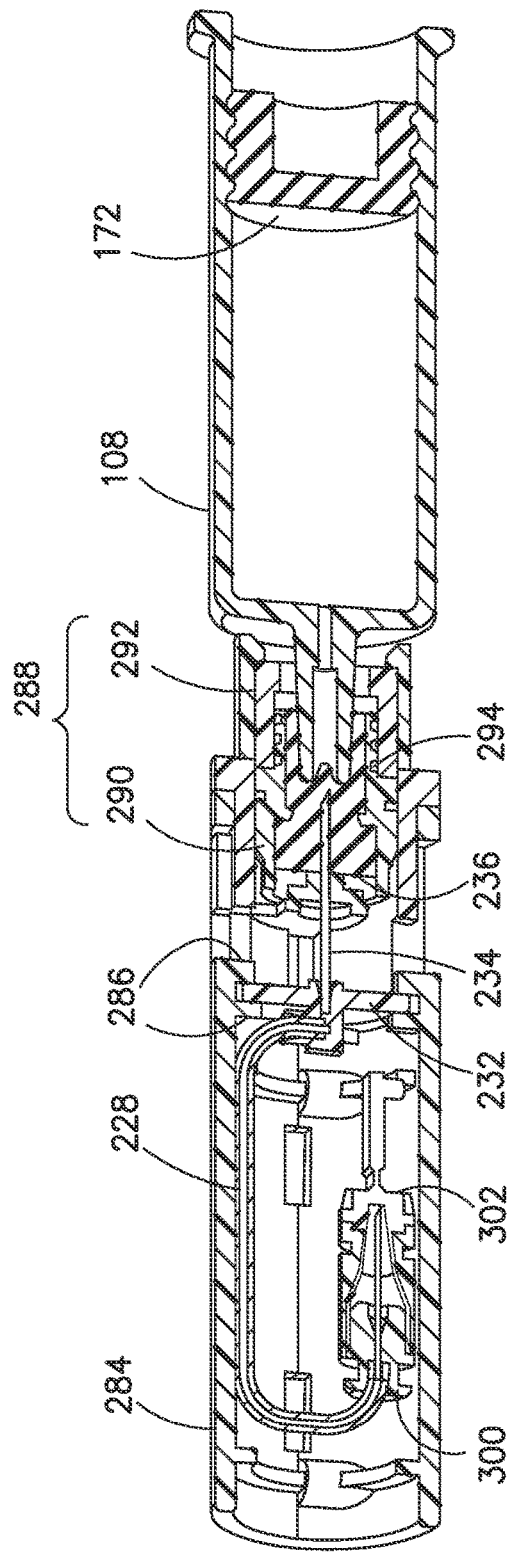
FIG. 73 is a partial cross-sectional view of the fluid path subassembly of FIG. 72 with a valve cover removed for clarity.
Figure 74:
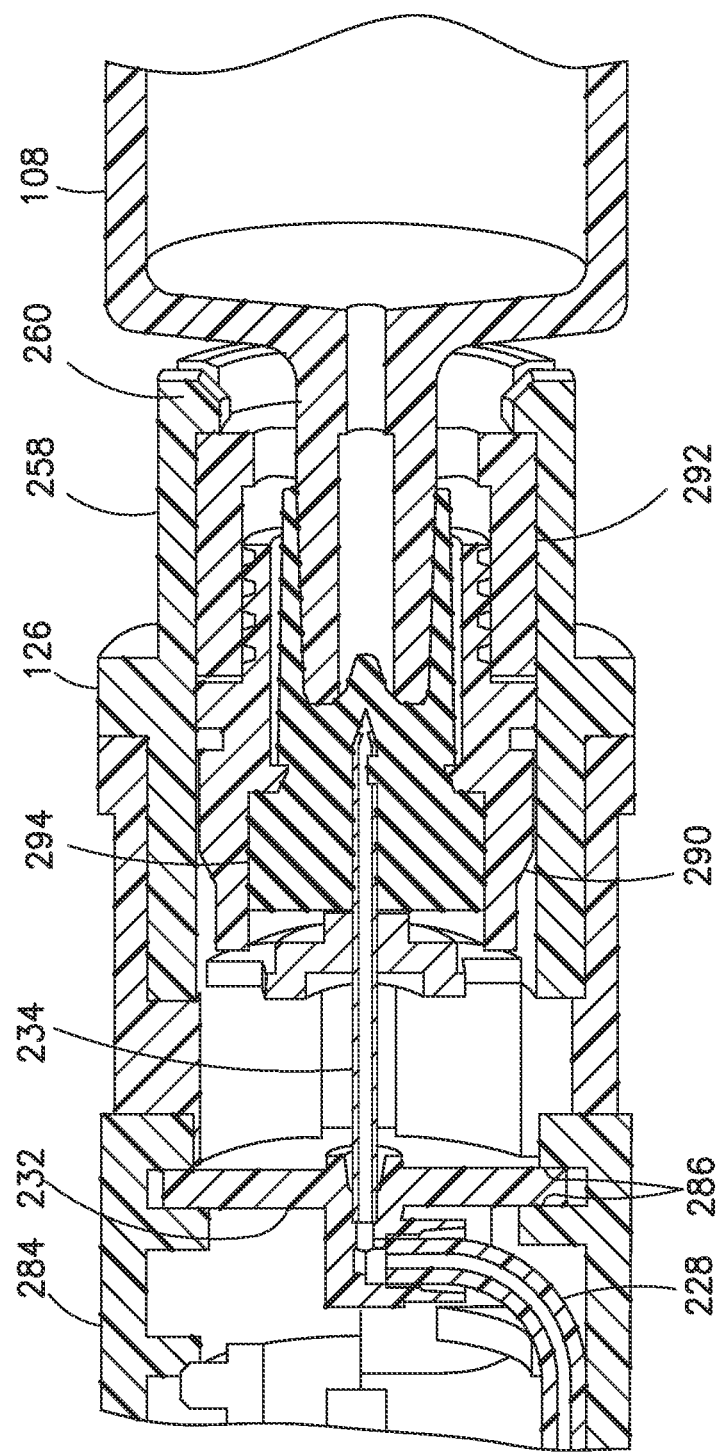
FIG. 74 is an enlarged, partial cross-sectional view of the fluid path subassembly of FIG. 72.

As shown in FIGS. 73 and 74, the first and second retaining members 282 and 284 have inward-protruding walls to engage the valve plate 232 and fix its position within the valve cover 126. Thus, without the use of a separate locking element (such as the previously-described locking element 268), the retainer 280 prevents movement of the valve plate 232 relative to the valve cover 126. Optionally, the retainer 280 has a balancing weight (not shown) similar to the previously-described balancing weight 274, to ensure that the center of gravity of the flow path assembly 278 lies on the central longitudinal axis thereof.

Figure 75:
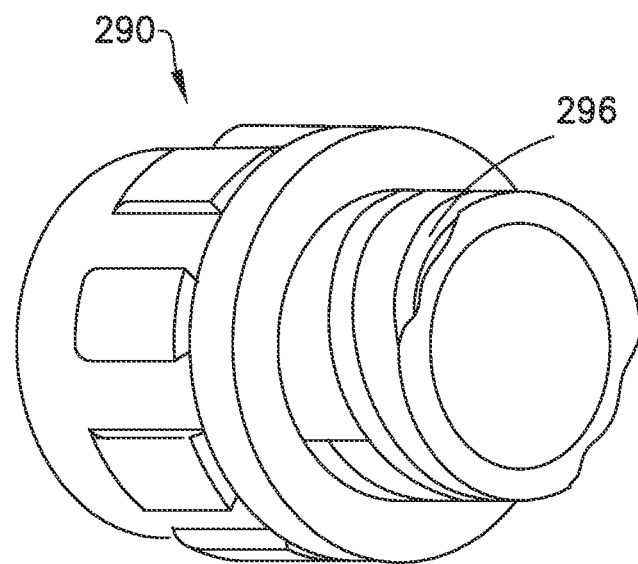
FIGS. 75 and 76 are respective perspective views of a septum holder and a connector of the fluid path subassembly of FIG. 72.
Figure 76:
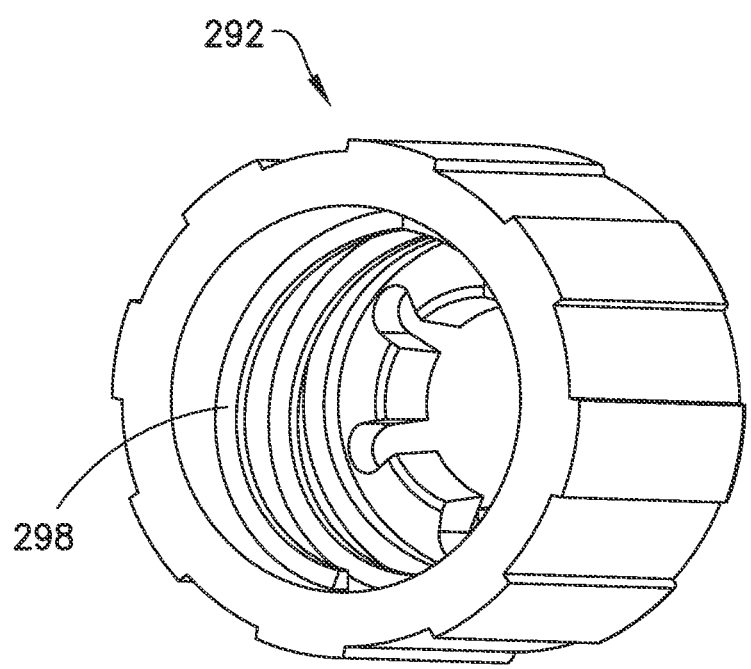

A two-piece adapter 288 includes a septum holder 290 and a connector 292 for connecting to a neck of the tip of the syringe barrel 108. The septum holder 290 secures a valve septum 294 that is penetrated by the Whitacre valve needle 234. The arms 258 and hooks 260 of the valve cover 126 secure the two-piece adapter 288 within the valve cover 126. According to one embodiment, as shown in FIGS. 75 and 76, the septum holder 290 and the connector 292 have mating screw threads 296 and 298 to secure one to the other.

FIG. 77 is a flow chart illustrating a process 310 of assembly of the device 100. In operation 312, the assembler obtains or manufacturers the spring components of the device 100, for example, the barrel spring 178 and the needle actuation spring 200. Similarly, in operation 314, the assembler molds or obtains the injection molded components, for example, the main body 106, the needle actuation plunger 166, the outer telescope member 146, and the retainer 270 or 280. Likewise, in operation 316, the assembler obtains or manufactures the primary container, for example, the syringe barrel 108. And in operation 318, the assembler obtains or manufactures the remaining components of the flow pathway subassembly 272, for example, the patient needle 124, the valve needle 234, the tubing 228, and the stopper 172.

Subsequently, in operation 320, the assembler assembles the power pack 1380 using the spring components and the appropriate injection-molded components, for example, the needle actuation plunger 166, and the barrel plunger 152. Additionally, the fluid path subassembly 264 or 278 is assembled in operation 322. The remainder of the components, i.e., those that are not in the power pack 1380 or the fluid path subassembly 264 or 278, are assembled into the device body 1060.

The assembled fluid path subassembly 264 or 278 is packaged (operation 326) and then sterilized (operation 328), thereby providing a self-contained, sterilized fluid path subassembly 264 or 278 that can be shipped to another location, for example, a pharmaceutical manufacturer, for aseptic filling (operation 330) with medicament. Subsequent to the filling, the fluid path subassembly 264 or 278 is inspected for quality during high speed rotation about its central longitudinal axis, for example, by a light-based inspection system, such as a laser inspection system. One advantage of the inventive fluid path subassembly is that it can be processed (i.e., packaged, sterilized, filled, and inspected) using equipment that is standardized for processing syringes, such as BD Hypak™ syringes. Those fluid path subassemblies that pass inspection can then be assembled into the device body 1060 along with the power pack 1380 to complete the device (operation 334).

Although only a few embodiments of the present invention have been shown and described, the present invention is not limited to the described embodiments. Instead, it will be appreciated by those skilled in the art that changes may be made to these embodiments without departing from the principles and spirit of the invention. It is particularly noted that those skilled in the art can readily combine the various technical aspects of the various elements of the various exemplary embodiments that have been described above in numerous other ways, all of which are considered to be within the scope of the invention, which is defined by the appended claims and their equivalents.

The invention claimed is:
1. A drug delivery device for injecting medicament, the device comprising:
   a main body having a surface for contacting a patient;
   a user-accessible actuation button distinct from the main body and movably disposed relative to the main body;

a reservoir disposed within the main body for containing a medicament;
at least one needle having:
a distal end for insertion into the patient; and
a lumen extending proximally from the distal end, wherein said lumen is fluidly connectable with the reservoir;
a needle hub movably disposed within the main body to hold the at least one needle; and
a removable needle cover engageable to the needle hub to cover the distal end of the needle, the needle cover including:
a needle cover portion; and
a safety extension extending internally through the main body from the needle covering portion and adapted to engage the actuation button and prevent movement of the actuation button relative to the main body that initiates activation of the device.

2. A drug delivery device for injecting medicament, the device comprising:
a main body having a surface for contacting a patient;
an actuation button distinct from the main body and movably disposed relative to the main body;
a reservoir disposed within the main body for containing a medicament;
at least one needle having:
a distal end for insertion into the patient; and
a lumen extending proximally from the distal end, wherein said lumen is fluidly connectable with the reservoir;
a needle hub movably disposed within the main body to hold the at least one needle; and
a removable needle cover selectively connectable to the needle hub to cover the distal end of the needle, the needle cover including:
a needle cover portion; and
a safety extension extending internally through the main body from the needle cover portion and adapted to engage the actuation button and prevent movement of the actuation button relative to the main body that initiates activation of the device;
wherein:
the actuation button comprises a pair of cantilevered arms; and
prior to needle cover removal, the safety extension extends between the cantilevered arms, preventing the cantilevered arms from moving toward each other and disengaging from engaging structures in the main body, thereby preventing movement of the actuation button relative to the main body that initiates activation of the device.

3. The device according to claim 1, wherein subsequent to expulsion of the medicament through the needle, the device automatically changes from an activated stage to an end-of dose stage.

4. The device according to claim 3, wherein changing from the activated stage to the end-of-dose stage retracts the distal end of the needle within the main body.

5. The device according to claim 1, wherein the needle is movably disposed with respect to the main body between a first position, in which the distal end is disposed within the main body, and a second position, in which the distal end is disposed outside the main body.

6. The device according to claim 5, wherein upon activation, the needle moves to the second position.

7. The device according to claim 1, further comprising an indicating mechanism to indicate when the device is currently in a pre-activated stage, an activated stage, and an end-of dose stage.

8. The device according to claim 1, further comprising an indicating mechanism comprising:
a needle actuation slider movably disposed within the main body and controlling insertion and retraction of the needle through movement of the needle actuation slider; and
a stage indicating structure disposed on the needle actuation slider and having indicia denoting at least the activated stage and the end-of dose stage, the indicia being visible through a status viewport in the main body;
wherein the movement of the stage indicating structure corresponds to movement of the needle actuation slider.

9. The device according to claim 8, wherein the stage indicating structure is fixedly secured to the needle actuation slider.

10. The device according to claim 9, wherein the stage indicating structure is integrally formed as a unitary structure with the needle actuation slider.

11. A drug delivery device for injecting medicament, the device comprising:
a main body having a surface for contacting a patient;
an actuation button movably disposed relative to the main body;
a reservoir disposed within the main body for containing a medicament;
at least one needle having:
a distal end for insertion into the patient through one opening in the surface; and
a lumen extending proximally from the distal end, wherein the lumen is fluidly connectable with the reservoir;
a needle hub movably disposed within the main body to hold the at least one needle; and
a removable needle cover connectable to the needle hub to cover the distal end of the at least one needle, the needle cover including:
a needle cover portion; and
a safety extension extending from the needle cover portion and adapted to engage the actuation button and prevent movement of the actuation button relative to the main body that initiates activation of the device;
wherein the safety extension and the needle cover portion are inserted through the one opening, and are removable through the one opening in a single motion.

12. The device according to claim 8, wherein the movement of the needle actuation slider is relative to the at least one needle.

13. The device according to claim 2, wherein the cantilevered arms extend in a first direction from a portion of the actuation button.

14. The device according to claim 13, wherein prior to needle cover removal, the safety extension prevents the cantilevered arms from moving laterally relative to the first direction.

15. The device according to claim 11, wherein the surface defines a closed perimeter of the opening.

16. A drug delivery device for injecting medicament, the device comprising:
a main body having a surface for contacting a patient;
an actuation button movably disposed relative to the main body;

a reservoir disposed within the main body for containing a medicament;
at least one needle having:
   a distal end for insertion into the patient; and
   a lumen extending proximally from the distal end, wherein said lumen is fluidly connectable with the reservoir;
a needle hub movably disposed within the main body to hold the at least one needle; and
a removable needle cover engageable to the needle hub to cover the distal end of the needle, the needle cover including:
   a needle cover portion; and
   a safety extension extending internally through the main body from the needle cover portion and adapted to engage the actuation button and prevent movement of the actuation button relative to the main body that initiates activation of the device;
wherein the needle cover portion and the safety extension are removable from the device in a single direction.

* * * * *